US005532151A

United States Patent [19]
Chantry et al.

[11] Patent Number: 5,532,151
[45] Date of Patent: Jul. 2, 1996

[54] G PROTEIN-COUPLED RECEPTOR KINASE GRK6

[75] Inventors: David Chantry; Patrick W. Gray, both of Seattle; Merl F. Hoekstra, Snohomish, all of Wash.

[73] Assignee: ICOS Corporation, Bothell, Wash.

[21] Appl. No.: 221,817

[22] Filed: Mar. 31, 1994

Related U.S. Application Data

[63] Continuation-in-part of Ser. No. 123,932, Sep. 17, 1993, abandoned.

[51] Int. Cl.$^6$ .............................. C12N 9/12; C12Q 1/68; C07H 19/00; C07H 21/00
[52] U.S. Cl. .................... 435/194; 435/6; 435/240.2; 435/252.3; 435/320.1; 536/22.1; 536/23.1; 536/23.2; 536/23.5
[58] Field of Search ........................... 435/6, 194, 240.2, 435/252.3, 320.1; 536/22.1, 23.1, 23.2, 23.5

[56] References Cited

FOREIGN PATENT DOCUMENTS

WO93/05182  3/1993  WIPO.

OTHER PUBLICATIONS

Adams et al., "Sequence identification of 2,375 human brain genes", *Nature*, 355:632–634 (1992).
Ambrose et al., "A novel G protein–coupled receptor kinase gene cloned from 4p16.3", *Hum. Mol. Genet.*, 1:697–703 (1992).
Benovic et al., "Cloning, Expression, and Chromosomal Localization of β–Adrenergic Receptor Kinase 2", *J. Biol. Chem.*, 266:14939–14946 (1991).
Benovic et al., "β–Adrenergic Receptor Kinase: Primary Structure Delineates a Multigene Family", *Science*, 246:235–240 (1989).
Benovic et al., "Molecular Cloning and Expression of GRK6", *J. Biol. Chem.*, 268(26): 19521–19527 (Sep. 1993).
Bouwer et al., "Adoptive Transfer of Experimental Allergic Encephalomyelitis: Conditions Influencing Memory and Effector Cell Development", *Cellular Immunol.*, 131:219–231 (1990).
Cassill et al., "Isolation of *Drosophila* genes encoding G protein–coupled receptor kinases", *Proc. Natl. Acad. Sci. USA*, 88:11067–11070 (1991).
Dohlman et al., "Model Systems For The Study of Seven-–Transmembrane–Segment Receptors", *Ann. Rev. Biochem.*, 60:653–688 (1991).
Erbeck et al., "Differential Uncoupling of Chemoattractant Receptors from G Proteins in Retinoic Acid–Differentiated HL–60 Granulocytes", *J. Immunol.*, 150:1913–1921 (1993).
Erickson et al., "Macromolecular X—Ray Crystallography and NMR as Tools for Structure–based Drug Design", *Ann. Rev. Med. Chem.*, 27:271–289 (1992).
Gerard et al., "The chemotactic receptor for human C5a anaphylatoxin", *Nature*, 349:614–617 (1991).

Hanks et al., "Protein Kinase Catalytic Domain Sequence Database: Identification of Conserved Features of Primary Structure . . .", *Meth. Enzymol.*, 200:38–62 (1991).
Haribabu et al., "Identification of additional members of human G–protein–coupled receptor kinase multigene family", *Proc. Natl. Acad. Sci. USA*, 90:9398–9402 (Oct. 1993).
Holmes et al., "Structure and Functional Expression of a Human Interleukin–8 Receptor", *Science*, 253:1278–1280 (1991).
Inglese et al., "Isoprenylation of a Protein Kinase", *J. Biol. Chem.*, 267:1422–1425 (1992).
Khorana, "Rhodopsin, Photoreceptor of Rod Cell", *J. Biol. Chem.*, 267:1–4 (1992).
Klein et al., "cAMP Induces a Rapid and Reversible Modification of the Chemotactic Receptor in *Dictyostelium discoideum*", *J. Cell Biol.*, 100:715–720 (1985).
Koga et al., "A human T cell–specific cDNA clone (YT16) encodes a protein with extensive homology to a family of protein–tyrosine kinases", *Eur. J. Immunol.*, 16:1643–1646 (1986).
Kozak, "An Analysis of Vertebrate mRNA Sequences: Intimations of Translational Control", *J. Cell. Biol.*, 115: 887–903 (1991).
Kunapuli et al., "Cloning and expression of GRK5: A member of the G protein–coupled receptor kinase family", *Proc. Natl. Acad. Sci. USA*, 90:5588–5592 (1993).
Kwatra et al., "Correlation of Agonist–induced Phosphorylation of Chick Heart Muscarinic Receptors with Receptor Desensitization", *J. Biol. Chem.*, 262:16314–16321 (1987).
LaVallie et al., "A Thioredoxin Gene Fusion Expression System that Circumvents Inclusion Body Formation in the *E. Coli* Cytoplasm", *Biotechnology*, 11:187–193 (1993).
Lefkowitz, "G Protein–Coupled Receptor Kinases", *Cell*, 74:409–412 (1993).
Linder et al., "G Proteins", *Sci. Am.*, 267:56–65 (1992).
Lorenz et al., "The receptor kinase family: Primary structure of rhodopsin kinase reveals similarities to the β–adrenergic receptor kinase", *Proc. Natl. Acad. Sci.*, 88:8715–8719 (1991).
Maldonado et al., "A cDNA clone encoding human cAMP-–dependent protein kinase catalytic subunit Cα", *Nuc. Acids Res.*, 16:8189–8190 (1988).
Murphy et al., "Cloning of Complementary DNA Encoding a Functional Human Interleukin–8 Receptor", *Science*, 253:1280–1283 (1991).

(List continued on next page.)

Primary Examiner—Robert A. Wax
Assistant Examiner—Hyosuk Kim
Attorney, Agent, or Firm—Marshall, O'Toole, Gerstein, Murray & Borun

[57] ABSTRACT

The present invention provides purified and isolated polynucleotide sequences encoding the novel G protein-coupled receptor kinase designated GRK6. Also provided by the invention are methods and materials for the recombinant production of GRK6 enzyme and methods for identifying compounds which modulate the protein kinase activity of GRK6.

14 Claims, 13 Drawing Sheets

OTHER PUBLICATIONS

Neote et al., "Molecular Cloning, Functional Expression, and Signaling Characteristics of a C–C Chemokine Receptor", *Cell*, 72:415–425 (1993).

Oskenberg et al. "A single amino–acid difference confers major pharmacological variation between human and rodent 5–$HT_{1B}$ receptors", *Nature*, 360:161–163 (1992).

Palczewski et al., "Identification of the N–terminal Region in Rhodopsin Kinase Involved in Its Interaction with Rhodopsin", *J. Biol. Chem.*, 268:6004–6013 (1993).

Palczewski et al., "G–protein–coupled receptor kinases", *Trends Biochem. Sci.*, 16:387–391 (1991).

Parker et al., "The Complete Primary Structure of Protein Kinase C—Major Phorbol Ester Receptor", *Science*, 233:853–859 (1986).

Pippig et al., "Overexpression of β–Arrestin and β–Adrenergic Receptor Kinase Augment Desensitization of $β_2$–Adrenergic Receptors", *J. Biol. Chem.*, 268:3201–3208 (1993).

Probst et al., "REVIEW ARTICLE: Seqeunce Alignment of the G–Protein Coupled Receptor Superfamily", *DNA and Cell Biol.*, 11:1–20 (1992).

Reneke et al., "The Carboxy–Terminal Segment of the Yeast α–Factor Receptor Is a Regulatory Domain", *Cell*, 55:221–234 (1988).

Schleicher et al., "A β–adrenergic receptor kinase–like enzyme is involved in olfactory signal termination", *Proc. Natl. Acad. Sci. USA*, 90:1420–1424 (1993).

Thomas et al., "Molecular cloning of the fMet–Leu–Phe Receptor from Neutrophils", *J. Biol. Chem.*, 265:20061–20064 (1990).

| | | | | | |
|---|---|---|---|---|---|
| GRK6 | ME---LENIV | ANTVLLKARE | --GGGGNRKG | KSKKWROMLQ | FPHISQCEEL | 45 |
| GRK5 | ME---LENIV | ANTVLLKARE | --GGGGKRKG | KSKKWKEILK | FPHISQCEDL | 45 |
| IT-11 | ME---LENIV | ANSLLLKARQ | ---------- | ---------- | ---------- | 17 |
| RK | MDFGSLETVV | ANSAFIAARG | SFDASSGPAS | RDRKYLARLK | LPPLSKCEAL | 50 |
| GPRK2 | M--------- | ---------- | ---------- | ---------- | ---------- | 1 |
| BARK1 | MA--DLEAVL | ADVSYLMAME | KSKATPAARA | SKKILLPEPS | IRSVMQ-KYL | 47 |
| BARK2 | MA--DLEAVL | ADVSYLMAME | KSKATPAARA | SKKVLPEPS | IRSVMQ-RYL | 47 |
| GPRK1 | MA--DLEAVL | ADVSYLMAME | KSKCTPAARA | SKKLNLPDPS | VRSVMY-KYL | 47 |

| | | | | | |
|---|---|---|---|---|---|
| GRK6 | RLSLERDYHS | LCERHRIGRL | LFREFC-ATR | PELSRCVAFL | DGVAEYE-VT | 93 |
| GRK5 | RRTIDRDYCS | LCDKQPIGRL | LFRQFC-ETR | PGLECYIQFL | DSVAEYE-VT | 93 |
| IT-11 | ---EKDYSS | LCDKQPIGRR | LFRQFC-DTK | PTLKRHIEFL | DAVAEYE-VA | 61 |
| RK | RESLDLGFEG | MCLEQPIGKR | LFQQFL-RTH | EQHGPALQLW | KDIEDYD-TA | 98 |
| GPRK2 | ---------- | ---------- | ---------- | ---------- | ---------- | 1 |
| BARK1 | EDRGEVTFEK | I-FSQKLGYL | LFRDFCLNHL | EEARPLVEFY | EEIKKYEKLE | 96 |
| BARK2 | AERNEITFDK | I-FNQKIGFL | LFKDFCLNEI | GEAVPQVKFY | EEIKEYEKLD | 96 |
| GPRK1 | EKEGELNFHK | N-FNEVLGYL | LFKDFCENDS | EEPIQQLKFF | EQIKLFEKTE | 96 |

FIGURE 1A

| | | | | | | |
|---|---|---|---|---|---|---|
| GRK6  | PDDKRKACGR | HVTQNFLSHT | GPDLIPEVPR | QLVTNCTQRL | -EQGPCKDLF | 142 |
| GRK5  | PDEKLGEKGK | EIMTKYLTPK | SPVFIAQVGQ | DLVSQTEEKL | -LQKPCKELF | 142 |
| IT-11 | DDEDRSDCGL | SILDRFFNDK | LAAPLPEIPP | DVVTECRLGL | KEENPSKKAF | 111 |
| RK    | DDALRPQKAQ | ALRAAYLEPQ | AQLFCSFLDA | ETVARAR--- | --AGAGDGLF | 143 |
| GPRK2 | ---------- | ---------- | ---------- | ---------- | ---------- | 1   |
| BARK1 | TEEERVARSR | EIFDSYIMKE | LLACSHPFSK | SATEHVQGHL | GKKQVPPDLF | 146 |
| BARK2 | NEEDRLHRSR | QMYDAYIMKE | LSSSTHQFSK | QAVEHVQSHL | SKKQVTPTLF | 146 |
| GPRK1 | CYDERKKMAR | DIYDNFIMEE | MLSHTYEYSK | HAVASVQKYL | LKNEVPVDLF | 146 |
| GRK6  | QELTRLTHEY | LSVAPFADYL | DSIYFNRFLQ | WKWLERQ-PV | TKNTFRQYRV | 191 |
| GRK5  | SACAQSVHEY | LRGEPFHEYL | DSMFFDRFLQ | WKWLERQ-PV | TKNTFRQYRV | 191 |
| IT-11 | EECTRVAHNY | LRGEPFEEYQ | ESSYFSQFLQ | WKWLERQ-PV | TKNTFRHYRV | 160 |
| RK    | QPLLRAVLAH | LGQAPFQEFL | DSLYFLRFLQ | WKWLEAQ-PM | GEDWFLDFRV | 192 |
| GPRK2 | ---------- | ---YFHRYLQ | ---YFHRYLQ | WKWLEAQ-PI | TYKTFRMYRV | 27  |
| BARK1 | QPYIEEICQN | LRGDVFQKFI | ESDKFTRFCQ | WKNVELNIHL | TMNDFSVHRI | 196 |
| BARK2 | QPYIEEICES | LRGDIFQKFM | ESEKFTRFCQ | WKNVELNIHL | SMNDFSVHRI | 196 |
| GPRK1 | EPYLEEIFTQ | LKGKPFKKFL | ESDKFTRFCQ | WKNLELNIQL | TMNDFSVHRI | 196 |

FIGURE 1B

| | | | | | |
|---|---|---|---|---|---|
| GRK6 | LGKGGFGEVC | ACQVRATGKM | YACKKLEKKR | IKKRKGEAMA | LNEKQILEKV | 241 |
| GRK5 | LGKGGFGEVC | ACQVRATGKM | YACKRLEKKR | IKKRKGESMA | LNEKQILEKV | 241 |
| IT-11 | LGKGGFGEVC | ACQVRATGKM | YACKKLQKKR | IKKRKGEAMA | LNEKRILEKV | 210 |
| RK | LGRGGFGEVF | ACQMKATGKL | YACKKLNKKR | LKKRKGYQGA | MVEKKILAKV | 242 |
| GPRK2 | LGKGGFGEVC | ACQVRATGKM | YACKKLEKKR | IKKRKGESMV | LIEKQILQKI | 77 |
| BARK1 | IGRGGFGEVY | GCRKADTGKM | YAMKCLDKKR | IKMKQGETLA | LNERIMLSLV | 246 |
| BARK2 | IGRGGFGEVY | GCRKADTGKM | YAMKCLDKKR | VKMKQGETLA | LNERIMLSLV | 246 |
| GPRK1 | IGRGGFGEVY | GCRKADTGKM | YAMKCLDKKR | IKMKQGEMLA | LNERNMLQAV | 246 |

| | | | | | |
|---|---|---|---|---|---|
| GRK6 | ----NSRFVV | SLAYAYETKD | ALCLVLTLMN | GGDLKFHIYH | MG-Q-AGFPE | 285 |
| GRK5 | ----NSQFVV | NLAYAYETKD | ALCLVLTIMN | GGDLKFHIYN | MG-N-PGFEE | 285 |
| IT-11 | ----QSRFVV | SLAYAYETKD | ALCLVLTIMN | GGDLKFHIYN | LG-N-PGFDE | 254 |
| RK | ----HSRFIV | SLAYAFETKT | DLCLVMTIMN | GGDIRYHIYN | VDEDNPGFQE | 288 |
| GPRK2 | ----NSPFVV | NLAYAYETKD | ALCLVLTIMN | GGDLKFHIYN | MGGE-PGFEL | 122 |
| BARK1 | STG-DCPFIV | CMSYAFHTPD | KLSFILDLMN | GGDLHYHLSQ | HG-----VFSE | 291 |
| BARK2 | STG-DCPFIV | CMTYAFHTPD | KLCFILDLMN | GGDMHYHLSQ | HG-----VFSE | 291 |
| GPRK1 | STGIDCPFIV | CMTYAFHTPD | KLCFILDLMN | GGDLHYHLSQ | HG-----IFSE | 292 |

FIGURE 1C

| | | | | | |
|---|---|---|---|---|---|
| GRK6  | ARAVFYAAEI | CCGLEDLHRE | RIVYRDLKPE | NILLDDHGHI | RISDLGLAVH | 334 |
| GRK5  | ERALFYAAEI | LCGLEDLHRE | NTVYRDLKPE | NILLDDYGHI | RISDLGLAVK | 335 |
| IT-11 | QRAVFYAAEL | CCGLEDLQRE | RIVYRDLKPE | NILLDDRGHI | RISDLGLATE | 304 |
| RK    | PRAIFYTAQI | VSGLEHLHQR | NIIYRDLKPE | NVLLDDDGNV | RISDLGLAVE | 338 |
| GPRK2 | ERARFYAAEV | ACGLQHLHKQ | GIVYRDCKPE | NILLDDHGHV | RISDLGLAVE | 172 |
| BARK1 | ADMRFYAAEI | ILGLEHMHNR | FVVYRDLKPA | NILLDEHGHV | RISDLGLACD | 341 |
| BARK2 | KEMRFYASEI | ILGLEHMHTC | FVVYRDLKPA | NILLDEYGHV | RISDLGLACD | 341 |
| GPRK1 | DEMKFYAAEV | ILGLEHMHKR | CIVYRDLKPA | NILLDENGHI | RISDLGLACD | 342 |

| | | | | | |
|---|---|---|---|---|---|
| GRK6  | VPEGQ-TIKG | RVGTVGYMAP | EVVKNER-YT | FSPDWWALGC | LLYEMIAGQS | 382 |
| GRK5  | IPEGD-LIRG | RVGTVGYMAP | EVLNNQR-YG | LSPDYWGLGC | LIYEMIEGQS | 383 |
| IT-11 | IPEGQ-RVRG | RVGTVGYMAP | EVVNNEK-YT | FSPDWWGLGC | LIYEMIQGHS | 352 |
| RK    | LKAGQTKTKG | YAGTPGFMAP | ELLLGEE-YD | FSVDYFALGV | TLYEMIAARG | 387 |
| GPRK2 | IPEGE-MVRG | RVGTVGYMAP | EVIDNEK-YA | FSPDWFSFGC | LLYEMIEGQA | 220 |
| BARK1 | FSKK--KPHA | SVGTHGYMAP | EVLQKGVAYD | SSADWFSLGC | MLFKLLRGHS | 389 |
| BARK2 | FSKK--KPHA | SVGTHGYMAP | EVLQKGTCYD | SSADWFSLGC | MLFKLLRGHS | 389 |
| GPRK1 | FSKK--KPHA | SVGTHGYMAP | EVLSKGTSYD | SCADWFSFGC | MLYKLLKGHS | 390 |

FIGURE 1D

| | | | | | |
|---|---|---|---|---|---|
| GRK6  | PFQQRKKKIK | REEVERLVKE | VPEEYSERFS | PQARSLCSQL | LCKDPAER-- | 431 |
| GRK5  | PFRGRKEKVK | REEVDRRVLE | TEEVYSHKFS | EEAKSICKML | LTKDAKQR-- | 431 |
| IT-11 | PFKKYKEKVK | WEEVDQRIKN | DTEEYSEKFS | EDAKSICRML | LTKNPSKR-- | 400 |
| RK    | PFRARGEKVE | NKELKQRVLE | QAVTYPDKFS | PASKDFCEAL | LQKDPEKR-- | 435 |
| GPRK2 | PFRMRKEKVK | REEVDRRVKE | DPEKYSSKFN | DEAKSMCQQL | LAKSIKQR-- | 268 |
| BARK1 | PFRQHKTKDK | HE-IDRMTLT | MAVELPDSFS | PELRSLLEGL | LQRDVNRRLG | 438 |
| BARK2 | PFRQHKTKDK | HE-IDRMTLT | VNVQLPDAFS | PELRSLLEGL | LQRDVSQRLG | 438 |
| GPRK1 | PFRQHKTKDK | LE-IDKMTLT | MNVELPESFS | LELKNLLEML | LQRDVSKRLG | 439 |

| | | | | | |
|---|---|---|---|---|---|
| GRK6  | -L---GCRGG- | -SA--REVK- | ------EH | PL------ | --FK--KL | 451 |
| GRK5  | -L---GCQEE- | -GA--AEVK- | ------RH | PF------ | --FR--NM | 451 |
| IT-11 | -L---GCRGE- | -GA--AGVK- | ------QH | PV------ | --FK--DI | 420 |
| RK    | -L---GFRDG- | -SC--DGLR- | ------TH | PL------ | --FR--DI | 455 |
| GPRK2 | -L---GCRNGR | MGG--QDVM- | ------AH | PF------ | --FHSTQL | 292 |
| BARK1 | CLGRGAQEVK | ESPFFRSLDW | QMVFLQKYPP | PLIPPRGEVN | AADAFDIGSF | 488 |
| BARK2 | CYGGGARELK | EHIFFKGIDW | QYVYLRKYPP | PLIPPRGEVN | AADAFDIGSF | 488 |
| GPRK1 | CMGNGADEVK | MHNFFCGIDW | HQVYIQKYTP | PLVPPRGEVN | AADAFDIGSF | 489 |

FIGURE 1E

| | | | | | | |
|---|---|---|---|---|---|---|
| GRK6  | N-----FKR | LGAGM-LEPP | F---KPD--- | ---PQAIY-- | -CKDVLDIEQ | 482 |
| GRK5  | N-----FKR | LEAGM-LDPP | F---VPD--- | ---PRAVY-- | -CKDVLDIEQ | 482 |
| IT-11 | N-----FRR | LEANM-LEPP | F---CPD--- | ---PHAVY-- | -CKDVLDIEQ | 451 |
| RK    | S-----WRQ | LEAGM-LTPP | F---VPD--- | ---SRTVY-- | -AKNIQDVGA | 486 |
| GPRK2 | N-----WRR | LEAGM-LEPP | F---VPD--- | ---PHAVY-- | -AKDVLDIEQ | 323 |
| BARK1 | DEEDTKGIKL | LDSDQELYRN | FPLTISERWQ | QEVAETVFDT | INAETDRLEA | 538 |
| BARK2 | DEEDTKGIKL | LDCDQDLYKN | FPLMISERWQ | QEVVETIYDA | VNAETDKIEA | 538 |
| GPRK1 | DEEDTKGIKL | NDADQDLYKM | FSLTISERWQ | QEVSETVFDT | VNTETDKLEQ | 539 |

| | | | | | | |
|---|---|---|---|---|---|---|
| GRK6  | FSTVKGVELE | PTDQ------ | ----DFYQKF | ATGSVP---- | ------I | 509 |
| GRK5  | FSTVKGVNLD | HTDD------ | ----DFYSKF | STGSVS---- | ------I | 509 |
| IT-11 | FSAVKGIYLD | TADE------ | ----DFYARF | ATGCVS---- | ------I | 478 |
| RK    | FSTVKGVAFE | KADT------ | ----EFFQEF | ASGTCP---- | ------I | 513 |
| GPRK2 | FSTVKGVNID | ESDT------ | ----NFYTKF | NTGSVS---- | ------I | 350 |
| BARK1 | RKKAKNKQLG | HEEDYALGKD | CIMHGYMSKM | GNPFLTQWQR | RYFYLFPNRL | 588 |
| BARK2 | RKKAKNKQLC | QEEDYAMGKD | CIMHGYMLKL | GNPFLTQWQR | RYFYLFPNRL | 588 |
| GPRK1 | KRKLKQKQHF | DADE--KESD | CILHGYIKKL | GGSFASLWQT | KYAKLYPNRL | 587 |

FIGURE 1F

```
GRK6   PWQNE--MVE TE-CFQELN- --------- --------- -VFGLDGSV PPDLDWKGQP  543
GRK5   PWQNE--MIE TE-CFKELN- --------- --------- -VFGPNGTL PPDLNRNHPP  543
IT-11  PWQNE----- -D-C---LT- --------- --------- -M-VPSEK- -EVEPKQ-C   500
RK     PWQEE--MIE TGVFGD-LN- --------- --------- -VWRPDG-- -----P      538
GPRK2  SWQNE--MME TE-CFRELN- --------- --------- -------QM -----P      384
BARK1  EWRGEGEAPQ SLLTMEEIQS VEETQIKERK --------- -VFGPEECP TPDLQINAAP  638
BARK2  EWRGEGESRQ NLLTMEQIMS VEETQIKDRK --------- CLLLKIRGGK QFILQCDSDP  638
GPRK1  ELHSESGNNK PELIF--MDQ VED--I-SSD --------- CILLRVKGGK QFVLQCESDP  632
                                                  FILHKNENCI QIRINDGTRD

GRK6   P--------- --------- --------- ---APP KKGLL----Q RLFSR-QDCC   562
GRK5   E--------- --------- --------- ----PP KKGLL----Q RLFKR-QH--   559
IT-11  --------- --------- --------- ------ --------- --------    -
RK     D--------- --------- --------- -----D- MKGVS----G --------    546
GPRK2  E--------- --------- --------- ----PD- KAGCF----P --------    398
BARK1  ELVQWKKELR DAYREAQQLV QRVPKMKNKP RSPVVELSKV PLVQRGSA--          686
BARK2  EFAQWLKELT CTFNEAQRLL RRAPKFLNKP RAAILEFSKP PLCHRNSSGL          688
GPRK1  GRIILTNSDE IGLKEWSSSL RSAHKISQDL LGSMAK-KAG KIYGSERD--          679
```

FIGURE 1G

| | | | | |
|---|---|---|---|---|
| GRK6 | GNCSDSEEEL | PTRL------ | ---------- | 576 |
| GRK5 | --QNNSKSS | PSSKTSFNHH | INSNHVSSNS TGSS---- | 590 |
| IT-11 | ---------- | ---------- | ---------- | - |
| RK | ---QEAAPSS | KSGMCVLS-- | ---------- | 561 |
| GPRK2 | ---KQPARTQ | PIPIPEHLLT | THSVSSTTVE S------- | 426 |
| BARK1 | ------NGL- | ---------- | ---------- | 689 |
| BARK2 | ---------- | ---------- | ---------- | - |
| GPRK1 | ---VNKSM-- | IFGGNCSTKT | SNGSN----- | 699 |

FIGURE 1H

G PROTEIN-COUPLED RECEPTOR KINASE GRK6

This application is a continuation-in-part of U.S. patent application Ser. No. 08/123,932 filed on Sep. 17, 1993 now abandoned.

FIELD OF THE INVENTION

The present invention relates generally to a novel G protein-coupled receptor kinase designated GRK6 and more particularly to purified and isolated polynucleotides encoding GRK6, to methods and materials for recombinant production of GRK6 enzyme and to methods of identifying modulators of GRK6 kinase activity.

BACKGROUND

Serpentine or seven transmembrane receptors mediate signals for a wide variety of stimuli, including neurotransmitters, hormones, chemoattractants, odorants, and light [Dohlman et al., *Ann. Rev. Biochem.*, 60: 653–688 (1991); Probst et al., *DNA and Cell Biol.*, 11: 1–20 (1992)]. These receptors share several common structural features, including an extracellular amino terminus, seven transmembrane spanning domains, and a cytoplasmic carboxy terminus with clustered serine and threonine residues. More than 100 members of this superfamily of receptors have been identified. These receptors are coupled to intracellular signal transduction pathways by heterotrimeric GTP-binding proteins (G proteins) [Linder et al., *Sci. Am.*, 267: 56–65 (1992)].

Two G protein-coupled signal transduction mechanisms have been especially well characterized: the hormone responsive $\beta_2$-adrenergic receptor mediates catecholamine stimulation of adenyl cyclase [Dohlman et al., supra] and the light receptor rhodopsin mediates phototransduction in retinal rod cells [Khorana, *J. Biol. Chem.*, 267: 1–4 (1992)]. Both receptors specifically interact with G proteins following activation by ligand. This receptor stimulation is tightly regulated such that interaction with ligand leads to a rapid and reversible loss of responsiveness of the receptor to subsequent stimulation. The process is termed homologous desensitization and is caused by phosphorylation of the receptor, usually on a cluster of serines and threonines present at the carboxy terminus [Lefkowitz, *Cell*, 74: 409–412 (1993)]. Such phosphorylation is mediated by specific protein kinases which recognize the ligand-occupied receptor [Palczewski et al., *Trends Biochem. Sci.*, 16: 387–391 (1991)]. The 62 adrenergic receptor kinase ($\beta$ARK1) and rhodopsin kinase (RK) have been shown to phosphorylate the activated forms of the $\beta$-adrenergic receptor and rhodopsin, respectively. Both proteins have been purified and enzymatically characterized in reconstituted in vitro systems.

Additional lines of evidence suggest that other G protein-coupled receptors may be regulated by specific kinases. Receptor phosphorylation has been shown to be involved in desensitization in a variety of G protein-coupled systems ranging from mammalian cells [such as muscarinic cholinergic receptors, Kwatra et al., *J. Biol. Chem.*, 262: 16314–16321 (1987)] to slime mold [the chemotactic cAMP receptor, Klein et al., *J. Cell Biol.*, 100: 715–720 (1985)] and yeast [the mating factor α receptor, Reneke et al., *Cell*, 55: 221–234 (1988)]. In addition, the carboxy terminal domain of most G protein-coupled receptors contains potential phosphorylation sites which may represent catalytic targets for such kinases.

Lorenz et al., *Proc. Natl. Acad. Sci.*, 88: 8715–8719 (1991) compares the deduced amino acid sequences of human $\beta$ARK1 [Benovic et al., *Science*, 246: 235–240 (1989)] and bovine RK and suggests that the two molecules are structurally related. While in principle these two protein kinases could be responsible for the desensitization of the whole family of G protein-coupled receptors, recent identification of other structurally related protein kinases suggests that this is not the case. Sequences encoding three other mammalian G protein-coupled receptor kinases (GRKs) have recently been cloned, rat $\beta$ARK2 [Benovic et al., *J. Biol. Chem.*, 266: 14939–14946 (1991)], human IT-11 [Ambrose et al., *Hum. Mol. Genet.*, 1: 697–703 (1992)] and human GRK5 [Kunapuli et al., *Proc. Natl. Acad. Sci.* USA, 90: 5588–5592 (1993)], as well as sequences encoding two Drosophila GRKs (GPRK-1 and GPRK-2) [Cassill et al., *Proc. Natl. Acad. Sci.* USA, 88: 11067–11070 (1991)]. The GRK family has recently been the subject of the review article Lefkowitz, supra. All of the GRKs share the highest structural homology in the centrally located catalytic domain of approximately 250 amino acids. The amino and carboxyl regions surrounding the catalytic domain are less homologous and may confer substrate specificity and subcellular localization, respectively. The GRKs are expressed in a tissue specific manner, which may further aid in the regulation of G protein-coupled signal transduction events.

G protein-coupled receptor kinases that are expressed in leukocytic cells and tissues are likely to aid the function and activities of G protein-coupled receptors expressed in these cells. Consequently, such kinases are likely to be important mediator molecules in the immune system. For example, receptors for a number of chemoattractants including fMetLeuPhe [Thomas et al., *J. Biol. Chem.*, 265: 20061–20064 (1990)] and C5a [Gerard et al., *Nature*, 349: 614–617 (1991)] and for the chemokines IL-8 [Holmes et al., *Science*, 253: 1278–1280 (1991)], GRO [Murphy et al., *Science*, 253: 1280–1283 (1991)] and MIP 1α RANTES [Neote et al., *Cell*, 72: 415–425 (1993)] have recently been identified as members of the G protein-coupled receptor superfamily. This suggests that modulation of G protein-coupled receptor kinase activity may influence health and disease states of the immune system in acute and chronic inflammation.

There thus exists a need in the art to identify G protein-coupled receptor kinases that are expressed in cells and tissues of the immune system. Elucidation of the DNA and amino acid sequences encoding such a kinase would provide information and material to allow the development of novel agents that selectively modulate the activity of the protein kinase.

SUMMARY OF THE INVENTION

The present invention provides novel purified and isolated polynucleotides (i.e., DNA and RNA, both sense and antisense strands) encoding the G protein-coupled receptor kinase designated GRK6. Preferred DNA sequences of the invention include genomic and cDNA sequences as well as wholly or partially chemically synthesized DNA sequences. The DNA sequence encoding GRK6 that is set out in SEQ ID NO: 12 and DNA sequences which hybridize to the noncoding strand thereof under stringent conditions or which would hybridize but for the redundancy of the genetic code, are contemplated by the invention. Also contemplated by the invention are biological replicas (i.e., copies of isolated DNA sequences made in vivo or in vitro) of DNA sequences of the invention. Presently preferred DNA sequences of the invention are the human GRK6 cDNA sequence set out in SEQ ID NO: 12 and the rat GRK6 cDNA sequence set out in SEQ ID NO: 21, which were respectivley deposited with the American Type Culture Collection (ATCC), 12301 Parklawn Drive, Rockville, Md. 20852, on Mar. 24, 1994 as inserts in plasmids pλ22 and pB24 which were assigned ATCC Accession Nos. 69594 and 69595. Autonomously replicating recombinant constructions such as plasmid and viral DNA vectors incorporating GRK6 sequences and especially vectors wherein DNA encoding GRK6 is operatively linked to an endogenous or exogenous expression control DNA sequence and a transcription terminator are also provided.

According to another aspect of the invention, host cells including procaryotic and eucaryotic cells, are stably transformed with DNA sequences of the invention in a manner allowing the desired GRK6 enzyme to be expressed therein. Host cells expressing GRK6 products can serve a variety of useful purposes. Such cells constitute a valuable source of immunogen for the development of antibody substances specifically immunoreactive with GRK6. Host cells of the invention are conspicuously useful in methods for the large scale production of GRK6 enzyme wherein the cells are grown in a suitable culture medium and the desired polypeptide products are isolated from the cells or from the medium in which the cells are grown by, for example, immunoaffinity purification.

GRK6 products may be obtained as isolates from natural cell sources or may be chemically synthesized, but are preferably produced by recombinant procedures involving host cells of the invention. GRK6 products having part or all of the amino acid sequence set out in SEQ ID NO: 13 are contemplated. Use of mammalian host cells is expected to provide for such post-translational modifications (e.g., myristolation, glycosylation, truncation, lipidation and tyrosine, serine or threonine phosphorylation) as may be needed to confer optimal biological activity on recombinant expression products of the invention. GRK6 products of the invention may be full length polypeptides, fragments or variants. Variants may comprise GRK6 analogs wherein one or more of the specified (i.e., naturally encoded) amino acids is deleted or replaced or wherein one or more nonspecified amino acids are added: (1) without loss of one or more of the kinase activities or immunological characteristics specific to GRK6; or (2) with specific disablement of a particular biological activity of GRK6.

Also comprehended by the present invention are antibody substances (e.g., monoclonal and polyclonal antibodies, single chain antibodies, chimeric antibodies, CDR-grafted antibodies and the like) and other binding proteins specific for GRK6. Specific binding proteins can be developed using isolated or recombinant GRK6 or GRK6 variants or cells expressing such products. Binding proteins are useful, in turn, in compositions for immunization as well as for purifying GRK6 polypeptides and detection or quantification of GRK6 enzyme in fluid and tissue samples by known immunogical procedures. They are also manifestly useful in modulating (i.e., blocking, inhibiting or stimulating) enzymatic activities of GRK6, especially those activities involved in signal transduction. Anti-idiotypic antibodies specific for anti-GRK6 antibody substances are also contemplated.

The scientific value of the information contributed through the disclosures of DNA and amino acid sequences of the present invention is manifest. As one series of examples, knowledge of the sequence of a cDNA for GRK6 makes possible the isolation by DNA/DNA hybridization of genomic DNA sequences encoding GRK6 and specifying GRK6 expression control regulatory sequences such as promoters, operators and the like. DNA/DNA hybridization procedures carded out with DNA sequences of the invention under stringent conditions are likewise expected to allow the isolation of DNAs encoding allelic variants of GRK6, other structurally related proteins sharing one or more of the biochemical and/or immunological properties specific to GRK6, and non-human species proteins homologous to GRK6. Polynucleotides of the invention when suitably labelled are useful in hybridization assays to detect the capacity of cells to synthesize GRK6. Polynucleotides of the invention may also be the basis for diagnostic methods useful for identifying a genetic alteration(s) in the GRK6 locus that underlies a disease state or states. Also made available by the invention are anti-sense polynucleotides relevant to regulating expression of GRK6 by those cells which ordinarily express the same.

The DNA and amino acid sequence information provided by the present invention also makes possible the systematic analysis of the structure and function of GRK6 and definition of those molecules with which it will interact. Agents that modulate GRK6 activity may be identified by incubating a putative modulator with lysate from procaryotic or eucaryotic host cells expressing recombinant GRK6 and determining the effect of the putative modulator on GRK6 kinase activity. In a preferred embodiment the host cells lack endogenous GRK6 kinase activity. For example, *E. coli* is known to lack serine/threonine kinase activity. The selectivity of a compound that modulates the activity of GRK6 can be evaluated by comparing its activity on the GRK6 to its activity on other G protein-coupled receptor kinases. The combination of the recombinant GRK6 products of the invention with other recombinant G protein-coupled receptor kinase products in a series of independent assays provides a system for developing selective modulators of GRK6.

Selective modulators may include, for example, polypeptides or peptides which specifically bind to GRK6 or GRK6 nucleic acid, oligonucleotides which specifically bind to GRK6 or GRK6 nucleic acid and other non-peptide compounds (e.g., isolated or synthetic organic molecules) which specifically react with GRK6 or GRK6 nucleic acid. Mutant forms of GRK6 which affect the enzymatic activity or cellular localization of the wild-type protein kinase are also contemplated by the invention. Presently preferred regions of GRK6 which are targets for the development of selective modulators include, for example, the amino terminus of the enzyme (residues 1–179 of SEQ ID NO: 13) and the carboxy terminus of the enzyme (residues 452–576 of SEQ ID NO: 13). Modulators of GRK6 activity may be therapeutically useful in treatment of diseases and physiological conditions of the immune system.

BRIEF DESCRIPTION OF THE DRAWINGS

Numerous other aspects and advantages of the present invention will be apparent upon consideration of the following detailed description thereof, reference being made to the drawing wherein:

FIG. 1A to 1H is an alignment of the full length amino acid sequence of the novel human protein kinase GRK-6 with the full length sequences of previously identified protein kinases human GRK5, human IT-11, bovine RK, Drosophila GPRK-2, human βARK1, rat βARK2 and Drosophila GPRK-1.

DETAILED DESCRIPTION

Figure 2:
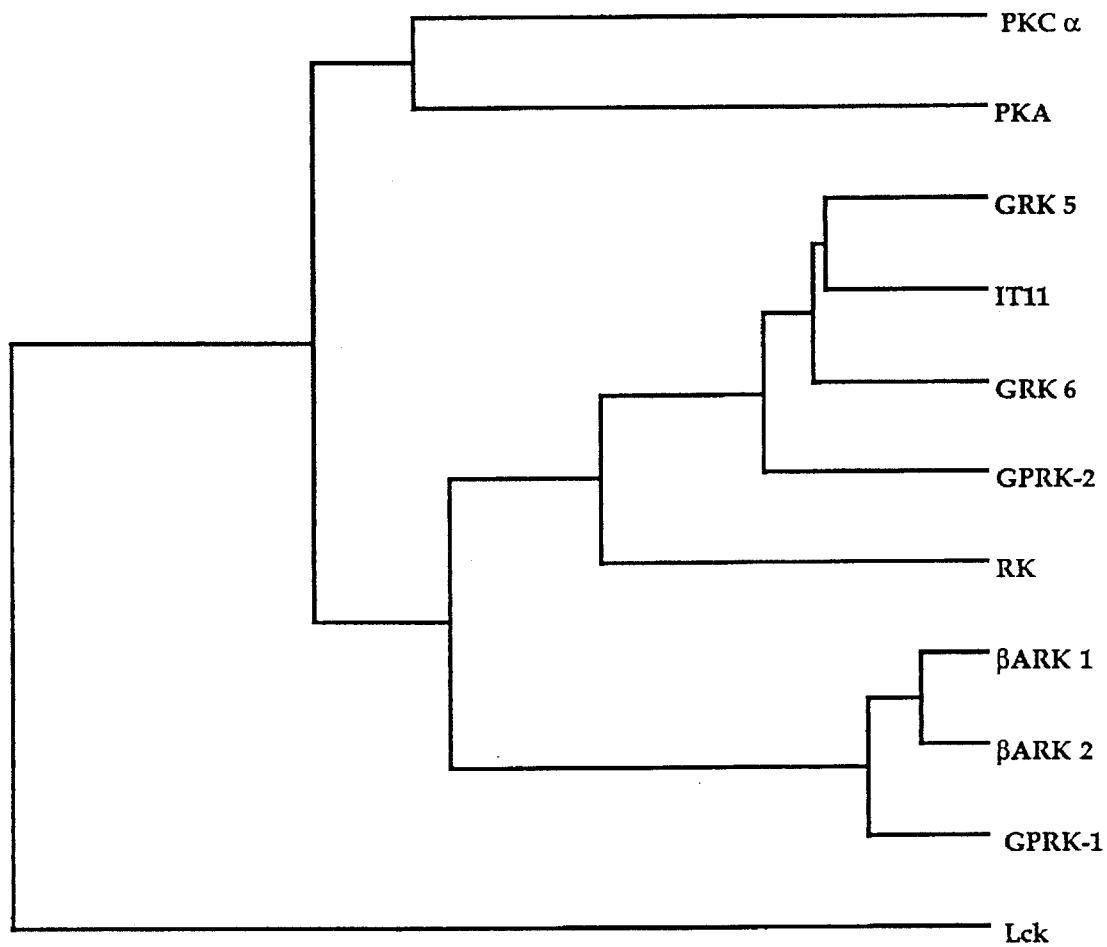
FIG. 2 is a diagram representing the evolutionary relatedness of the GRK family in comparison to two cytoplasmic serine/threonine kinases (PKC-α and PKA) and one tyrosine kinase (Lck) as determined by dendogram analysis.

The following examples illustrate the invention. Example 1 describes the isolation of a rat GRK6 cDNA fragment by PCR, the subsequent isolation of GRK6 cDNA-containing pools of human macrophage cDNAs and of a partial human GRK6 macrophage cDNA by colony hybridzation, and the isolation of a complete coding sequence for GRK6 from human placental cDNA. Example 2 characterizes the GRK6 DNA and amino acid sequences and presents a comparison of the sequences to those of previously defined GRKs. Example 3 describes the isolation of a full length rat GRK6 cDNA. Example 4 describes the construction of a vector for the bacterial expression of GRK6 and describes an assay showing that the GRK6 recombinant product has kinase activity. Example 5 relates to Northern blot assays showing the expression of GRK6 mRNA predominantly in lymphoid tissues and cell lines. Example 6 describes the down-regulation of GRK6 mRNA production in hematopoietic cell lines during differentiation. Example 7 relates to utilizing recombinant GRK6 products of the invention to develop agents that selectively modulate the enzymatic actvities of GRK6.

EXAMPLE 1

To isolate a novel GRK, degenerate oligonucleotide primers were designed for use in a PCR reaction based on sequences conserved in the catalytic domain of RK and βARK1 (Lorenz et al., supra). βARK1 and RK share significant protein homology in the putative catalytic domain (42%) which has been determined to have twelve structural subdomains [Hanks et al. *Meth. Enzymol.*, 200: 38–62 (1991)]. Degenerate oligonucleotide primers were designed based on two of the most highly conserved amino acid regions present in subdomains II and VII. The sense primer designed is set out below in IUPAC nomemclature:

5' ATTGGATCCGCACH GGV AAR MTS TAY GCN TGY
AAR 3'   SEQ ID NO: 1 and encodes a BamHI site (underlined) and the amino acid sequence TGKLYA (SEQ ID NO: 2) or TGKMYA (SEQ ID NO: 3). The anti-sense primer is set out below in IUPAC nomenclature:

5' ATTTCTAGADGC VAG ICC VAG RTC IGA
DAT NCG NA 3'   SEQ ID NO: 4 and encodes a XbaI site and the amino acid sequence VRISDLGLA (SEQ ID NO: 5).

The primers were utilized in a PCR reaction with rat T cell cDNA as template. PCR reactions consisted of about 100 ng of cDNA template, 10 µg/ml oligonucleotide primers, 50 mM KCl, 10 mM Tris HCl (pH 8.4), 1.5 mM MgCl$_2$, 200 mM dNTPs and 1 unit of Taq polymerase in a final volume of 100 µl. Reactions were heated for 7 minutes at 95° C. followed by 30 cycles of denaturation of 1 minute at 95° C., annealing for 2 minutes at 55° C. and extension for 4 minutes at 72° C. Amplified products were purified using the Magic PCR prep kit (Promega, Madison, Wis.) according to the manufacturer's instructions, digested with BamHI and XbaI, and cloned into pBluescript (SK+) (Invitrogen, San Diego, Calif.). Because the expression of βARK1 has previously been observed in leukocytic cells, PCR clones were screened by hybridization using an end-labelled oligonucleotide probe specific for βARK1:

5'TCG CTC GTC AGC ACT GGG GAC TGC
CCA 3'   SEQ ID NO: 6 and non-hybridizing clones were chosen for sequencing. Sequencing was performed on double stranded templates using a sequenase kit (USB, Cleveland, Ohio) according to the manufacturer's instructions. Eight non-hybridizing clones were determined to contain a PCR product of a size consistent with GRK subdomain sequences and three of eight sequences corresponded to a single novel structure with homology to other previously identified GRKs. The five other non-hybridizing sequences did not appear to encode protein kinases.

A human macrophage cDNA library was constructed by standard methods in the mammalian expression vector pRc-CMV (Invitrogen). The partial rat GRK sequence (set out in SEQ ID NO: 7) was used to design oligonucleotides for PCR amplification of a human homologue of the novel GRK from the library. The sense primer encoded a BamHI site to facilitate cloning and was:

5'ATTGGATCC ATG CGG ACG TGG CCG TGG
TCA AG 3'   SEQ ID NO: 8

The antisense primer utilized encoded a XbaI site to facilitate cloning and was:

5'ATTTCTAGA ATG CGG ACG TGG CCG TGG
TCA AG 3'   SEQ ID NO: 9

Successive rounds of PCR were performed as described above, initially to identify a pool of 100,000 positive clones and subsequently to identify a sub-pool of 1000 positive clones. A single clone termed 504.3 was isolated from the sub-pool by colony hybridization using the rat PCR product labelled by random priming as a probe. The partial human macrophage cDNA clone encoded the same amino acid sequence as the cloned rat PCR fragment and was later determined to correspond to amino acids 236 to 332 of the human protein.

To isolate a full length human cDNA clone, the partial macrophage cDNA clone 504.3 was used to screen by hybridization ~1×10$^6$ clones from a human placenta cDNA library made in λgt 10 by standard methods. Hybridization was performed for 16 hours at 42° C. in buffer containing 50% formamide, 5×SSC, 5×Denhardts, 0.05M Na phosphate, and 100 µg/ml salmon sperm DNA. Filters were washed in 0.2×SCC/0.1% SDS at 50° C. Five clones were subsequently isolated and sub-cloned into pBluescript (SK-) (Invitrogen). Sequencing was performed using specific primers on double-stranded templates as described above. Each clone was sequenced on both strands at least once. One full length clone was identified (pλ22, ATCC 69594) and the protein encoded by its insert was named GRK6. The DNA and deduced amino acid sequences of GRK6 as originally determined are set out in SEQ ID NOs: 10 and 11. Further sequence analysis of the GRK6 insert resulted in the DNA and deduced amino acid sequences set out in SEQ ID NOs: 12 and 13, respectively. Benovic et al., *J. Biol. Chem.*, 268(26): 19521–19527 (September 1993) reports the isolation of a human heart cDNA encoding a G protein-coupled receptor kinase which was also named GRK6. The predicted amino acid sequence of the Benovic GRK6 clone differs at one position (corresponding to position 61 of SEQ ID NO: 13) from SEQ ID NO: 13 when the sequences are aligned. Haribabu et al., *Proc. Natl. Acad. Sci.* USA, 90: 9398–9402 (October 1993) describes the isolation of three G protein- Northern blots (see Example 5). The protein sequence of GRK6 contains a centrally located protein kinase catalytic domain of 272 residues (residues 180 to 451 of SEQ ID NO: 13) which is flanked by an amino terminal domain of about 179 residues and a carboxy terminal domain of 96 residues.

A comparison of the amino acid sequence of the putative catalytic domain of GRK6 with sequences of the catalytic domains of other GRKs, the more distantly related tyrosine kinase Lck [Koga et al., *Eur. J. Immunol.*, 16: 1643–1646 (1986)], and the unrelated serine/threonine kinases PKA [Maldonado et al., *Nuc. Acids Res.*, 16: 8189–8190 (1988)] and PKCα [Parker et al., *Science*, 233: 853–859 (1986)] was performed using the Geneworks program (Mountain View, Calif.). Results of the comparison are set out in Table 1 below as percentages of amino acid identity.

TABLE 1

|        | IT-11 | GRK5 | GPRK-2 | RK | βARK1 | βARK2 | GPRK-1 | PKA | PKCα | Lck |
|--------|-------|------|--------|----|-------|-------|--------|-----|------|-----|
| GRK6   | 77    | 75   | 69     | 56 | 49    | 48    | 47     | 35  | 36   | 15  |
| IT-11  |       | 79   | 70     | 56 | 46    | 45    | 47     | 35  | 38   | 16  |
| GRK5   |       |      | 74     | 56 | 48    | 47    | 47     | 34  | 38   | 10  |
| GPRK-2 |       |      |        | 52 | 45    | 43    | 45     | 32  | 37   | 23  |
| RK     |       |      |        |    | 42    | 42    | 41     | 37  | 39   | 21  |
| βARK1  |       |      |        |    |       | 90    | 83     | 34  | 33   | 19  |
| βARK2  |       |      |        |    |       |       | 83     | 34  | 33   | 21  |
| GPRK-1 |       |      |        |    |       |       |        | 33  | 33   | 22  |
| PKA    |       |      |        |    |       |       |        |     | 40   | 18  |
| PKCα   |       |      |        |    |       |       |        |     |      | 25  | coupled receptor kinase-like clones. The deduced amino acid sequence of one clone (GPRK6) lacks the thirty-three amino terminal amino acids of SEQ ID NO: 13 and differs at four positions (corresponding to positions 60, 61,104 and 105 of SEQ ID NO: 13) from SEQ ID NO: 13 when the sequences are aligned. Adams et al., *Nature*, 355: 632–634 (1992) reports the deposit of the sequence of an "expressed sequence tag" (EST 00538) in the EMBL nucleotide database. The 370-nucleotide EST corresponds to nucleotides 1 to 370 of SEQ ID NO: 12 but differs from SEQ ID NO: 12 at twelve positions when the sequences are aligned. The twelve differences include eight unidentified nucleotides in the EST and four nucleotides which are insertions or deletions made apparent by alignment of the sequences.

EXAMPLE 2

The open reading frame of the full length human cDNA GRK6 clone (SEQ ID NO: 12) encodes a protein of 576 amino acids, with a predicted molecular mass of 63.3 kDa. Upstream of the potential ATG initiation codon are 30' residues of 5' untranslated sequence which are typically G-C rich. The sequence surrounding this ATG is not optimal for translation initiation [Kozak, *J. Cell. Biol.*, 115: 887–903 (1991)] since it contains a cysteine at the −3 position instead of an adenine or guanine. Nevertheless, this ATG is likely to be the GRK6 initiating methionine residue because (1) the other surrounding residues abide by the Kozak consensus; (2) homology comparisons with other GRKs suggest that it is the appropriate start position; and (3) GRK5 also has a similar unusual Kozak sequence with a thymine at position −3 (Kunapuli et al., supra). The 3' untranslated region of GRK6 is approximately 1000 bases in length (only a portion of the 3' untranslated region is presented in SEQ ID NO: 12). The overall length of the cDNA (~3000 bp) corresponds well to the observed size of hybridizing message seen on The GRK6 catalytic domain is most similar to the catalytic domains of protein kinases IT-11 and GRK5.

A alignment of the full length amino acid sequence of the human GRK6 clone (SEQ ID NO: 13) and the full length amino acid sequences of human GRK5 (SEQ ID NO: 14), human IT-11 (SEQ ID NO: 15), bovine RK (SEQ ID NO: 16), Drosophila GPRK-2 (SEQ ID NO: 17), human βARK1 (SEQ ID NO: 18), rat βARK2 (SEQ ID NO: 19) and Drosophila GPRK-1 (SEQ ID NO: 20) is presented in FIG. 1A to 1H. The alignment and the phylogenetic tree depicted in FIG. 2 demonstrate that GRK5, GRK6, IT-11, and GPRK-2 form a distinct branch of the GRK family that is more similar to rhodopsin kinase than to βARK1, βARK2, and GPRK-1. The regions flanking the GRK6 catalytic domain are much less similar to other GRK sequences than the GRK6 catalytic domain itself and contain numerous insertions and deletions (for example, the Drosophila GPRK-2 has a very short amino terminal domain compared to GRK6). The function of these flanking domains is not known with certainty, but they may be involved with intracellular localization, association with the cellular membrane, interaction with G protein subunits, or confer substrate specificity. For example, RK contains a functional CAAX box at its carboxy terminus which is thought to mediate its association with the plasma membrane [Inglese et al., *J. Biol. Chem.*, 267: 1422–1425 (1992)] . GRK6 lacks this sequence but does contain two potential sites for myristolation at its amino terminus which may provide a similar membrane associative function. In addition, antibodies to the amino terminus of RK block its association with rhodopsin, suggesting that this portion of the protein may be important in targeting the protein kinase to its substrate(s) [Palczewski et al., *J. Biol. Chem.*, 268: 6004–6013 (1993)].

EXAMPLE 3

A full length GRK6 clone was isolated from a rat thymus library using the original PCR fragment (see Example 1)

amplified from rat T cell cDNA.

The rat PCR fragment was labelled by random priming and was initially used to screen approximately 1×10⁶ clones from a rat placental library in λgt10. Screening conditions identical to those desribed in Example 2 for isolation of the full length human GRK6 clone were utilized. Seven rat clones were identified, the longest of which (λ1) had a 1.4 kb insert. This clone was then used to screen an oligo dt primed cDNA library in λgt10 made from the rat T cell line BP3 [Bouwer et al., *Cellular Immunol.*, 131: 219–231 (1990)]. Screening of about 1×10⁶ clones from this library yielded seven new clones, the longest of which (λ2) was not full length. The λ2 clone was then used to screen approximately 1×10⁶ clones from a second library made from BP3 that was both oligo dt and random primed. A clone obtained from this screening (λ4) extended the 5' sequence of rat GRK6 by 450 nucleotides but still lacked 5' sequences. Next, this clone was used to screen a rat spleen cDNA library in λgt10 (Clontech, Palo Alto, Calif.). Five clones were isolated from this library but were not pursued since preliminary PCR analysis indicated that they also were incomplete. The λ4 clone was finally used to screen a rat thymus cDNA library in λZAP (Stratagene, La Jolla, Calif.). Screening of approximately 1×10⁶ clones from this library yielded eleven positives, one of which (clone pB24, ATCC 69595) contained the complete coding sequence of rat GRK6. The nucleotide and deduced amino acid sequences of the insert of clone B24 are set out in SEQ ID NOs: 21 and 22. The rat and human GRK6 sequences exhibit 95% identity at the amino acid level.

EXAMPLE 4

Based on its structural similarity to other members of the GRK family, GRK-6 was predicted to encode a functional protein kinase. To determine whether this was indeed the case, the putative GRK6 catalytic domain (residues 180 to 451 of SEQ ID NO: 13) was engineered for expression in *E. coli* as a fusion protein with thioredoxin in a vector similar to pTRXFUS described in LeVallie et al., *Biotechnology*, 11: 187–193 (1993). Specifically, human GRK6 catalytic domain coding sequences were amplified by PCR from the Bluescript placental clone described in Example 1. The sense primer utilized encoded a XbaI site (underlined) to facilitate cloning and was:

```
5' ATTTCTAGAATTCGTTTCCTGCAGTGGAA
        GTGG 3'                    SEQ ID NO: 23
``` and the antisense primer utilized encoded a HindIII site to facilitate cloning and six histidine residues to facilitate purification of the fusion protein when it is expressed and was:

```
SEQ ID NO: 24
5' ATTAAGCTTTTAGTGATGGTGATGG
    TGATGCGGCTCCAGCATGCCAGC 3'
```

Figure 3:
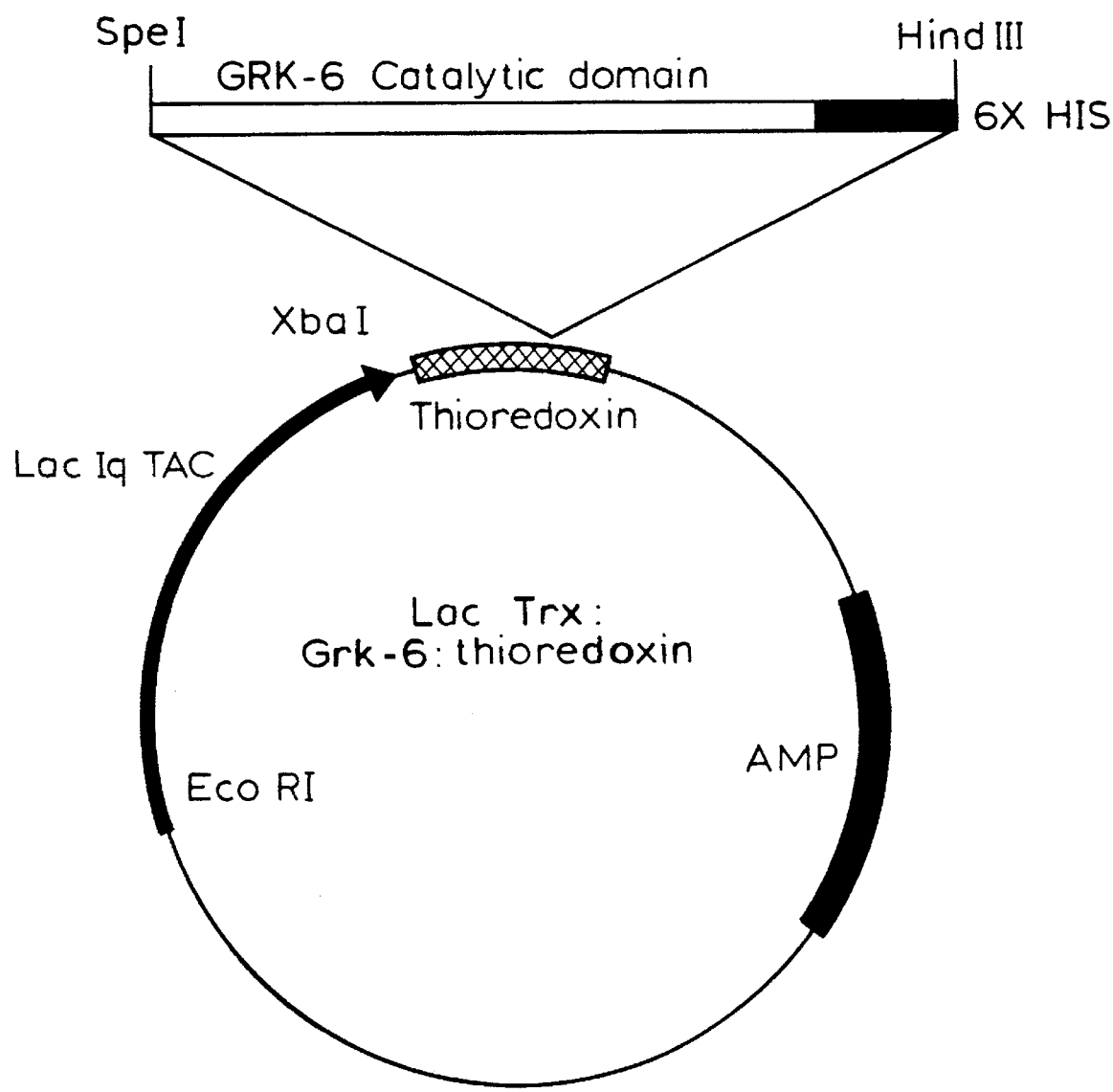
FIG. 3 is a diagram of a vector constructed for expression of GRK6 in *E. coli* as a fusion protein with thioredoxin

Digestion of the resulting PCR fragments with XbaI and HindIII allowed the fragment to be directionally cloned in frame at the carboxy terminal end of sequences encoding thioredoxin. The resulting expression vector contains the lac Iq gene, followed by the tacII promoter (from plasmid pMal-c2, New England Biolabs, Beverly, Mass.) which drives the expression of *E. coli* thioredoxin fused at the amino terminal end of the GRK6 catalytic domain. A schematic diagram of the expression vector is presented in FIG. 3.

*E. coli* XL-1 Blue cells (Stratagene, La Jolla, Calif.) were transformed with the expression vector. Transformed cells were grown at 37° C. to mid-log phase, samples were collected (to serve as controls for the induced cells) and the remaining cells induced for 2 hours with 0.4 mM IPTG at 30° C. Following induction with IPTG, soluble extracts from the clarified lysates were taken and an in vitro kinase assay was performed. Cell pellets were washed with PBS, frozen, thawed and resuspended with five times the volume of the cell pellet in kinase buffer (50 mM Tris pH 7.5, 100 mM NaCl, 12 mM MgCl₂ and 2.5 mM DTT) and sonicated until greater than 90% of the cells were lysed. Lysates were clarified by centrifugation and the supernatants collected. Ten μCi of λATP³²P was added to 9 μl of clarified lysate and the reaction was incubated for 10 minutes at 30° C. The reaction was terminated by addition of 2×SDS sample buffer and the lysates resolved by SDS-PAGE. The dried gel was exposed to Hyperfilm (Amersham, Arlington Heights, Ill.) for 16 hours at −80° C. with intensifying screens.

Figure 4:
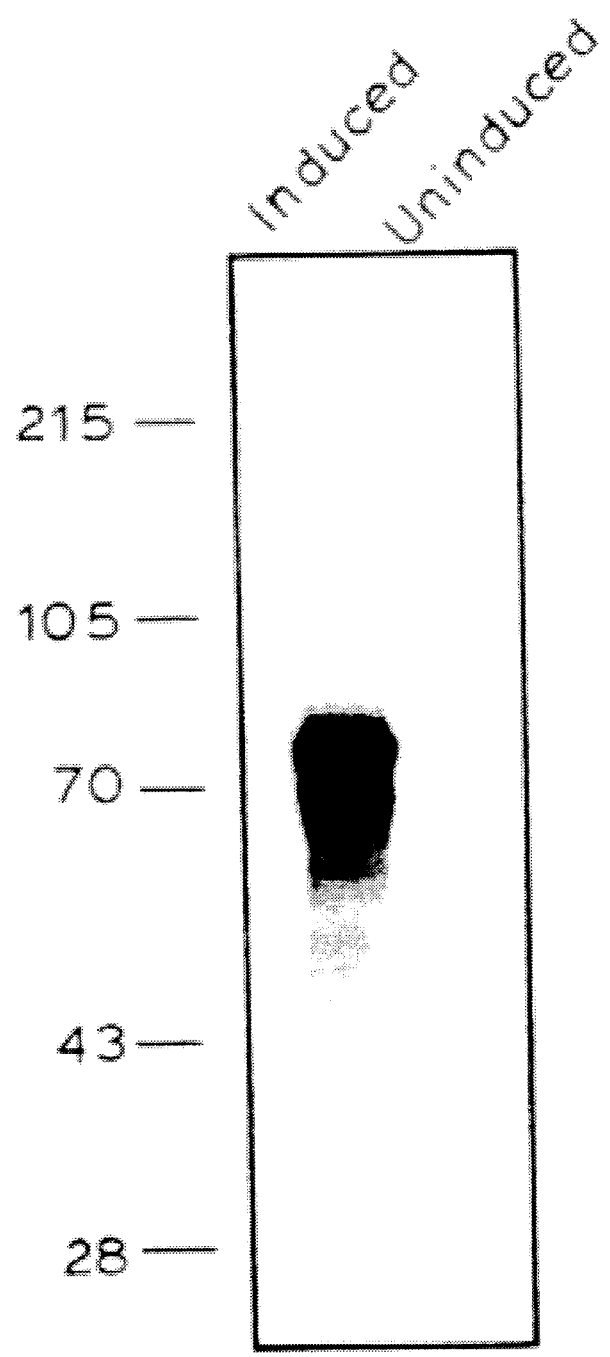
FIG. 4 is an autoradiogram showing GRK6 kinase activity in the soluble extract from *E. coli* cells in which GRK6 expression was induced but not in the soluble extract from control (uninduced) cells.

The recombinant protein including the GRK6 catalytic domain was found to phosphorylate *E. coli* proteins having a range of molecular weights (see FIG. 4) demonstrating that, in the absence of any mammalian accessory proteins, GRK6 encodes an enzymatically active protein kinase.

EXAMPLE 5

Northern blot analysis of total RNA from various human tissues indicates that GRK6 has a limited tissue distribution. Total RNA was extracted from human tissues (thymus, tonsil, brain, placenta, kidney, liver, and heart) and a number of hematopoietic cell lines (Daudi, Molt 3, H9, U937, THP-1 and HL60) using RNA Stat 60 (Tel-Test B Inc., Friendswood, Tex.) according to the manufacturer's instructions. Twenty μg of total RNA was fractionated on a 1.2% formaldehyde agarose gel and blotted onto nitrocellulose. Hybridizations using a DNA probe corresponding to amino acids 265 to 513 of SEQ ID NO: 13 were performed as described in Example 1 for isolation of the full length human GRK6 clone. Blots were washed to a final stringency of 0.2×SCC and 0.1% SDS at 50° C. and were then exposed to X-ray film at −80° C. with intensifying screens for 1–6 days. The blot was stripped and reprobed with a probe specific for glyceraldehyde 3-phosphate dehydrogenase to demonstrate the integrity of the RNA.

A single GRK6 transcript of ~3 kb was seen in human thymus and tonsil and at low levels in placenta, but not in human brain, heart, liver or kidney. In addition, GRK6 mRNA was detected in the human lymphoid and myeloid cell lines H9, MOLT3, Daudi, HL60, U937 and THP-1.

Figure 5:
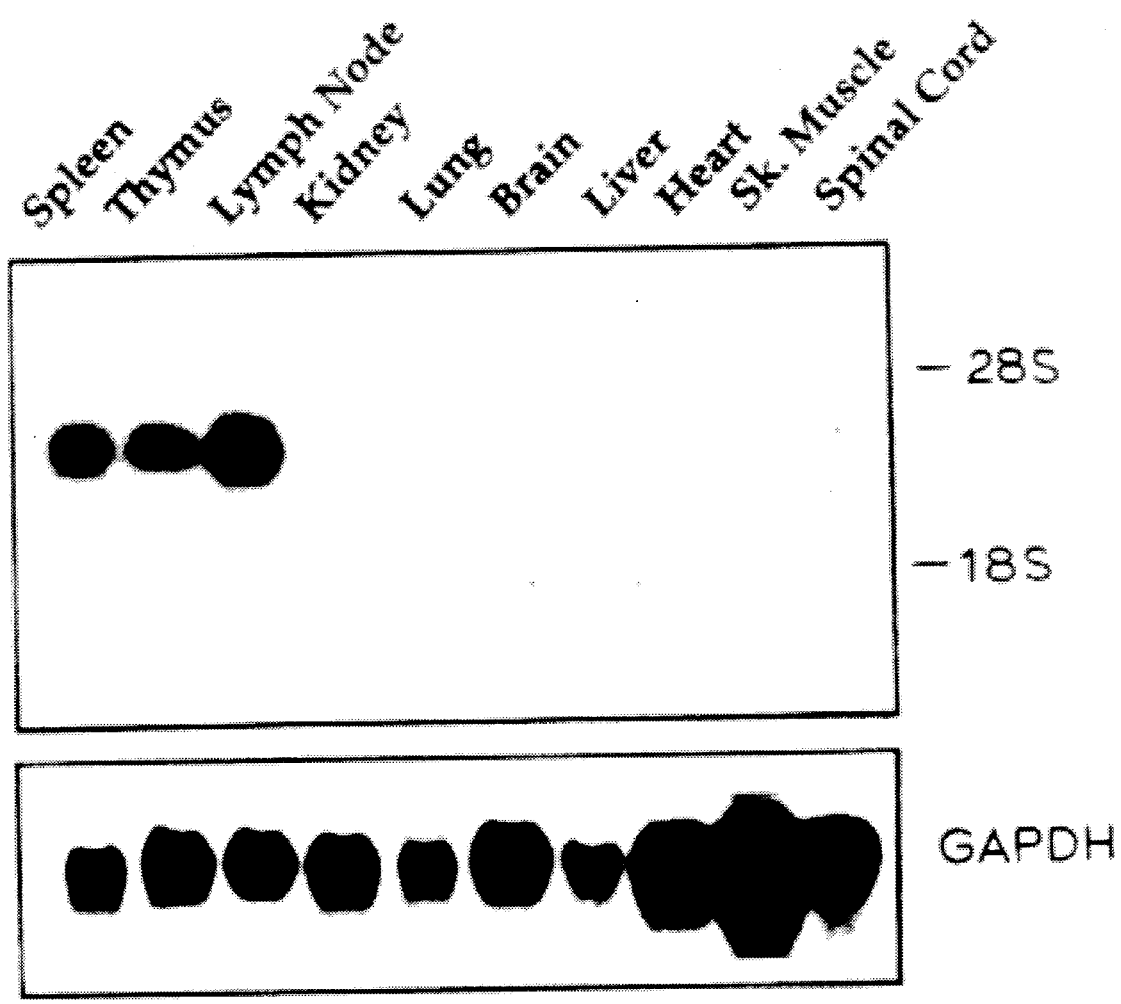
FIG. 5 is a Northern blot showing the predominant expression of GRK6 mRNA in lymphoid tissues in the rat.

Expression of GRK6 mRNA was also examined by Northern blot in rat tissues (spleen, thymus, lymph node, kidney, lung, brain, liver, heart, skeletal muscle and spinal cord). A probe corresponding to amino acids 300 to 576 of the full length rat clone (SEQ ID NO: 22) identified high levels of a single transcript of about 3 kb in spleen, thymus and lymph node. Much lower levels of expression of this transcript were also observed in non-lymphoid tissues (lung, brain, heart and spinal cord). See FIG. 5.

RK and the IT-11 gene product exhibit different, but also limited, tissue distributions. RK expression is confined to the retina and pineal gland (Lorenz et al., supra), while the IT-11 gene product (GRK4) is principally found in testis (Ambrose et al., supra). In contrast, the transcripts for GRK5, βARK1 and βARK2 show overlapping but distinctive patterns of expression in a wide range of tissues. GRK5 is expressed at the highest levels in heart, placenta and lung. It exhibits lower levels of expression in skeletal muscle, even lower levels in brain, liver and pancreas, and the lowest level of expression in kidney (Kanapuli et al., supra). βARK1 mRNA and βARK2 mRNA are found at the highest levels in nervous system tissue (e.g., cortex, hippocampus, cerebellum, brain stem and pituitary) and spleen followed by lower levels in lung, heart and kidney [Benovic et al. (1991), supra]. In most tissues βARK2 mRNA is only 10–20% of the level of βARK1 mRNA, but in the pituitary the mRNA levels are comparable.

The observation that GRKs can phosphorylate a wide range of G protein-coupled receptors in vitro raises questions concerning their substrate specificity. For example βARK1 has been shown to phosphorylate numerous receptors including the $\beta_2$-adrenergic receptor, the $\alpha_2$- adrenergic receptor and the m2 muscarinic cholinergic receptors. GRK5 can phosphorylate rhodopsin, while RK can phosphorylate both rhodopsin and the $\beta_2$ adrenergic receptor [Kunapuli et al., supra and Benovic et al., supra]. The physiological substrates of this family of kinases may be determined at least in part by their in vivo tissue localization. The restricted expression of GRK6 suggests that it may be involved in the regulation of signaling by those serpentine receptors expressed in the immune system.

EXAMPLE 6

A number of G protein-coupled receptors have been shown to be differentially expressed during hematopoiesis. For example, differentiation of the HL60 cell line along the granulocytic pathway leads to expression of the formyl peptide receptor and subsequent acquisition of responsiveness to this chemotactic peptide [Erbeck et al., *J. Immunol.*, 150: 1913–1921 (1993)]. To determine whether the expression of GRK6 is regulated during differentiation, a number of hematopoietic cell lines were examined.

Figure 6:
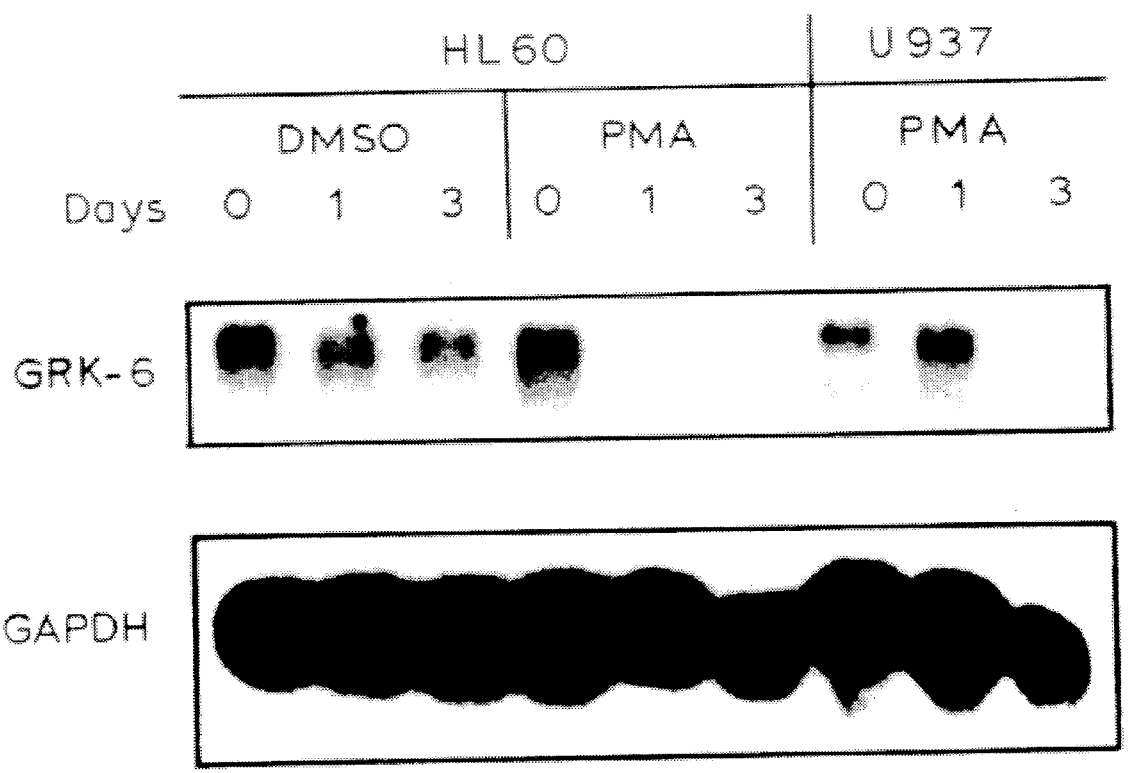
FIG. 6 is a Northern blot showing that the production of GRK6 mRNA is down-regulated during HL60 and U937 differentiation.

Differentiation of HL60 or U937 cells along the myeloid pathway by culture in the presence of 50 ng/ml phorbol ester leads to complete loss of expression of GRK6 mRNA as determined by Northern blotting of total cellular RNA (FIG. 6). In contrast, differentiation of HL-60 cells along the granulocytic pathway by culture in the presence of 1% DMSO does not appreciably change GRK6 mRNA levels. Thus down-regulation of GRK6 mRNA may be a direct response to differentiation along a particular cell lineage or may reflect a regulation of GRK6 expression by protein kinase C.

EXAMPLE 7

Developing modulators of the enzymatic activities of specific protein kinases requires differentiating the kinases present in a particular assay preparation. The classical enzymological approach of isolating protein kinases from natural tissue sources and studying each new kinase is hampered, however, by the limits of purification techniques and the inability to definitively assess whether complete resolution of a particular kinase has been achieved. One remedial approach involved identifying assay conditions which might favor the contribution of one protein kinase and minimize the contribution of others in a preparation. Still another approach has involved the separation of protein kinases by immunological means. The foregoing approaches for differentiating protein kinases are time consuming and technically difficult. As a result, many attempts to develop selective modulators of kinases have been performed with preparations containing more than one kinase. Moreover, protein kinase preparations from natural tissue sources are susceptible to limited proteolysis and may contain mixtures of active proteolytic products that have different kinetic, regulatory and physiological properties than the full length protein kinases.

Recombinant GRK6 products of the invention greatly facilitate the identification and characterization of specific GRK6 modulators. The use of human recombinant enzymes for screening for modulators has many inherent advantages. The need for purification of an protein kinase can be avoided by expressing it by recombinant methods in a host cell that has low levels or lacks endogenous GRK6 activity. Moreover, screening compounds against a recombinant human protein avoids the complicating prospect that often arises from screening against a non-human protein that a compound optimized on a non-human protein may fail to be specific for or react with the human protein. For example, a single amino acid difference between the human and rodent $5HT_{1B}$ serotonin receptors accounts for the difference in binding of a compound to the receptors. [See Oskenberg et al., *Nature*, 360: 161–163 (1992)]. Once a compound that modulates the activity of GRK6 is discovered, its selectivity can be evaluated by comparing its activity on the GRK6 enzyme to its activity on other kinases. Thus, the combination of the recombinant GRK6 products of the invention with other recombinant kinase products in a series of independent assays provides a system for identifying selective modulators of GRK6. Selective modulators are expected to include, for example, (1) antibodies and other proteins or peptides which specifically bind to GRK6 or GRK6 nucleic acid, (2) oligonucleotides which specifically bind to GRK6 (see Patent Cooperation Treaty International Publication No. WO93/05182 published Mar. 18, 1993 which describes methods for selecting oligonucleotides which selectively bind to target biomolecules) or GRK6 nucleic acid (e.g., antisense oligonucleotides) and (3) other non-peptide natural or synthetic compounds which specifically bind to GRK6 or GRK6 nucleic acid. Mutant forms of GRK6 which alter the enzymatic activity of GRK6 or its localization in a cell (e.g., dominant negative mutants) are also contemplated. For example, mutation of essential residues in the catalytic domain of GRK6 (e.g., lysine 215) are predicted to generate an enzymatically non-functional kinase. If over-expressed in a cell, such a mutant GRK6 may act as a dominant negative mutant by inhibiting the wild type enzyme by competing for substrate(s). Crystallization of recombinant GRK6 alone and bound to a modulator, analysis of atomic structure by X-ray crystallography, and computer modelling of those structures are methods useful for designing and optimizing non-peptide selective modulators. See, for example, Erickson et al., *Ann. Rev. Med. Chem.*, 27: 271–289 (1992) for a general review of structure-based drug design.

Regions of GRK6 that are expected to serve as targets for binding of modulators of GRK6 include, for example, the amino terminus of the enzyme (residues 1–179 of SEQ ID NO: 13), the carboxyl terminus of the enzyme (residues 452–576 of SEQ ID NO: 13) and the central catalytic domain (residues 180–451 of SEQ ID NO: 13). Antibodies to the amino terminus of RK inhibit its interaction with rhodopsin suggesting that this region of RK meidates its interaction with substrate (Palczewski et al., supra). Because the amino and carboxy terminus are the regions of the kinases in the GRK family that are very divergent, it is likely that modulators that target within these regions of GRK6 will specifically modulate GRK6 activity and not the activity of the other members of the GRK6 family. The central catalytic domain of the GRKs, on the other hand, is relatively conserved and is essential for their activity. This region of the kinases may be used to screen for kinase inhibitors which have higher affinity for GRK6 or other kinases in the GRK family relative to other protein kinases. For example, RK is sensitive to inhibition by heparin (Palczewski et al., supra) and this sensitivity is dependent on the presence of a lysine stretch within the catalytic domain. This region is also found in other members of the GRK family including GRK6 (residues 214–225 of SEQ ID NO: 13) and agents that bind to this region of the protein kinase may preferentially inhibit protein kinases in the GRK family.

It is expected that agents which modulate the activity of GRK6 will behave as agonists or antagonists of the G protein-coupled receptor(s) which GRK6 phosphorylates. Inhibition of βARK2 activity with specific antibodies blocks desensitisation and increases odorant induced signalling in a similar manner to a receptor agonist [Schleicher et al., *Proc. Natl. Acad. Sci.* USA, 90: 1420–1424 (1993)], while overexpression of βARK1 in cell lines partially attenuates signalling through the β2 adenergic receptor in a similar manner to a receptor antagonist [Pippig et al., *J. Biol. Chem.*, 268: 3201–3208 (1993)]. Thus, modulators of GRK6 activity may allow for specific regulation of G protein-coupled receptors in leucocytic cells.

While the present invention has been described in terms of specific embodiments, it is understood that variations and modifications will occur to those skilled in the art. Accordingly, only such limitations as appear in the appended claims should be placed on the invention.

---

We claim:

1. A purified and isolated polynucleotide encoding a mammalian GRK6 enzyme.

2. The polynucleotide of claim 1 which is DNA.

3. The DNA of claim 2 which is a cDNA.

4. A DNA according to claim 2 which is the insert in plasmid pλ22 and which has the DNA sequence set out in SEQ ID NO: 12.

5. The DNA of claim 2 which encodes the GRK6 amino acid sequence set out in SEQ ID NO: 13.

6. The DNA of claim 2 which is a genomic DNA.

7. An RNA transcript of the genomic DNA of claim 6.

8. The DNA of claim 2 which is a wholly or partially chemically synthesized DNA.

9. The DNA of claim 6 further comprising an endogenous expression control DNA sequence.

10. A DNA vector comprising a DNA according to claim 2.

11. The vector of claim 10 wherein said DNA is operatively linked to an expression control DNA sequence.

12. A host cell stably transformed or transfected with a DNA according to claim 2 in a manner allowing the expression in said host cell of GRK6 enzyme possessing kinase activity.

13. A method for producing GRK6 enzyme, said method comprising growing a host cell according to claim 12 in a suitable nutrient medium and isolating GRK6 enzyme thereof from said cell or the medium of its growth.

14. A full length DNA encoding GRK6, wherein the DNA hybridizes to the non-coding strand corresponding to the DNA set out in SEQ ID NO: 12 under the following conditions: hybridization at 42° C. in buffer containing 50% formamide, 5×SSC, and 0.05M Na phosphate, and washing at 50° C. in buffer containing 0.2×SSC.

* * * * *

UNITED STATES PATENT AND TRADEMARK OFFICE
CERTIFICATE OF CORRECTION

PATENT NO. : 5,532,151
DATED : July 2, 1996
INVENTOR(S) : Chantry, et. al.

It is certified that error appears in the above-indentified patent and that said Letters Patent is hereby corrected as shown below:

Column 1, line 51, replace "The 62" with --The β--.

Column 4, line 7, replace "carded out" with --carried out--.

Column 5, line 59, replace "5'ATTGGATCC..." with --5'ATT<u>GGATCC</u>...--.

Column 5, line 66, replace "5'ATTTCTAGA..." with --5'ATT<u>TCTAGA</u>...--.

Column 6, line 40, replace "5'ATTGGATCC" with --5'ATT<u>GGATCC</u>--.

Column 6, line 45, replace "5'ATTTCTAGA" with --5'ATT<u>TCTAGA</u>--.

Column 9, line 47, replace "5'ATTTCTAGA..." with --5'ATT<u>TCTAGA</u>...--.

Signed and Sealed this

First Day of July, 1997

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

ATTGATCCGC ACHGGVAARM TSTAYGCNTG YAAR    34

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Thr Gly Lys Leu Tyr Ala
    1                5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Thr Gly Lys Met Tyr Ala
    1                5

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (i i) MOLECULE TYPE: DNA (i x) FEATURE:
    (A) NAME/KEY: Modified-site
    (B) LOCATION: group(16, 25)
    (C) OTHER INFORMATION: /note="The nucleotide at each of these positions is an inosine."

(x i) SEQUENCE DESCRIPTION: SEQ ID NO:4:

ATTTCTAGAD GCVAGNCCVA GRTCNGADAT NCGNAC      36

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (x i) SEQUENCE DESCRIPTION: SEQ ID NO:5:

Val Arg Ile Ser Asp Leu Gly Leu Ala
1                  5

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:6:

TCGCTCGTCA GCACTGGGGA CTGCCCA      27

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:7:

ATTGGATCCA TGCGGACGTG GCCGTGGTCA AG      32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

ATTTCTAGAA TGCGGACGTG GCCGTGGTCA AG      32

(2) INFORMATION FOR SEQ ID NO:9:

(i) SEQUENCE CHARACTERISTICS:
        (A) LENGTH: 294 base pairs
        (B) TYPE: nucleic acid
        (C) STRANDEDNESS: single
        (D) TOPOLOGY: linear ( i i ) MOLECULE TYPE: cDNA ( x i ) SEQUENCE DESCRIPTION: SEQ ID NO:9:

| | | | | | |
|---|---|---|---|---|---|
| ATCCTGGAGA | AAGTGAACAG | TAGGTTTGTA | GTGAGCTTAG | CCTACGCATA | TGAGACCAAG | 60 |
| GATGCACTGT | GCCTGGTGCT | GACATTGATG | ATTGGAGGCG | ACCTCAAGTT | CCACATCTAC | 120 |
| CACATGGGCC | AGGCTGGCTT | TCCCCAAGCA | CGTGCTGTCT | ATGTCTATGC | TGCCGAGATC | 180 |
| TGCTGTGGTC | TGGAGGACTT | ACACCGGGTT | CGCATCGTGT | ACAGGGACCT | GAAGCCCGAG | 240 |
| AACATCTTGC | TGGATGACCA | CGGCCACGTC | CGCATCTCCG | ACCTTGGCCT | CGCC | 294 |

( 2 ) INFORMATION FOR SEQ ID NO:10:

( i ) SEQUENCE CHARACTERISTICS:
        ( A ) LENGTH: 2206 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1926

( x i ) SEQUENCE DESCRIPTION: SEQ ID NO:10:

```
GCCGCGGCCC GGCGGCGAGC GCGACAGCCC ATG GAG CTC GAG AAC ATC GTA GCG        54
                                Met Glu Leu Glu Asn Ile Val Ala
                                 1               5

AAC ACG GTG CTA CTC AAG GCC CGG GAA GGT GGC GGT GGA AAT CGC AAA        102
Asn Thr Val Leu Leu Lys Ala Arg Glu Gly Gly Gly Gly Asn Arg Lys
         10                  15                  20

GGC AAA AGC AAG AAA TGG CGG CAG ATG CTC CAG TTC CCT CAC ATC AGC        150
Gly Lys Ser Lys Lys Trp Arg Gln Met Leu Gln Phe Pro His Ile Ser
 25                  30                  35                  40

CAG TGC GAA GAG CTG CGG CTC AGC CTC GAG CGT GAC TAT CAC AGC CTG        198
Gln Cys Glu Glu Leu Arg Leu Ser Leu Glu Arg Asp Tyr His Ser Leu
                 45                  50                  55

TGC GAG CGG CAC CGC ATT GGG CGC CTG CTG TTC CGA GAG TTC TGT GCC        246
Cys Glu Arg His Arg Ile Gly Arg Leu Leu Phe Arg Glu Phe Cys Ala
                 60                  65                  70

ACG AGG CCG GAG CTG AGC CGC TGC GTC GCC TTC CTG GAT GGG GTG GCC        294
Thr Arg Pro Glu Leu Ser Arg Cys Val Ala Phe Leu Asp Gly Val Ala
             75                  80                  85

GAG TAT GAA GTG ACC CCG GAT GAC AAG CGG AAG GCA TGT GGG CGG CAC        342
Glu Tyr Glu Val Thr Pro Asp Asp Lys Arg Lys Ala Cys Gly Arg His
         90                  95                 100

GTA ACG CAG AAT TTT CTG AGC CAC ACG GGT CCT GAC CTC ATC CCT GAG        390
Val Thr Gln Asn Phe Leu Ser His Thr Gly Pro Asp Leu Ile Pro Glu
105                 110                 115                 120

GTC CCC CGG CAG CTG GTG ACG GAC TGC ACC CAG CGG CTG GAG CAG GGT        438
Val Pro Arg Gln Leu Val Thr Asp Cys Thr Gln Arg Leu Glu Gln Gly
                125                 130                 135

CCT GCA AAG ACC TTT TCC AGG AAC TAC CCG GCT GAC CCA CGA GTA CCT        486
Pro Ala Lys Thr Phe Ser Arg Asn Tyr Pro Ala Asp Pro Arg Val Pro
                140                 145                 150

GAG CGT GGC CCC TTT GCC GAC TAC CTC GAC AGC ATC TAC TTC AAC CGT        534
Glu Arg Gly Pro Phe Ala Asp Tyr Leu Asp Ser Ile Tyr Phe Asn Arg
            155                 160                 165

TTC CTG CAG TGG AAG TGG CTG GAA AGG CAG CCA GTG ACC AAA AAC ACC        582
Phe Leu Gln Trp Lys Trp Leu Glu Arg Gln Pro Val Thr Lys Asn Thr
170                 175                 180
```

| | | | | | | | | | | | | | | | | |
|---|---|---|---|---|---|---|---|---|---|---|---|---|---|---|---|---|
| TTC | AGG | CAA | TAC | CGA | GTC | CTG | GGT | AAA | GGT | GGC | TTT | GGG | GAG | GTG | TGC | 630 |
| Phe | Arg | Gln | Tyr | Arg | Val | Leu | Gly | Lys | Gly | Gly | Phe | Gly | Glu | Val | Cys | |
| 185 | | | | 190 | | | | | 195 | | | | | 200 | | |
| GCC | TGC | CAG | GTG | CGG | GCC | ACA | GGT | AAG | ATG | TAT | GCC | TGC | AAG | AAG | CTA | 678 |
| Ala | Cys | Gln | Val | Arg | Ala | Thr | Gly | Lys | Met | Tyr | Ala | Cys | Lys | Lys | Leu | |
| | | | | 205 | | | | 210 | | | | | 215 | | | |
| GAG | AAA | AAG | CGG | ATC | AAG | AAG | CGG | AAA | GGG | GAG | GCC | ATG | GCG | CTG | AAC | 726 |
| Glu | Lys | Lys | Arg | Ile | Lys | Lys | Arg | Lys | Gly | Glu | Ala | Met | Ala | Leu | Asn | |
| | | | 220 | | | | 225 | | | | | 230 | | | | |
| GAG | AAG | CAG | ATC | CTG | GAG | AAA | GTG | AAC | AGT | AGG | TTT | GTA | GTG | AGC | TTC | 774 |
| Glu | Lys | Gln | Ile | Leu | Glu | Lys | Val | Asn | Ser | Arg | Phe | Val | Val | Ser | Phe | |
| | | 235 | | | | | 240 | | | | | 245 | | | | |
| GGC | TAC | GCC | TAT | GAG | ACC | AAG | GAC | GCG | CTG | TGC | CTG | GTG | CTG | ACA | CTG | 822 |
| Gly | Tyr | Ala | Tyr | Glu | Thr | Lys | Asp | Ala | Leu | Cys | Leu | Val | Leu | Thr | Leu | |
| | 250 | | | | | 255 | | | | | 260 | | | | | |
| ATG | AAC | GGG | GGC | GAC | CTC | AAG | TTC | CAC | ATC | TAC | CAC | ATG | GGC | CAG | GCT | 870 |
| Met | Asn | Gly | Gly | Asp | Leu | Lys | Phe | His | Ile | Tyr | His | Met | Gly | Gln | Ala | |
| 265 | | | | | 270 | | | | | 275 | | | | | 280 | |
| GGC | TTC | CCC | GAA | GCG | CGG | GCC | GTC | TTC | TAC | GCC | GCC | GAG | ATC | TGC | TGT | 918 |
| Gly | Phe | Pro | Glu | Ala | Arg | Ala | Val | Phe | Tyr | Ala | Ala | Glu | Ile | Cys | Cys | |
| | | | | 285 | | | | | 290 | | | | | 295 | | |
| GGC | CTG | GAG | GAC | CTG | CAC | CGG | GAG | CGC | ATC | GTG | TAC | AGG | GAC | CTG | AAG | 966 |
| Gly | Leu | Glu | Asp | Leu | His | Arg | Glu | Arg | Ile | Val | Tyr | Arg | Asp | Leu | Lys | |
| | | | 300 | | | | | 305 | | | | | 310 | | | |
| CCC | GAG | AAC | ATC | TTG | CTG | GAT | GAC | CAC | GGC | CAC | ATC | CGC | ATC | TCT | GAC | 1014 |
| Pro | Glu | Asn | Ile | Leu | Leu | Asp | Asp | His | Gly | His | Ile | Arg | Ile | Ser | Asp | |
| | | 315 | | | | | 320 | | | | | 325 | | | | |
| CTG | GGA | CTA | GCT | GTG | CAT | GTG | CCC | GAG | GGC | CAG | ACC | ATC | AAA | GGG | CGT | 1062 |
| Leu | Gly | Leu | Ala | Val | His | Val | Pro | Glu | Gly | Gln | Thr | Ile | Lys | Gly | Arg | |
| | 330 | | | | | 335 | | | | | 340 | | | | | |
| GTG | GGC | ACC | GTG | GGT | TAC | ATG | GCT | CCG | GAG | GTG | GTG | AAG | AAT | GAA | CGG | 1110 |
| Val | Gly | Thr | Val | Gly | Tyr | Met | Ala | Pro | Glu | Val | Val | Lys | Asn | Glu | Arg | |
| 345 | | | | | 350 | | | | | 355 | | | | | 360 | |
| TAC | ACG | TTC | AGC | CCT | GAC | TGG | TGG | GCG | CTC | GGC | TGC | CTC | CTG | TAC | GAG | 1158 |
| Tyr | Thr | Phe | Ser | Pro | Asp | Trp | Trp | Ala | Leu | Gly | Cys | Leu | Leu | Tyr | Glu | |
| | | | | 365 | | | | | 370 | | | | | 375 | | |
| ATG | ATC | GCA | GGC | CAG | TCG | CCC | TTC | CAG | CAG | AGG | AAG | AAG | AAG | ATC | AAG | 1206 |
| Met | Ile | Ala | Gly | Gln | Ser | Pro | Phe | Gln | Gln | Arg | Lys | Lys | Lys | Ile | Lys | |
| | | | 380 | | | | | 385 | | | | | 390 | | | |
| CGG | GAG | GAG | GTG | GAG | CGG | CTG | GTG | AAG | GAG | GTC | CCC | GAG | GAG | TAT | TCC | 1254 |
| Arg | Glu | Glu | Val | Glu | Arg | Leu | Val | Lys | Glu | Val | Pro | Glu | Glu | Tyr | Ser | |
| | | 395 | | | | | 400 | | | | | 405 | | | | |
| GAG | CGC | TTT | TCC | CCG | CAG | GCC | CGC | TCA | CTT | TGC | TCA | CAG | CTC | CTC | TGC | 1302 |
| Glu | Arg | Phe | Ser | Pro | Gln | Ala | Arg | Ser | Leu | Cys | Ser | Gln | Leu | Leu | Cys | |
| | 410 | | | | | 415 | | | | | 420 | | | | | |
| AAG | GAC | CCT | GCC | GAA | CCG | ACC | CTG | GGG | TGT | CGT | GGG | GGC | AGT | GCC | CGC | 1350 |
| Lys | Asp | Pro | Ala | Glu | Pro | Thr | Leu | Gly | Cys | Arg | Gly | Gly | Ser | Ala | Arg | |
| 425 | | | | | 430 | | | | | 435 | | | | | 440 | |
| GAG | GTG | AAG | GAG | CAC | CCC | CTC | TTT | AAG | AAG | CTG | AAC | TTC | AAG | CGG | CTG | 1398 |
| Glu | Val | Lys | Glu | His | Pro | Leu | Phe | Lys | Lys | Leu | Asn | Phe | Lys | Arg | Leu | |
| | | | | 445 | | | | | 450 | | | | | 455 | | |
| GGA | GCT | GGC | ATG | CTG | GAG | CCG | CCG | TTC | AAG | CCT | GAC | CCC | CAG | GCC | ATT | 1446 |
| Gly | Ala | Gly | Met | Leu | Glu | Pro | Pro | Phe | Lys | Pro | Asp | Pro | Gln | Ala | Ile | |
| | | | 460 | | | | | 465 | | | | | 470 | | | |
| TAC | TGC | AAG | GAT | GTT | CTG | GAC | ATT | GAA | CAG | TTC | TCT | ACG | GTC | AAG | GGC | 1494 |
| Tyr | Cys | Lys | Asp | Val | Leu | Asp | Ile | Glu | Gln | Phe | Ser | Thr | Val | Lys | Gly | |
| | | 475 | | | | | 480 | | | | | 485 | | | | |
| GTG | GAG | CTG | GAG | CCT | ACC | GAC | CAG | GAC | TTC | TAC | CAG | AAG | TTT | GCC | ACA | 1542 |
| Val | Glu | Leu | Glu | Pro | Thr | Asp | Gln | Asp | Phe | Tyr | Gln | Lys | Phe | Ala | Thr | |
| | 490 | | | | | 495 | | | | | 500 | | | | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| GGC | AGT | GTG | CCC | ATC | CCC | TGG | CAG | AAC | GAG | ATG | GTG | GAG | ACC | GAG | ATC | 1590 |
| Gly | Ser | Val | Pro | Ile | Pro | Trp | Gln | Asn | Glu | Met | Val | Glu | Thr | Glu | Ile |      |
| 505 |     |     |     |     | 510 |     |     |     |     | 515 |     |     |     |     | 520 |      |
| TGC | TTC | CAA | GAG | CTG | AAT | GTC | TTT | GGG | CTG | GAT | GGC | TCA | GTT | CCC | CCA | 1638 |
| Cys | Phe | Gln | Glu | Leu | Asn | Val | Phe | Gly | Leu | Asp | Gly | Ser | Val | Pro | Pro |      |
|     |     |     |     | 525 |     |     |     |     | 530 |     |     |     |     | 535 |     |      |
| GAC | CTG | GAC | TGG | AAG | GGC | CAG | CCA | CCT | GCA | CCT | CCT | AAA | AAG | GGA | CTG | 1686 |
| Asp | Leu | Asp | Trp | Lys | Gly | Gln | Pro | Pro | Ala | Pro | Pro | Lys | Lys | Gly | Leu |      |
|     |     |     | 540 |     |     |     |     | 545 |     |     |     |     | 550 |     |     |      |
| CTG | CAG | AGA | CTC | TTC | AGT | CGC | CAA | GAT | TGC | TGT | GGA | AAC | TGC | AGC | GAC | 1734 |
| Leu | Gln | Arg | Leu | Phe | Ser | Arg | Gln | Asp | Cys | Cys | Gly | Asn | Cys | Ser | Asp |      |
|     |     | 555 |     |     |     |     | 560 |     |     |     |     | 565 |     |     |     |      |
| ACA | GGG | AAG | AGC | TCC | CCA | CCC | GCC | TCT | AGC | CCC | CAG | CCC | GAG | GCC | CCC | 1782 |
| Thr | Gly | Lys | Ser | Ser | Pro | Pro | Ala | Ser | Ser | Pro | Gln | Pro | Glu | Ala | Pro |      |
|     | 570 |     |     |     |     | 575 |     |     |     |     | 580 |     |     |     |     |      |
| ACC | AGC | AGT | TGG | CGG | TAC | GAG | CTA | CTC | CGA | GCG | CCG | TTT | ACA | GTT | TTG | 1830 |
| Thr | Ser | Ser | Trp | Arg | Tyr | Glu | Leu | Leu | Arg | Ala | Pro | Phe | Thr | Val | Leu |      |
| 585 |     |     |     |     | 590 |     |     |     |     | 595 |     |     |     |     | 600 |      |
| CAC | AGT | GAT | CTT | CCC | CAT | TGT | CCA | CTC | AAG | TCG | TGG | CCT | GGG | GAA | CAC | 1878 |
| His | Ser | Asp | Leu | Pro | His | Cys | Pro | Leu | Lys | Ser | Trp | Pro | Gly | Glu | His |      |
|     |     |     |     | 605 |     |     |     |     | 610 |     |     |     |     | 615 |     |      |
| AGA | CGG | AGC | TGT | CCC | CAG | TGT | CCT | CCG | TCC | CTC | AGC | CCC | TGG | CCT | GGC | 1926 |
| Arg | Arg | Ser | Cys | Pro | Gln | Cys | Pro | Pro | Ser | Leu | Ser | Pro | Trp | Pro | Gly |      |
|     |     |     | 620 |     |     |     |     | 625 |     |     |     |     | 630 |     |     |      |

| | |
|---|---|
| TGAGAAAGGC AGGGCCTGGG CCATCCCTGG GACAAAGGTG CGTCCCTTCA GCTCTTCTCC | 1986 |
| GTGGAGCTCG GGGCTTTCTG TATTTATGTA TTTGTACGAA TGTATATAGC GACCAGAGCA | 2046 |
| TTCTTAATTC CCGCCGCAGA CCTGGCGCCC CCGCCTTGGC TCCTGGGGGC AGCCAGCCTG | 2106 |
| GCTGGAGAGC GGGACGTGGC AGAGGAGCCA CTGCCAAACT CAAGGCTCCT CTGGCCAGCT | 2166 |
| TGGATGGCTG AGGGTGGTCA CACCTGAGCT TCAGCACTGT | 2206 |

( 2 ) INFORMATION FOR SEQ ID NO:11:

( i ) SEQUENCE CHARACTERISTICS:
        ( A ) LENGTH: 632 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Glu | Leu | Glu | Asn | Ile | Val | Ala | Asn | Thr | Val | Leu | Leu | Lys | Ala | Arg |
| 1 | | | | 5 | | | | | 10 | | | | | 15 | |
| Glu | Gly | Gly | Gly | Gly | Asn | Arg | Lys | Gly | Lys | Ser | Lys | Lys | Trp | Arg | Gln |
| | | | 20 | | | | | 25 | | | | | 30 | | |
| Met | Leu | Gln | Phe | Pro | His | Ile | Ser | Gln | Cys | Glu | Glu | Leu | Arg | Leu | Ser |
| | | 35 | | | | | 40 | | | | | 45 | | | |
| Leu | Glu | Arg | Asp | Tyr | His | Ser | Leu | Cys | Glu | Arg | His | Arg | Ile | Gly | Arg |
| | 50 | | | | | 55 | | | | | 60 | | | | |
| Leu | Leu | Phe | Arg | Glu | Phe | Cys | Ala | Thr | Arg | Pro | Glu | Leu | Ser | Arg | Cys |
| 65 | | | | | 70 | | | | | 75 | | | | | 80 |
| Val | Ala | Phe | Leu | Asp | Gly | Val | Ala | Glu | Tyr | Glu | Val | Thr | Pro | Asp | Asp |
| | | | | 85 | | | | | 90 | | | | | 95 | |
| Lys | Arg | Lys | Ala | Cys | Gly | Arg | His | Val | Thr | Gln | Asn | Phe | Leu | Ser | His |
| | | | 100 | | | | | 105 | | | | | 110 | | |
| Thr | Gly | Pro | Asp | Leu | Ile | Pro | Glu | Val | Pro | Arg | Gln | Leu | Val | Thr | Asp |
| | | 115 | | | | | 120 | | | | | 125 | | | |
| Cys | Thr | Gln | Arg | Leu | Glu | Gln | Gly | Pro | Ala | Lys | Thr | Phe | Ser | Arg | Asn |
| | 130 | | | | | 135 | | | | | 140 | | | | |

```
Tyr Pro Ala Asp Pro Arg Val Pro Glu Arg Gly Pro Phe Ala Asp Tyr
145                 150                 155                 160

Leu Asp Ser Ile Tyr Phe Asn Arg Phe Leu Gln Trp Lys Trp Leu Glu
                165                 170                 175

Arg Gln Pro Val Thr Lys Asn Thr Phe Arg Gln Tyr Arg Val Leu Gly
            180                 185                 190

Lys Gly Gly Phe Gly Glu Val Cys Ala Cys Gln Val Arg Ala Thr Gly
        195                 200                 205

Lys Met Tyr Ala Cys Lys Lys Leu Glu Lys Lys Arg Ile Lys Lys Arg
    210                 215                 220

Lys Gly Glu Ala Met Ala Leu Asn Glu Lys Gln Ile Leu Glu Lys Val
225             230                 235                 240

Asn Ser Arg Phe Val Val Ser Phe Gly Tyr Ala Tyr Glu Thr Lys Asp
                245                 250                 255

Ala Leu Cys Leu Val Leu Thr Leu Met Asn Gly Gly Asp Leu Lys Phe
            260                 265                 270

His Ile Tyr His Met Gly Gln Ala Gly Phe Pro Glu Ala Arg Ala Val
        275                 280                 285

Phe Tyr Ala Ala Glu Ile Cys Cys Gly Leu Glu Asp Leu His Arg Glu
    290                 295                 300

Arg Ile Val Tyr Arg Asp Leu Lys Pro Glu Asn Ile Leu Leu Asp Asp
305                 310                 315                 320

His Gly His Ile Arg Ile Ser Asp Leu Gly Leu Ala Val His Val Pro
            325                 330                 335

Glu Gly Gln Thr Ile Lys Gly Arg Val Gly Thr Val Gly Tyr Met Ala
        340                 345                 350

Pro Glu Val Val Lys Asn Glu Arg Tyr Thr Phe Ser Pro Asp Trp Trp
    355                 360                 365

Ala Leu Gly Cys Leu Leu Tyr Glu Met Ile Ala Gly Gln Ser Pro Phe
370                 375                 380

Gln Gln Arg Lys Lys Lys Ile Lys Arg Glu Glu Val Glu Arg Leu Val
385                 390                 395                 400

Lys Glu Val Pro Glu Glu Tyr Ser Glu Arg Phe Ser Pro Gln Ala Arg
            405                 410                 415

Ser Leu Cys Ser Gln Leu Leu Cys Lys Asp Pro Ala Glu Pro Thr Leu
        420                 425                 430

Gly Cys Arg Gly Gly Ser Ala Arg Glu Val Lys Glu His Pro Leu Phe
    435                 440                 445

Lys Lys Leu Asn Phe Lys Arg Leu Gly Ala Gly Met Leu Glu Pro Pro
450                 455                 460

Phe Lys Pro Asp Pro Gln Ala Ile Tyr Cys Lys Asp Val Leu Asp Ile
465                 470                 475                 480

Glu Gln Phe Ser Thr Val Lys Gly Val Glu Leu Glu Pro Thr Asp Gln
            485                 490                 495

Asp Phe Tyr Gln Lys Phe Ala Thr Gly Ser Val Pro Ile Pro Trp Gln
        500                 505                 510

Asn Glu Met Val Glu Thr Glu Ile Cys Phe Gln Glu Leu Asn Val Phe
    515                 520                 525

Gly Leu Asp Gly Ser Val Pro Pro Asp Leu Asp Trp Lys Gly Gln Pro
530                 535                 540

Pro Ala Pro Pro Lys Lys Gly Leu Leu Gln Arg Leu Phe Ser Arg Gln
545                 550                 555                 560

Asp Cys Cys Gly Asn Cys Ser Asp Thr Gly Lys Ser Ser Pro Pro Ala
```

|  |  |  | 565 |  |  |  |  | 570 |  |  |  |  | 575 |  |  |
|---|---|---|---|---|---|---|---|---|---|---|---|---|---|---|---|
| Ser | Ser | Pro | Gln | Pro | Glu | Ala | Pro | Thr | Ser | Ser | Trp | Arg | Tyr | Glu | Leu |
|  |  |  | 580 |  |  |  |  | 585 |  |  |  |  | 590 |  |  |
| Leu | Arg | Ala | Pro | Phe | Thr | Val | Leu | His | Ser | Asp | Leu | Pro | His | Cys | Pro |
|  |  | 595 |  |  |  |  | 600 |  |  |  |  | 605 |  |  |  |
| Leu | Lys | Ser | Trp | Pro | Gly | Glu | His | Arg | Arg | Ser | Cys | Pro | Gln | Cys | Pro |
|  | 610 |  |  |  |  | 615 |  |  |  |  | 620 |  |  |  |  |
| Pro | Ser | Leu | Ser | Pro | Trp | Pro | Gly |  |  |  |  |  |  |  |  |
| 625 |  |  |  |  | 630 |  |  |  |  |  |  |  |  |  |  |

( 2 ) INFORMATION FOR SEQ ID NO:12:

( i ) SEQUENCE CHARACTERISTICS:
        ( A ) LENGTH: 2204 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1758

( x i ) SEQUENCE DESCRIPTION: SEQ ID NO:12:

| GCCGCGGCCC | GGCGGCGAGC | GCGACAGCCC | ATG | GAG | CTC | GAG | AAC | ATC | GTA | GCG | 54 |
|---|---|---|---|---|---|---|---|---|---|---|---|
|  |  |  | Met | Glu | Leu | Glu | Asn | Ile | Val | Ala |  |
|  |  |  | 1 |  |  |  | 5 |  |  |  |  |

| AAC | ACG | GTG | CTA | CTC | AAG | GCC | CGG | GAA | GGT | GGC | GGT | GGA | AAT | CGC | AAA | 102 |
|---|---|---|---|---|---|---|---|---|---|---|---|---|---|---|---|---|
| Asn | Thr | Val | Leu | Leu | Lys | Ala | Arg | Glu | Gly | Gly | Gly | Gly | Asn | Arg | Lys |  |
|  | 10 |  |  |  |  | 15 |  |  |  |  | 20 |  |  |  |  |  |

| GGC | AAA | AGC | AAG | AAA | TGG | CGG | CAG | ATG | CTC | CAG | TTC | CCT | CAC | ATC | AGC | 150 |
|---|---|---|---|---|---|---|---|---|---|---|---|---|---|---|---|---|
| Gly | Lys | Ser | Lys | Lys | Trp | Arg | Gln | Met | Leu | Gln | Phe | Pro | His | Ile | Ser |  |
| 25 |  |  |  |  | 30 |  |  |  |  | 35 |  |  |  |  | 40 |  |

| CAG | TGC | GAA | GAG | CTG | CGG | CTC | AGC | CTC | GAG | CGT | GAC | TAT | CAC | AGC | CTG | 198 |
|---|---|---|---|---|---|---|---|---|---|---|---|---|---|---|---|---|
| Gln | Cys | Glu | Glu | Leu | Arg | Leu | Ser | Leu | Glu | Arg | Asp | Tyr | His | Ser | Leu |  |
|  |  |  |  | 45 |  |  |  |  | 50 |  |  |  |  | 55 |  |  |

| TGC | GAG | CGG | CAC | CGC | ATT | GGG | CGC | CTG | CTG | TTC | CGA | GAG | TTC | TGT | GCC | 246 |
|---|---|---|---|---|---|---|---|---|---|---|---|---|---|---|---|---|
| Cys | Glu | Arg | His | Arg | Ile | Gly | Arg | Leu | Leu | Phe | Arg | Glu | Phe | Cys | Ala |  |
|  |  |  | 60 |  |  |  |  | 65 |  |  |  |  | 70 |  |  |  |

| ACG | AGG | CCG | GAG | CTG | AGC | CGC | TGC | GTC | GCC | TTC | CTG | GAT | GGG | GTG | GCC | 294 |
|---|---|---|---|---|---|---|---|---|---|---|---|---|---|---|---|---|
| Thr | Arg | Pro | Glu | Leu | Ser | Arg | Cys | Val | Ala | Phe | Leu | Asp | Gly | Val | Ala |  |
|  |  | 75 |  |  |  |  | 80 |  |  |  |  | 85 |  |  |  |  |

| GAG | TAT | GAA | GTG | ACC | CCG | GAT | GAC | AAG | CGG | AAG | GCA | TGT | GGG | CGG | CAC | 342 |
|---|---|---|---|---|---|---|---|---|---|---|---|---|---|---|---|---|
| Glu | Tyr | Glu | Val | Thr | Pro | Asp | Asp | Lys | Arg | Lys | Ala | Cys | Gly | Arg | His |  |
|  | 90 |  |  |  |  | 95 |  |  |  |  | 100 |  |  |  |  |  |

| GTA | ACG | CAG | AAT | TTT | CTG | AGC | CAC | ACG | GGT | CCT | GAC | CTC | ATC | CCT | GAG | 390 |
|---|---|---|---|---|---|---|---|---|---|---|---|---|---|---|---|---|
| Val | Thr | Gln | Asn | Phe | Leu | Ser | His | Thr | Gly | Pro | Asp | Leu | Ile | Pro | Glu |  |
| 105 |  |  |  |  | 110 |  |  |  |  | 115 |  |  |  |  | 120 |  |

| GTC | CCC | CGG | CAG | CTG | GTG | ACG | AAC | TGC | ACC | CAG | CGG | CTG | GAG | CAG | GGT | 438 |
|---|---|---|---|---|---|---|---|---|---|---|---|---|---|---|---|---|
| Val | Pro | Arg | Gln | Leu | Val | Thr | Asn | Cys | Thr | Gln | Arg | Leu | Glu | Gln | Gly |  |
|  |  |  |  | 125 |  |  |  |  | 130 |  |  |  |  | 135 |  |  |

| CCC | TGC | AAA | GAC | CTT | TTC | CAG | GAA | CTC | ACC | CGG | CTG | ACC | CAC | GAG | TAC | 486 |
|---|---|---|---|---|---|---|---|---|---|---|---|---|---|---|---|---|
| Pro | Cys | Lys | Asp | Leu | Phe | Gln | Glu | Leu | Thr | Arg | Leu | Thr | His | Glu | Tyr |  |
|  |  |  | 140 |  |  |  |  | 145 |  |  |  |  | 150 |  |  |  |

| CTG | AGC | GTG | GCC | CCT | TTT | GCC | GAC | TAC | CTC | GAC | AGC | ATC | TAC | TTC | AAC | 534 |
|---|---|---|---|---|---|---|---|---|---|---|---|---|---|---|---|---|
| Leu | Ser | Val | Ala | Pro | Phe | Ala | Asp | Tyr | Leu | Asp | Ser | Ile | Tyr | Phe | Asn |  |
|  |  | 155 |  |  |  |  | 160 |  |  |  |  | 165 |  |  |  |  |

| CGT | TTC | CTG | CAG | TGG | AAG | TGG | CTG | GAA | AGG | CAG | CCA | GTG | ACC | AAA | AAC | 582 |
|---|---|---|---|---|---|---|---|---|---|---|---|---|---|---|---|---|
| Arg | Phe | Leu | Gln | Trp | Lys | Trp | Leu | Glu | Arg | Gln | Pro | Val | Thr | Lys | Asn |  |
|  | 170 |  |  |  |  | 175 |  |  |  |  | 180 |  |  |  |  |  |

| ACC | TTC | AGG | CAA | TAC | CGA | GTC | CTG | GGT | AAA | GGT | GGC | TTT | GGG | GAG | GTG | 630 |
|---|---|---|---|---|---|---|---|---|---|---|---|---|---|---|---|---|

|     |     |     |     |     |     |     |     |     |     |     |     |     |     |     |      |
|-----|-----|-----|-----|-----|-----|-----|-----|-----|-----|-----|-----|-----|-----|-----|------|
| Thr | Phe | Arg | Gln | Tyr | Arg | Val | Leu | Gly | Lys | Gly | Gly | Phe | Gly | Glu | Val  |
| 185 |     |     |     | 190 |     |     |     |     | 195 |     |     |     |     |     | 200  |

| TGC | GCC | TGC | CAG | GTG | CGG | GCC | ACA | GGT | AAG | ATG | TAT | GCC | TGC | AAG | AAG | 678 |
|-----|-----|-----|-----|-----|-----|-----|-----|-----|-----|-----|-----|-----|-----|-----|-----|-----|
| Cys | Ala | Cys | Gln | Val | Arg | Ala | Thr | Gly | Lys | Met | Tyr | Ala | Cys | Lys | Lys |     |
|     |     |     |     | 205 |     |     |     |     | 210 |     |     |     |     | 215 |     |     |

| CTA | GAG | AAA | AAG | CGG | ATC | AAG | AAG | CGG | AAA | GGG | GAG | GCC | ATG | GCG | CTG | 726 |
|-----|-----|-----|-----|-----|-----|-----|-----|-----|-----|-----|-----|-----|-----|-----|-----|-----|
| Leu | Glu | Lys | Lys | Arg | Ile | Lys | Lys | Arg | Lys | Gly | Glu | Ala | Met | Ala | Leu |     |
|     |     |     | 220 |     |     |     |     | 225 |     |     |     |     | 230 |     |     |     |

| AAC | GAG | AAG | CAG | ATC | CTG | GAG | AAA | GTG | AAC | AGT | AGG | TTT | GTA | GTG | AGC | 774 |
|-----|-----|-----|-----|-----|-----|-----|-----|-----|-----|-----|-----|-----|-----|-----|-----|-----|
| Asn | Glu | Lys | Gln | Ile | Leu | Glu | Lys | Val | Asn | Ser | Arg | Phe | Val | Val | Ser |     |
|     |     | 235 |     |     |     |     | 240 |     |     |     |     | 245 |     |     |     |     |

| TTG | GCC | TAC | GCC | TAT | GAG | ACC | AAG | GAC | GCG | CTG | TGC | CTG | GTG | CTG | ACA | 822 |
|-----|-----|-----|-----|-----|-----|-----|-----|-----|-----|-----|-----|-----|-----|-----|-----|-----|
| Leu | Ala | Tyr | Ala | Tyr | Glu | Thr | Lys | Asp | Ala | Leu | Cys | Leu | Val | Leu | Thr |     |
|     | 250 |     |     |     |     | 255 |     |     |     |     | 260 |     |     |     |     |     |

| CTG | ATG | AAC | GGG | GGC | GAC | CTC | AAG | TTC | CAC | ATC | TAC | CAC | ATG | GGC | CAG | 870 |
|-----|-----|-----|-----|-----|-----|-----|-----|-----|-----|-----|-----|-----|-----|-----|-----|-----|
| Leu | Met | Asn | Gly | Gly | Asp | Leu | Lys | Phe | His | Ile | Tyr | His | Met | Gly | Gln |     |
| 265 |     |     |     |     | 270 |     |     |     |     | 275 |     |     |     |     | 280 |     |

| GCT | GGC | TTC | CCC | GAA | GCG | CGG | GCC | GTC | TTC | TAC | GCC | GCC | GAG | ATC | TGC | 918 |
|-----|-----|-----|-----|-----|-----|-----|-----|-----|-----|-----|-----|-----|-----|-----|-----|-----|
| Ala | Gly | Phe | Pro | Glu | Ala | Arg | Ala | Val | Phe | Tyr | Ala | Ala | Glu | Ile | Cys |     |
|     |     |     |     | 285 |     |     |     |     | 290 |     |     |     |     | 295 |     |     |

| TGT | GGC | CTG | GAG | GAC | CTG | CAC | CGG | GAG | CGC | ATC | GTG | TAC | AGG | GAC | CTG | 966 |
|-----|-----|-----|-----|-----|-----|-----|-----|-----|-----|-----|-----|-----|-----|-----|-----|-----|
| Cys | Gly | Leu | Glu | Asp | Leu | His | Arg | Glu | Arg | Ile | Val | Tyr | Arg | Asp | Leu |     |
|     |     |     | 300 |     |     |     |     | 305 |     |     |     |     | 310 |     |     |     |

| AAG | CCC | GAG | AAC | ATC | TTG | CTG | GAT | GAC | CAC | GGC | CAC | ATC | CGC | ATC | TCT | 1014 |
|-----|-----|-----|-----|-----|-----|-----|-----|-----|-----|-----|-----|-----|-----|-----|-----|------|
| Lys | Pro | Glu | Asn | Ile | Leu | Leu | Asp | Asp | His | Gly | His | Ile | Arg | Ile | Ser |      |
|     |     |     | 315 |     |     |     |     | 320 |     |     |     |     | 325 |     |     |      |

| GAC | CTG | GGA | CTA | GCT | GTG | CAT | GTG | CCC | GAG | GGC | CAG | ACC | ATC | AAA | GGG | 1062 |
|-----|-----|-----|-----|-----|-----|-----|-----|-----|-----|-----|-----|-----|-----|-----|-----|------|
| Asp | Leu | Gly | Leu | Ala | Val | His | Val | Pro | Glu | Gly | Gln | Thr | Ile | Lys | Gly |      |
|     |     | 330 |     |     |     |     | 335 |     |     |     |     | 340 |     |     |     |      |

| CGT | GTG | GGC | ACC | GTG | GGT | TAC | ATG | GCT | CCG | GAG | GTG | GTG | AAG | AAT | GAA | 1110 |
|-----|-----|-----|-----|-----|-----|-----|-----|-----|-----|-----|-----|-----|-----|-----|-----|------|
| Arg | Val | Gly | Thr | Val | Gly | Tyr | Met | Ala | Pro | Glu | Val | Val | Lys | Asn | Glu |      |
| 345 |     |     |     |     | 350 |     |     |     |     | 355 |     |     |     |     | 360 |      |

| CGG | TAC | ACG | TTC | AGC | CCT | GAC | TGG | TGG | GCG | CTC | GGC | TGC | CTC | CTG | TAC | 1158 |
|-----|-----|-----|-----|-----|-----|-----|-----|-----|-----|-----|-----|-----|-----|-----|-----|------|
| Arg | Tyr | Thr | Phe | Ser | Pro | Asp | Trp | Trp | Ala | Leu | Gly | Cys | Leu | Leu | Tyr |      |
|     |     |     |     | 365 |     |     |     |     | 370 |     |     |     |     | 375 |     |      |

| GAG | ATG | ATC | GCA | GGC | CAG | TCG | CCC | TTC | CAG | CAG | AGG | AAG | AAG | AAG | ATC | 1206 |
|-----|-----|-----|-----|-----|-----|-----|-----|-----|-----|-----|-----|-----|-----|-----|-----|------|
| Glu | Met | Ile | Ala | Gly | Gln | Ser | Pro | Phe | Gln | Gln | Arg | Lys | Lys | Lys | Ile |      |
|     |     |     | 380 |     |     |     |     | 385 |     |     |     |     | 390 |     |     |      |

| AAG | CGG | GAG | GAG | GTG | GAG | CGG | CTG | GTG | AAG | GAG | GTC | CCC | GAG | GAG | TAT | 1254 |
|-----|-----|-----|-----|-----|-----|-----|-----|-----|-----|-----|-----|-----|-----|-----|-----|------|
| Lys | Arg | Glu | Glu | Val | Glu | Arg | Leu | Val | Lys | Glu | Val | Pro | Glu | Glu | Tyr |      |
|     |     | 395 |     |     |     |     | 400 |     |     |     |     | 405 |     |     |     |      |

| TCC | GAG | CGC | TTT | TCC | CCG | CAG | GCC | CGC | TCA | CTT | TGC | TCA | CAG | CTC | CTC | 1302 |
|-----|-----|-----|-----|-----|-----|-----|-----|-----|-----|-----|-----|-----|-----|-----|-----|------|
| Ser | Glu | Arg | Phe | Ser | Pro | Gln | Ala | Arg | Ser | Leu | Cys | Ser | Gln | Leu | Leu |      |
|     |     | 410 |     |     |     |     | 415 |     |     |     |     | 420 |     |     |     |      |

| TGC | AAG | GAC | CCT | GCC | GAA | CGC | CTG | GGG | TGT | CGT | GGG | GGC | AGT | GCC | CGC | 1350 |
|-----|-----|-----|-----|-----|-----|-----|-----|-----|-----|-----|-----|-----|-----|-----|-----|------|
| Cys | Lys | Asp | Pro | Ala | Glu | Arg | Leu | Gly | Cys | Arg | Gly | Gly | Ser | Ala | Arg |      |
| 425 |     |     |     |     | 430 |     |     |     |     | 435 |     |     |     |     | 440 |      |

| GAG | GTG | AAG | GAG | CAC | CCC | CTC | TTT | AAG | AAG | CTG | AAC | TTC | AAG | CGG | CTG | 1398 |
|-----|-----|-----|-----|-----|-----|-----|-----|-----|-----|-----|-----|-----|-----|-----|-----|------|
| Glu | Val | Lys | Glu | His | Pro | Leu | Phe | Lys | Lys | Leu | Asn | Phe | Lys | Arg | Leu |      |
|     |     |     |     | 445 |     |     |     |     | 450 |     |     |     |     | 455 |     |      |

| GGA | GCT | GGC | ATG | CTG | GAG | CCG | CCG | TTC | AAG | CCT | GAC | CCC | CAG | GCC | ATT | 1446 |
|-----|-----|-----|-----|-----|-----|-----|-----|-----|-----|-----|-----|-----|-----|-----|-----|------|
| Gly | Ala | Gly | Met | Leu | Glu | Pro | Pro | Phe | Lys | Pro | Asp | Pro | Gln | Ala | Ile |      |
|     |     |     | 460 |     |     |     |     | 465 |     |     |     |     | 470 |     |     |      |

| TAC | TGC | AAG | GAT | GTT | CTG | GAC | ATT | GAA | CAG | TTC | TCT | ACG | GTC | AAG | GGC | 1494 |
|-----|-----|-----|-----|-----|-----|-----|-----|-----|-----|-----|-----|-----|-----|-----|-----|------|
| Tyr | Cys | Lys | Asp | Val | Leu | Asp | Ile | Glu | Gln | Phe | Ser | Thr | Val | Lys | Gly |      |
|     |     | 475 |     |     |     |     | 480 |     |     |     |     | 485 |     |     |     |      |

| GTG | GAG | CTG | GAG | CCT | ACC | GAC | CAG | GAC | TTC | TAC | CAG | AAG | TTT | GCC | ACA | 1542 |
|-----|-----|-----|-----|-----|-----|-----|-----|-----|-----|-----|-----|-----|-----|-----|-----|------|
| Val | Glu | Leu | Glu | Pro | Thr | Asp | Gln | Asp | Phe | Tyr | Gln | Lys | Phe | Ala | Thr |      |
|     | 490 |     |     |     |     | 495 |     |     |     |     | 500 |     |     |     |     |      |

| GGC | AGT | GTG | CCC | ATC | CCC | TGG | CAG | AAC | GAG | ATG | GTG | GAG | ACC | GAG | TGC | 1590 |
|-----|-----|-----|-----|-----|-----|-----|-----|-----|-----|-----|-----|-----|-----|-----|-----|------|

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gly | Ser | Val | Pro | Ile | Pro | Trp | Gln | Asn | Glu | Met | Val | Glu | Thr | Glu | Cys |      |
| 505 |     |     |     |     | 510 |     |     |     |     | 515 |     |     |     |     | 520 |      |
| TTC | CAA | GAG | CTG | AAT | GTC | TTT | GGG | CTG | GAT | GGC | TCA | GTT | CCC | CCA | GAC | 1638 |
| Phe | Gln | Glu | Leu | Asn | Val | Phe | Gly | Leu | Asp | Gly | Ser | Val | Pro | Pro | Asp |      |
|     |     |     |     | 525 |     |     |     |     | 530 |     |     |     |     | 535 |     |      |
| CTG | GAC | TGG | AAG | GGC | CAG | CCA | CCT | GCA | CCT | CCT | AAA | AAG | GGA | CTG | CTG | 1686 |
| Leu | Asp | Trp | Lys | Gly | Gln | Pro | Pro | Ala | Pro | Pro | Lys | Lys | Gly | Leu | Leu |      |
|     |     |     | 540 |     |     |     |     | 545 |     |     |     |     | 550 |     |     |      |
| CAG | AGA | CTC | TTC | AGT | CGC | CAA | GAT | TGC | TGT | GGA | AAC | TGC | AGC | GAC | AGC | 1734 |
| Gln | Arg | Leu | Phe | Ser | Arg | Gln | Asp | Cys | Cys | Gly | Asn | Cys | Ser | Asp | Ser |      |
|     |     | 555 |     |     |     |     | 560 |     |     |     |     | 565 |     |     |     |      |
| GAG | GAA | GAG | CTC | CCC | ACC | CGC | CTC | TAGCCCCAG | | CCCGAGGCCC | | CCACCAGCAG | | | | 1788 |
| Glu | Glu | Glu | Leu | Pro | Thr | Arg | Leu |     |     |     |     |     |     |     |     |      |
| 570 |     |     |     |     |     | 575 |     |     |     |     |     |     |     |     |     |      |

| | | | | |
|---|---|---|---|---|
| TTGGCGGTAC | GAGCTACTCC | GAGCGCCGTT | TACAGTTTTG | CACAGTGATC | TTCCCCATTG | 1848 |
| TCCACTCAAG | TCGTGGCCTG | GGGAACACAG | ACGGAGCTGT | CCCCAGTGTC | CTCCGTCCCT | 1908 |
| CAGCCCCTGG | CCTGGCTGAG | AAAGGCAGGG | CCTGGGCCAT | CCCTGGGACA | AAGGTGCGTC | 1968 |
| CCTTCAGCTC | TTCTCCGTGG | AGCTCGGGGC | TTTCTGTATT | TATGTATTTG | TACGAATGTA | 2028 |
| TATAGCGACC | AGAGCATTCT | TAATTCCCGC | CGCAGACCTG | GCGCCCCGC  | CTTGGCTCCT | 2088 |
| GGGGGCAGCC | AGCCTGGCTG | GAGAGCGGGA | CGTGGCAGAG | GAGCCACTGC | CAAACTCAAG | 2148 |
| GCTCCTCTGG | CCAGCTTGGA | TGGCTGAGGG | TGGTCACACC | TGAGCTTCAG | CACTGT     | 2204 |

( 2 ) INFORMATION FOR SEQ ID NO:13:

( i ) SEQUENCE CHARACTERISTICS:
        ( A ) LENGTH: 576 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | | |
|---|---|---|---|---|---|---|---|---|---|---|---|---|---|---|---|
| Met | Glu | Leu | Glu | Asn | Ile | Val | Ala | Asn | Thr | Val | Leu | Leu | Lys | Ala | Arg |
| 1   |     |     |     | 5   |     |     |     |     | 10  |     |     |     |     | 15  |     |
| Glu | Gly | Gly | Gly | Gly | Asn | Arg | Lys | Gly | Lys | Ser | Lys | Lys | Trp | Arg | Gln |
|     |     |     | 20  |     |     |     |     | 25  |     |     |     |     | 30  |     |     |
| Met | Leu | Gln | Phe | Pro | His | Ile | Ser | Gln | Cys | Glu | Glu | Leu | Arg | Leu | Ser |
|     |     | 35  |     |     |     |     | 40  |     |     |     |     | 45  |     |     |     |
| Leu | Glu | Arg | Asp | Tyr | His | Ser | Leu | Cys | Glu | Arg | His | Arg | Ile | Gly | Arg |
|     | 50  |     |     |     |     | 55  |     |     |     |     | 60  |     |     |     |     |
| Leu | Leu | Phe | Arg | Glu | Phe | Cys | Ala | Thr | Arg | Pro | Glu | Leu | Ser | Arg | Cys |
| 65  |     |     |     |     | 70  |     |     |     |     | 75  |     |     |     |     | 80  |
| Val | Ala | Phe | Leu | Asp | Gly | Val | Ala | Glu | Tyr | Glu | Val | Thr | Pro | Asp | Asp |
|     |     |     |     | 85  |     |     |     |     | 90  |     |     |     |     | 95  |     |
| Lys | Arg | Lys | Ala | Cys | Gly | Arg | His | Val | Thr | Gln | Asn | Phe | Leu | Ser | His |
|     |     |     | 100 |     |     |     |     | 105 |     |     |     |     | 110 |     |     |
| Thr | Gly | Pro | Asp | Leu | Ile | Pro | Glu | Val | Pro | Arg | Gln | Leu | Val | Thr | Asn |
|     |     | 115 |     |     |     |     | 120 |     |     |     |     | 125 |     |     |     |
| Cys | Thr | Gln | Arg | Leu | Glu | Gln | Gly | Pro | Cys | Lys | Asp | Leu | Phe | Gln | Glu |
|     | 130 |     |     |     |     | 135 |     |     |     |     | 140 |     |     |     |     |
| Leu | Thr | Arg | Leu | Thr | His | Glu | Tyr | Leu | Ser | Val | Ala | Pro | Phe | Ala | Asp |
| 145 |     |     |     |     | 150 |     |     |     |     | 155 |     |     |     |     | 160 |
| Tyr | Leu | Asp | Ser | Ile | Tyr | Phe | Asn | Arg | Phe | Leu | Gln | Trp | Lys | Trp | Leu |
|     |     |     |     | 165 |     |     |     |     | 170 |     |     |     |     | 175 |     |
| Glu | Arg | Gln | Pro | Val | Thr | Lys | Asn | Thr | Phe | Arg | Gln | Tyr | Arg | Val | Leu |
|     |     |     | 180 |     |     |     |     | 185 |     |     |     |     | 190 |     |     |

```
Gly Lys Gly Gly Phe Gly Glu Val Cys Ala Cys Gln Val Arg Ala Thr
    195             200                 205
Gly Lys Met Tyr Ala Cys Lys Lys Leu Glu Lys Lys Arg Ile Lys Lys
    210             215                 220
Arg Lys Gly Glu Ala Met Ala Leu Asn Glu Lys Gln Ile Leu Glu Lys
225             230              235                         240
Val Asn Ser Arg Phe Val Val Ser Leu Ala Tyr Ala Tyr Glu Thr Lys
                245             250                 255
Asp Ala Leu Cys Leu Val Leu Thr Leu Met Asn Gly Gly Asp Leu Lys
            260             265                 270
Phe His Ile Tyr His Met Gly Gln Ala Gly Phe Pro Glu Ala Arg Ala
        275             280                 285
Val Phe Tyr Ala Ala Glu Ile Cys Cys Gly Leu Glu Asp Leu His Arg
    290             295                 300
Glu Arg Ile Val Tyr Arg Asp Leu Lys Pro Glu Asn Ile Leu Leu Asp
305             310                 315                     320
Asp His Gly His Ile Arg Ile Ser Asp Leu Gly Leu Ala Val His Val
                325             330                 335
Pro Glu Gly Gln Thr Ile Lys Gly Arg Val Gly Thr Val Gly Tyr Met
            340             345                 350
Ala Pro Glu Val Val Lys Asn Glu Arg Tyr Thr Phe Ser Pro Asp Trp
        355             360                 365
Trp Ala Leu Gly Cys Leu Leu Tyr Glu Met Ile Ala Gly Gln Ser Pro
    370             375                 380
Phe Gln Gln Arg Lys Lys Lys Ile Lys Arg Glu Glu Val Glu Arg Leu
385             390                 395                     400
Val Lys Glu Val Pro Glu Glu Tyr Ser Glu Arg Phe Ser Pro Gln Ala
                405             410                 415
Arg Ser Leu Cys Ser Gln Leu Leu Cys Lys Asp Pro Ala Glu Arg Leu
            420             425                 430
Gly Cys Arg Gly Gly Ser Ala Arg Glu Val Lys Glu His Pro Leu Phe
        435             440                 445
Lys Lys Leu Asn Phe Lys Arg Leu Gly Ala Gly Met Leu Glu Pro Pro
    450             455                 460
Phe Lys Pro Asp Pro Gln Ala Ile Tyr Cys Lys Asp Val Leu Asp Ile
465             470                 475                     480
Glu Gln Phe Ser Thr Val Lys Gly Val Glu Leu Glu Pro Thr Asp Gln
                485             490                 495
Asp Phe Tyr Gln Lys Phe Ala Thr Gly Ser Val Pro Ile Pro Trp Gln
            500             505                 510
Asn Glu Met Val Glu Thr Glu Cys Phe Gln Glu Leu Asn Val Phe Gly
        515             520                 525
Leu Asp Gly Ser Val Pro Pro Asp Leu Asp Trp Lys Gly Gln Pro Pro
    530             535                 540
Ala Pro Pro Lys Lys Gly Leu Leu Gln Arg Leu Phe Ser Arg Gln Asp
545             550                 555                     560
Cys Cys Gly Asn Cys Ser Asp Ser Glu Glu Glu Leu Pro Thr Arg Leu
                565             570                 575
```

( 2 ) INFORMATION FOR SEQ ID NO:14:

( i ) SEQUENCE CHARACTERISTICS:
        ( A ) LENGTH: 590 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met<br>1 | Glu | Leu | Glu | Asn<br>5 | Ile | Val | Ala | Asn | Thr<br>10 | Val | Leu | Leu | Lys | Ala<br>15 | Arg |
|---|---|---|---|---|---|---|---|---|---|---|---|---|---|---|---|
| Glu | Gly | Gly | Gly<br>20 | Gly | Lys | Arg | Lys | Gly<br>25 | Lys | Ser | Lys | Lys | Trp<br>30 | Lys | Glu |
| Ile | Leu | Lys<br>35 | Phe | Pro | His | Ile | Ser<br>40 | Gln | Cys | Glu | Asp | Leu<br>45 | Arg | Arg | Thr |
| Ile | Asp<br>50 | Arg | Asp | Tyr | Cys | Ser<br>55 | Leu | Cys | Asp | Lys | Gln<br>60 | Pro | Ile | Gly | Arg |
| Leu<br>65 | Leu | Phe | Arg | Gln | Phe<br>70 | Cys | Glu | Thr | Arg | Pro<br>75 | Gly | Leu | Glu | Cys | Tyr<br>80 |
| Ile | Gln | Phe | Leu | Asp<br>85 | Ser | Val | Ala | Glu | Tyr<br>90 | Glu | Val | Thr | Pro | Asp<br>95 | Glu |
| Lys | Leu | Gly | Glu<br>100 | Lys | Gly | Lys | Glu | Ile<br>105 | Met | Thr | Lys | Tyr | Leu<br>110 | Thr | Pro |
| Lys | Ser | Pro<br>115 | Val | Phe | Ile | Ala | Gln<br>120 | Val | Gly | Gln | Asp | Leu<br>125 | Val | Ser | Gln |
| Thr | Glu<br>130 | Glu | Lys | Leu | Leu | Gln<br>135 | Lys | Pro | Cys | Lys | Glu<br>140 | Leu | Phe | Ser | Ala |
| Cys<br>145 | Ala | Gln | Ser | Val | His<br>150 | Glu | Tyr | Leu | Arg | Gly<br>155 | Glu | Pro | Phe | His | Glu<br>160 |
| Tyr | Leu | Asp | Ser | Met<br>165 | Phe | Phe | Asp | Arg | Phe<br>170 | Leu | Gln | Trp | Lys | Trp<br>175 | Leu |
| Glu | Arg | Gln | Pro<br>180 | Val | Thr | Lys | Asn | Thr<br>185 | Phe | Arg | Gln | Tyr | Arg<br>190 | Val | Leu |
| Gly | Lys | Gly<br>195 | Gly | Phe | Gly | Glu | Val<br>200 | Cys | Ala | Cys | Gln | Val<br>205 | Arg | Ala | Thr |
| Gly | Lys<br>210 | Met | Tyr | Ala | Cys | Lys<br>215 | Arg | Leu | Glu | Lys | Lys<br>220 | Arg | Ile | Lys | Lys |
| Arg<br>225 | Lys | Gly | Glu | Ser | Met<br>230 | Ala | Leu | Asn | Glu | Lys<br>235 | Gln | Ile | Leu | Glu | Lys<br>240 |
| Val | Asn | Ser | Gln | Phe<br>245 | Val | Val | Asn | Leu | Ala<br>250 | Tyr | Ala | Tyr | Glu | Thr<br>255 | Lys |
| Asp | Ala | Leu | Cys<br>260 | Leu | Val | Leu | Thr | Ile<br>265 | Met | Asn | Gly | Gly | Asp<br>270 | Leu | Lys |
| Phe | His | Ile<br>275 | Tyr | Asn | Met | Gly | Asn<br>280 | Pro | Gly | Phe | Glu | Glu<br>285 | Glu | Arg | Ala |
| Leu | Phe<br>290 | Tyr | Ala | Ala | Glu | Ile<br>295 | Leu | Cys | Gly | Leu | Glu<br>300 | Asp | Leu | His | Arg |
| Glu<br>305 | Asn | Thr | Val | Tyr | Arg<br>310 | Asp | Leu | Lys | Pro | Glu<br>315 | Asn | Ile | Leu | Leu | Asp<br>320 |
| Asp | Tyr | Gly | His | Ile<br>325 | Arg | Ile | Ser | Asp | Leu<br>330 | Gly | Leu | Ala | Val | Lys<br>335 | Ile |
| Pro | Glu | Gly | Asp<br>340 | Leu | Ile | Arg | Gly | Arg<br>345 | Val | Gly | Thr | Val | Gly<br>350 | Tyr | Met |
| Ala | Pro | Glu<br>355 | Val | Leu | Asn | Asn | Gln<br>360 | Arg | Tyr | Gly | Leu | Ser<br>365 | Pro | Asp | Tyr |
| Trp | Gly<br>370 | Leu | Gly | Cys | Leu | Ile<br>375 | Tyr | Glu | Met | Ile | Glu<br>380 | Gly | Gln | Ser | Pro |
| Phe<br>385 | Arg | Gly | Arg | Lys | Glu<br>390 | Lys | Val | Lys | Arg | Glu<br>395 | Glu | Val | Asp | Arg | Arg<br>400 |

```
Val  Leu  Glu  Thr  Glu  Glu  Val  Tyr  Ser  His  Lys  Phe  Ser  Glu  Glu  Ala
               405                      410                      415

Lys  Ser  Ile  Cys  Lys  Met  Leu  Leu  Thr  Lys  Asp  Ala  Lys  Gln  Arg  Leu
               420                      425                      430

Gly  Cys  Gln  Glu  Glu  Gly  Ala  Ala  Glu  Val  Lys  Arg  His  Pro  Phe  Phe
               435                      440                      445

Arg  Asn  Met  Asn  Phe  Lys  Arg  Leu  Glu  Ala  Gly  Met  Leu  Asp  Pro  Pro
     450                      455                      460

Phe  Val  Pro  Asp  Pro  Arg  Ala  Val  Tyr  Cys  Lys  Asp  Val  Leu  Asp  Ile
465                      470                      475                      480

Glu  Gln  Phe  Ser  Thr  Val  Lys  Gly  Val  Asn  Leu  Asp  His  Thr  Asp  Asp
               485                      490                      495

Asp  Phe  Tyr  Ser  Lys  Phe  Ser  Thr  Gly  Ser  Val  Ser  Ile  Pro  Trp  Gln
               500                      505                      510

Asn  Glu  Met  Ile  Glu  Thr  Glu  Cys  Phe  Lys  Glu  Leu  Asn  Val  Phe  Gly
               515                      520                      525

Pro  Asn  Gly  Thr  Leu  Pro  Pro  Asp  Leu  Asn  Arg  Asn  His  Pro  Pro  Glu
     530                      535                      540

Pro  Pro  Lys  Lys  Gly  Leu  Leu  Gln  Arg  Leu  Phe  Lys  Arg  Gln  His  Gln
545                      550                      555                      560

Asn  Asn  Ser  Lys  Ser  Ser  Pro  Ser  Ser  Lys  Thr  Ser  Phe  Asn  His  His
                    565                      570                      575

Ile  Asn  Ser  Asn  His  Val  Ser  Ser  Asn  Ser  Thr  Gly  Ser  Ser
               580                      585                      590
```

(2) INFORMATION FOR SEQ ID NO:15:

(i) SEQUENCE CHARACTERISTICS:
　　　　(A) LENGTH: 500 amino acids
　　　　(B) TYPE: amino acid
　　　　(D) TOPOLOGY: linear (ii) MOLECULE TYPE: protein (xi) SEQUENCE DESCRIPTION: SEQ ID NO:15:

```
Met  Glu  Leu  Glu  Asn  Ile  Val  Ala  Asn  Ser  Leu  Leu  Leu  Lys  Ala  Arg
1                 5                       10                      15

Gln  Glu  Lys  Asp  Tyr  Ser  Ser  Leu  Cys  Asp  Lys  Gln  Pro  Ile  Gly  Arg
               20                       25                      30

Arg  Leu  Phe  Arg  Gln  Phe  Cys  Asp  Thr  Lys  Pro  Thr  Leu  Lys  Arg  His
               35                       40                      45

Ile  Glu  Phe  Leu  Asp  Ala  Val  Ala  Glu  Tyr  Glu  Val  Ala  Asp  Asp  Glu
     50                       55                      60

Asp  Arg  Ser  Asp  Cys  Gly  Leu  Ser  Ile  Leu  Asp  Arg  Phe  Phe  Asn  Asp
65                       70                      75                       80

Lys  Leu  Ala  Ala  Pro  Leu  Pro  Glu  Ile  Pro  Pro  Asp  Val  Val  Thr  Glu
               85                       90                      95

Cys  Arg  Leu  Gly  Leu  Lys  Glu  Glu  Asn  Pro  Ser  Lys  Lys  Ala  Phe  Glu
               100                      105                     110

Glu  Cys  Thr  Arg  Val  Ala  His  Asn  Tyr  Leu  Arg  Gly  Glu  Pro  Phe  Glu
               115                      120                     125

Glu  Tyr  Gln  Glu  Ser  Ser  Tyr  Phe  Ser  Gln  Phe  Leu  Gln  Trp  Lys  Trp
     130                      135                     140

Leu  Glu  Arg  Gln  Pro  Val  Thr  Lys  Asn  Thr  Phe  Arg  His  Tyr  Arg  Val
145                      150                      155                     160

Leu  Gly  Lys  Gly  Gly  Phe  Gly  Glu  Val  Cys  Ala  Cys  Gln  Val  Arg  Ala
               165                      170                     175
```

```
Thr Gly Lys Met Tyr Ala Cys Lys Lys Leu Gln Lys Lys Arg Ile Lys
            180                 185                 190

Lys Arg Lys Gly Glu Ala Met Ala Leu Asn Glu Lys Arg Ile Leu Glu
        195                 200                 205

Lys Val Gln Ser Arg Phe Val Ser Leu Ala Tyr Ala Tyr Glu Thr
    210                 215                 220

Lys Asp Ala Leu Cys Leu Val Leu Thr Ile Met Asn Gly Gly Asp Leu
225                 230                 235                     240

Lys Phe His Ile Tyr Asn Leu Gly Asn Pro Gly Phe Asp Glu Gln Arg
                245                 250                 255

Ala Val Phe Tyr Ala Ala Glu Leu Cys Cys Gly Leu Glu Asp Leu Gln
            260                 265                 270

Arg Glu Arg Ile Val Tyr Arg Asp Leu Lys Pro Glu Asn Ile Leu Leu
        275                 280                 285

Asp Asp Arg Gly His Ile Arg Ile Ser Asp Leu Gly Leu Ala Thr Glu
    290                 295                 300

Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
                325                 330                 335

Trp Trp Gly Leu Gly Cys Leu Ile Tyr Glu Met Ile Gln Gly His Ser
            340                 345                 350

Pro Phe Lys Lys Tyr Lys Glu Lys Val Lys Trp Glu Glu Val Asp Gln
        355                 360                 365

Arg Ile Lys Asn Asp Thr Glu Glu Tyr Ser Glu Lys Phe Ser Glu Asp
    370                 375                 380

Ala Lys Ser Ile Cys Arg Met Leu Leu Thr Lys Asn Pro Ser Lys Arg
385                 390                 395                 400

Leu Gly Cys Arg Gly Glu Gly Ala Ala Gly Val Lys Gln His Pro Val
                405                 410                 415

Phe Lys Asp Ile Asn Phe Arg Arg Leu Glu Ala Asn Met Leu Glu Pro
            420                 425                 430

Pro Phe Cys Pro Asp Pro His Ala Val Tyr Cys Lys Asp Val Leu Asp
        435                 440                 445

Ile Glu Gln Phe Ser Ala Val Lys Gly Ile Tyr Leu Asp Thr Ala Asp
    450                 455                 460

Glu Asp Phe Tyr Ala Arg Phe Ala Thr Gly Cys Val Ser Ile Pro Trp
465                 470                 475                 480

Gln Asn Glu Asp Cys Leu Thr Met Val Pro Ser Glu Lys Glu Val Glu
                485                 490                 495

Pro Lys Gln Cys
            500
```

( 2 ) INFORMATION FOR SEQ ID NO:16:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Asp Phe Gly Ser Leu Glu Thr Val Val Ala Asn Ser Ala Phe Ile
1               5                   10                  15

Ala Ala Arg Gly Ser Phe Asp Ala Ser Ser Gly Pro Ala Ser Arg Asp
```

|   |   |   |   |   | 20 |   |   |   |   | 25 |   |   |   |   | 30 |   |   |
|---|---|---|---|---|---|---|---|---|---|---|---|---|---|---|---|---|---|
| Arg | Lys | Tyr 35 | Leu | Ala | Arg | Leu | Lys 40 | Leu | Pro | Pro | Leu | Ser 45 | Lys | Cys | Glu |
| Ala | Leu 50 | Arg | Glu | Ser | Leu | Asp 55 | Leu | Gly | Phe | Glu | Gly 60 | Met | Cys | Leu | Glu |
| Gln | Pro 65 | Ile | Gly | Lys | Arg 70 | Leu | Phe | Gln | Gln 75 | Phe | Leu | Arg | Thr | His | Glu 80 |
| Gln | His | Gly | Pro | Ala 85 | Leu | Gln | Leu | Trp | Lys 90 | Asp | Ile | Glu | Asp | Tyr 95 | Asp |
| Thr | Ala | Asp | Asp 100 | Ala | Leu | Arg | Pro | Gln 105 | Lys | Ala | Gln | Ala | Leu 110 | Arg | Ala |
| Ala | Tyr | Leu 115 | Glu | Pro | Gln | Ala | Gln 120 | Leu | Phe | Cys | Ser | Phe 125 | Leu | Asp | Ala |
| Glu | Thr 130 | Val | Ala | Arg | Ala | Arg 135 | Ala | Gly | Ala | Gly | Asp 140 | Gly | Leu | Phe | Gln |
| Pro 145 | Leu | Leu | Arg | Ala | Val 150 | Leu | Ala | His | Leu | Gly 155 | Gln | Ala | Pro | Phe | Gln 160 |
| Glu | Phe | Leu | Asp | Ser 165 | Leu | Tyr | Phe | Leu | Arg 170 | Phe | Leu | Gln | Trp | Lys 175 | Trp |
| Leu | Glu | Ala | Gln | Pro 180 | Met | Gly | Glu | Asp | Trp 185 | Phe | Leu | Asp | Phe 190 | Arg | Val |
| Leu | Gly | Arg 195 | Gly | Gly | Phe | Gly | Glu 200 | Val | Phe | Ala | Cys | Gln 205 | Met | Lys | Ala |
| Thr | Gly 210 | Lys | Leu | Tyr | Ala | Cys 215 | Lys | Lys | Leu | Asn | Lys 220 | Lys | Arg | Leu | Lys |
| Lys 225 | Arg | Lys | Gly | Tyr | Gln 230 | Gly | Ala | Met | Val | Glu 235 | Lys | Lys | Ile | Leu | Ala 240 |
| Lys | Val | His | Ser | Arg 245 | Phe | Ile | Val | Ser | Leu 250 | Ala | Tyr | Ala | Phe | Glu 255 | Thr |
| Lys | Thr | Asp | Leu 260 | Cys | Leu | Val | Met | Thr 265 | Ile | Met | Asn | Gly | Gly 270 | Asp | Ile |
| Arg | Tyr | His 275 | Ile | Tyr | Asn | Val | Asp 280 | Glu | Asp | Asn | Pro | Gly 285 | Phe | Gln | Glu |
| Pro | Arg 290 | Ala | Ile | Phe | Tyr | Thr 295 | Ala | Gln | Ile | Val | Ser 300 | Gly | Leu | Glu | His |
| Leu 305 | His | Gln | Arg | Asn | Ile 310 | Ile | Tyr | Arg | Asp | Leu 315 | Lys | Pro | Glu | Asn | Val 320 |
| Leu | Leu | Asp | Asp | Asp 325 | Gly | Asn | Val | Arg | Ile 330 | Ser | Asp | Leu | Gly | Leu 335 | Ala |
| Val | Glu | Leu | Lys 340 | Ala | Gly | Gln | Thr | Lys 345 | Thr | Lys | Gly | Tyr | Ala 350 | Gly | Thr |
| Pro | Gly | Phe 355 | Met | Ala | Pro | Glu | Leu 360 | Leu | Leu | Gly | Glu | Glu 365 | Tyr | Asp | Phe |
| Ser | Val 370 | Asp | Tyr | Phe | Ala | Leu 375 | Gly | Val | Thr | Leu | Tyr 380 | Glu | Met | Ile | Ala |
| Ala 385 | Arg | Gly | Pro | Phe | Arg 390 | Ala | Arg | Gly | Glu | Lys 395 | Val | Glu | Asn | Lys | Glu 400 |
| Leu | Lys | Gln | Arg | Val 405 | Leu | Glu | Gln | Ala | Val 410 | Thr | Tyr | Pro | Asp | Lys 415 | Phe |
| Ser | Pro | Ala | Ser 420 | Lys | Asp | Phe | Cys | Glu 425 | Ala | Leu | Leu | Gln | Lys 430 | Asp | Pro |
| Glu | Lys | Arg 435 | Leu | Gly | Phe | Arg | Asp 440 | Gly | Ser | Cys | Asp | Gly 445 | Leu | Arg | Thr |

| His | Pro | Leu | Phe | Arg | Asp | Ile | Ser | Trp | Arg | Gln | Leu | Glu | Ala | Gly | Met |
|---|---|---|---|---|---|---|---|---|---|---|---|---|---|---|---|
| | 450 | | | | 455 | | | | | 460 | | | | | |

| Leu | Thr | Pro | Pro | Phe | Val | Pro | Asp | Ser | Arg | Thr | Val | Tyr | Ala | Lys | Asn |
|---|---|---|---|---|---|---|---|---|---|---|---|---|---|---|---|
| 465 | | | | | 470 | | | | | 475 | | | | | 480 |

| Ile | Gln | Asp | Val | Gly | Ala | Phe | Ser | Thr | Val | Lys | Gly | Val | Ala | Phe | Glu |
|---|---|---|---|---|---|---|---|---|---|---|---|---|---|---|---|
| | | | | 485 | | | | | 490 | | | | | 495 | |

| Lys | Ala | Asp | Thr | Glu | Phe | Phe | Gln | Glu | Phe | Ala | Ser | Gly | Thr | Cys | Pro |
|---|---|---|---|---|---|---|---|---|---|---|---|---|---|---|---|
| | | | 500 | | | | | 505 | | | | | 510 | | |

| Ile | Pro | Trp | Gln | Glu | Glu | Met | Ile | Glu | Thr | Gly | Val | Phe | Gly | Asp | Leu |
|---|---|---|---|---|---|---|---|---|---|---|---|---|---|---|---|
| | | | 515 | | | | 520 | | | | | 525 | | | |

| Asn | Val | Trp | Arg | Pro | Asp | Gly | Gln | Met | Pro | Asp | Asp | Met | Lys | Gly | Val |
|---|---|---|---|---|---|---|---|---|---|---|---|---|---|---|---|
| | 530 | | | | | 535 | | | | | 540 | | | | |

| Ser | Gly | Gln | Glu | Ala | Ala | Pro | Ser | Ser | Lys | Ser | Gly | Met | Cys | Val | Leu |
|---|---|---|---|---|---|---|---|---|---|---|---|---|---|---|---|
| 545 | | | | | 550 | | | | | 555 | | | | | 560 |

| Ser |
|---|

( 2 ) INFORMATION FOR SEQ ID NO:17:

( i ) SEQUENCE CHARACTERISTICS:
        ( A ) LENGTH: 426 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met | Tyr | Phe | His | Arg | Tyr | Leu | Gln | Trp | Lys | Trp | Leu | Glu | Ala | Gln | Pro |
|---|---|---|---|---|---|---|---|---|---|---|---|---|---|---|---|
| 1 | | | | 5 | | | | | 10 | | | | | 15 | |

| Ile | Thr | Tyr | Lys | Thr | Phe | Arg | Met | Tyr | Arg | Val | Leu | Gly | Lys | Gly | Gly |
|---|---|---|---|---|---|---|---|---|---|---|---|---|---|---|---|
| | | | 20 | | | | | 25 | | | | | 30 | | |

| Phe | Gly | Glu | Val | Cys | Ala | Cys | Gln | Val | Arg | Ala | Thr | Gly | Lys | Met | Tyr |
|---|---|---|---|---|---|---|---|---|---|---|---|---|---|---|---|
| | | | 35 | | | | | 40 | | | | | 45 | | |

| Ala | Cys | Lys | Lys | Leu | Glu | Lys | Lys | Arg | Ile | Lys | Lys | Arg | Lys | Gly | Glu |
|---|---|---|---|---|---|---|---|---|---|---|---|---|---|---|---|
| | 50 | | | | | 55 | | | | | 60 | | | | |

| Ser | Met | Val | Leu | Ile | Glu | Lys | Gln | Ile | Leu | Gln | Lys | Ile | Asn | Ser | Pro |
|---|---|---|---|---|---|---|---|---|---|---|---|---|---|---|---|
| 65 | | | | | 70 | | | | | 75 | | | | | 80 |

| Phe | Val | Val | Asn | Leu | Ala | Tyr | Ala | Tyr | Glu | Thr | Lys | Asp | Ala | Leu | Cys |
|---|---|---|---|---|---|---|---|---|---|---|---|---|---|---|---|
| | | | | 85 | | | | | 90 | | | | | 95 | |

| Leu | Val | Leu | Thr | Ile | Met | Asn | Gly | Gly | Asp | Leu | Lys | Phe | His | Ile | Tyr |
|---|---|---|---|---|---|---|---|---|---|---|---|---|---|---|---|
| | | | 100 | | | | | 105 | | | | | 110 | | |

| Asn | Met | Gly | Gly | Glu | Pro | Gly | Phe | Glu | Leu | Glu | Arg | Ala | Arg | Phe | Tyr |
|---|---|---|---|---|---|---|---|---|---|---|---|---|---|---|---|
| | | 115 | | | | | 120 | | | | | 125 | | | |

| Ala | Ala | Glu | Val | Ala | Cys | Gly | Leu | Gln | His | Leu | His | Lys | Gln | Gly | Ile |
|---|---|---|---|---|---|---|---|---|---|---|---|---|---|---|---|
| | 130 | | | | | 135 | | | | | 140 | | | | |

| Val | Tyr | Arg | Asp | Cys | Lys | Pro | Glu | Asn | Ile | Leu | Leu | Asp | Asp | His | Gly |
|---|---|---|---|---|---|---|---|---|---|---|---|---|---|---|---|
| 145 | | | | | 150 | | | | | 155 | | | | | 160 |

| His | Val | Arg | Ile | Ser | Asp | Leu | Gly | Leu | Ala | Val | Glu | Ile | Pro | Glu | Gly |
|---|---|---|---|---|---|---|---|---|---|---|---|---|---|---|---|
| | | | | 165 | | | | | 170 | | | | | 175 | |

| Glu | Met | Val | Arg | Gly | Arg | Val | Gly | Thr | Val | Gly | Tyr | Met | Ala | Pro | Glu |
|---|---|---|---|---|---|---|---|---|---|---|---|---|---|---|---|
| | | | 180 | | | | | 185 | | | | | 190 | | |

| Val | Ile | Asp | Asn | Glu | Lys | Tyr | Ala | Phe | Ser | Pro | Asp | Trp | Phe | Ser | Phe |
|---|---|---|---|---|---|---|---|---|---|---|---|---|---|---|---|
| | | 195 | | | | | 200 | | | | | 205 | | | |

| Gly | Cys | Leu | Leu | Tyr | Glu | Met | Ile | Glu | Gly | Gln | Ala | Pro | Phe | Arg | Met |
|---|---|---|---|---|---|---|---|---|---|---|---|---|---|---|---|
| | 210 | | | | | 215 | | | | | 220 | | | | |

| Arg | Lys | Glu | Lys | Val | Lys | Arg | Glu | Glu | Val | Asp | Arg | Arg | Val | Lys | Glu |
|---|---|---|---|---|---|---|---|---|---|---|---|---|---|---|---|
| 225 | | | | | 230 | | | | | 235 | | | | | 240 |

```
Asp  Pro  Glu  Lys  Tyr  Ser  Ser  Lys  Phe  Asn  Asp  Glu  Ala  Lys  Ser  Met
               245                      250                     255

Cys  Gln  Gln  Leu  Leu  Ala  Lys  Ser  Ile  Lys  Gln  Arg  Leu  Gly  Cys  Arg
               260                      265                     270

Asn  Gly  Arg  Met  Gly  Gly  Gln  Asp  Val  Met  Ala  His  Pro  Phe  Phe  His
               275                      280                     285

Ser  Thr  Gln  Leu  Asn  Trp  Arg  Arg  Leu  Glu  Ala  Gly  Met  Leu  Glu  Pro
               290                      295                     300

Pro  Phe  Val  Pro  Asp  Pro  His  Ala  Val  Tyr  Ala  Lys  Asp  Val  Leu  Asp
305                           310                     315                     320

Ile  Glu  Gln  Phe  Ser  Thr  Val  Lys  Gly  Val  Asn  Ile  Asp  Glu  Ser  Asp
               325                      330                     335

Thr  Asn  Phe  Tyr  Thr  Lys  Phe  Asn  Thr  Gly  Ser  Val  Ser  Ile  Ser  Trp
               340                      345                     350

Gln  Asn  Glu  Met  Met  Glu  Thr  Glu  Cys  Phe  Arg  Glu  Leu  Asn  Val  Phe
               355                      360                     365

Gly  Pro  Glu  Glu  Cys  Pro  Thr  Pro  Asp  Leu  Gln  Ile  Asn  Ala  Ala  Pro
               370                      375                     380

Glu  Pro  Asp  Lys  Ala  Gly  Cys  Phe  Pro  Phe  Arg  Arg  Lys  Lys  Lys  Gln
385                           390                     395                     400

Pro  Ala  Arg  Thr  Gln  Pro  Ile  Pro  Ile  Pro  Glu  His  Leu  Leu  Thr  Thr
               405                      410                     415

His  Ser  Val  Ser  Ser  Thr  Thr  Val  Glu  Ser
               420                      425
```

( 2 ) INFORMATION FOR SEQ ID NO:18:

( i ) SEQUENCE CHARACTERISTICS:
    ( A ) LENGTH: 689 amino acids
    ( B ) TYPE: amino acid
    ( D ) TOPOLOGY: linear ( i i ) MOLECULE TYPE: protein ( x i ) SEQUENCE DESCRIPTION: SEQ ID NO:18:

```
Met  Ala  Asp  Leu  Glu  Ala  Val  Leu  Ala  Asp  Val  Ser  Tyr  Leu  Met  Ala
1                   5                   10                      15

Met  Glu  Lys  Ser  Lys  Ala  Thr  Pro  Ala  Ala  Arg  Ala  Ser  Lys  Lys  Ile
               20                       25                      30

Leu  Leu  Pro  Glu  Pro  Ser  Ile  Arg  Ser  Val  Met  Gln  Lys  Tyr  Leu  Glu
               35                       40                      45

Asp  Arg  Gly  Glu  Val  Thr  Phe  Glu  Lys  Ile  Phe  Ser  Gln  Lys  Leu  Gly
     50                       55                      60

Tyr  Leu  Leu  Phe  Arg  Asp  Phe  Cys  Leu  Asn  His  Leu  Glu  Glu  Ala  Arg
65                            70                      75                      80

Pro  Leu  Val  Glu  Phe  Tyr  Glu  Glu  Ile  Lys  Lys  Tyr  Glu  Lys  Leu  Glu
               85                       90                      95

Thr  Glu  Glu  Glu  Arg  Val  Ala  Arg  Ser  Arg  Glu  Ile  Phe  Asp  Ser  Tyr
               100                      105                     110

Ile  Met  Lys  Glu  Leu  Leu  Ala  Cys  Ser  His  Pro  Phe  Ser  Lys  Ser  Ala
               115                      120                     125

Thr  Glu  His  Val  Gln  Gly  His  Leu  Gly  Lys  Lys  Gln  Val  Pro  Pro  Asp
     130                      135                     140

Leu  Phe  Gln  Pro  Tyr  Ile  Glu  Glu  Ile  Cys  Gln  Asn  Leu  Arg  Gly  Asp
145                           150                     155                     160

Val  Phe  Gln  Lys  Phe  Ile  Glu  Ser  Asp  Lys  Phe  Thr  Arg  Phe  Cys  Gln
               165                      170                     175
```

| | | | | | | | | | | | | | | |
|---|---|---|---|---|---|---|---|---|---|---|---|---|---|---|
|Trp|Lys|Asn|Val 180|Glu|Leu|Asn|Ile|His 185|Leu|Thr|Met|Asn|Phe 190|Ser|
|Val|His|Arg 195|Ile|Ile|Gly|Arg|Gly 200|Gly|Phe|Gly|Glu 205|Val|Tyr|Gly|Cys|
|Arg|Lys 210|Ala|Asp|Thr|Gly|Lys 215|Met|Tyr|Ala|Met|Lys 220|Cys|Leu|Asp|Lys|
|Lys 225|Arg|Ile|Lys|Met|Lys 230|Gln|Glu|Thr|Leu 235|Ala|Leu|Asn|Glu|Arg 240|
|Ile|Met|Leu|Ser|Leu 245|Val|Ser|Thr|Gly|Asp 250|Cys|Pro|Phe|Ile|Val 255|Cys|
|Met|Ser|Tyr|Ala 260|Phe|His|Thr|Pro|Asp 265|Lys|Leu|Ser|Phe|Ile 270|Leu|Asp|
|Leu|Met|Asn 275|Gly|Gly|Asp|Leu|His 280|Tyr|His|Leu|Ser|Gln 285|His|Gly|Val|
|Phe|Ser 290|Glu|Ala|Asp|Met|Arg 295|Phe|Tyr|Ala|Ala|Glu 300|Ile|Ile|Leu|Gly|
|Leu 305|Glu|His|Met|His|Asn 310|Arg|Phe|Val|Val|Tyr 315|Arg|Asp|Leu|Lys|Pro 320|
|Ala|Asn|Ile|Leu|Leu 325|Asp|Glu|His|Gly|His 330|Val|Arg|Ile|Ser|Asp 335|Leu|
|Gly|Leu|Ala|Cys 340|Asp|Phe|Ser|Lys|Lys 345|Lys|Pro|His|Ala|Ser 350|Val|Gly|
|Thr|His|Gly 355|Tyr|Met|Ala|Pro|Glu 360|Val|Leu|Gln|Lys|Gly 365|Val|Ala|Tyr|
|Asp|Ser 370|Ser|Ala|Asp|Trp|Phe 375|Ser|Leu|Gly|Cys|Met 380|Leu|Phe|Lys|Leu|
|Leu 385|Arg|Gly|His|Ser|Pro 390|Phe|Arg|Gln|His|Lys 395|Thr|Lys|Asp|Lys|His 400|
|Glu|Ile|Asp|Arg|Met 405|Thr|Leu|Thr|Met|Ala 410|Val|Glu|Leu|Pro|Asp 415|Ser|
|Phe|Ser|Pro|Glu 420|Leu|Arg|Ser|Leu|Leu 425|Glu|Gly|Leu|Leu|Gln 430|Arg|Asp|
|Val|Asn|Arg 435|Arg|Leu|Gly|Cys|Leu 440|Gly|Arg|Gly|Ala|Gln 445|Glu|Val|Lys|
|Glu|Ser 450|Pro|Phe|Phe|Arg|Ser 455|Leu|Asp|Trp|Gln|Met 460|Val|Phe|Leu|Gln|
|Lys 465|Tyr|Pro|Pro|Pro|Leu 470|Ile|Pro|Pro|Arg|Gly 475|Glu|Val|Asn|Ala|Ala 480|
|Asp|Ala|Phe|Asp|Ile 485|Gly|Ser|Phe|Asp|Glu 490|Glu|Asp|Thr|Lys|Gly 495|Ile|
|Lys|Leu|Leu|Asp 500|Ser|Asp|Gln|Glu|Leu 505|Tyr|Arg|Asn|Phe|Pro 510|Leu|Thr|
|Ile|Ser|Glu 515|Arg|Trp|Gln|Gln|Glu 520|Val|Ala|Glu|Thr|Val 525|Phe|Asp|Thr|
|Ile|Asn|Ala 530|Glu|Thr|Asp|Arg|Leu 535|Glu|Ala|Arg|Lys|Lys 540|Ala|Lys|Asn|
|Lys|Gln 545|Leu|Gly|His|Glu|Glu 550|Asp|Tyr|Ala|Leu|Gly 555|Lys|Asp|Cys|Ile 560|
|Met|His|Gly|Tyr|Met 565|Ser|Lys|Met|Gly|Asn 570|Pro|Phe|Leu|Thr|Gln 575|Trp|
|Gln|Arg|Arg|Tyr 580|Phe|Tyr|Leu|Phe|Pro 585|Asn|Arg|Leu|Glu|Trp 590|Arg|Gly|
|Glu|Gly|Glu|Ala|Pro|Gln|Ser|Leu|Leu|Thr|Met|Glu|Glu|Ile|Gln|Ser|

|     |     |     |     | 595 |     |     |     |     | 600 |     |     |     |     | 605 |     |
| --- | --- | --- | --- | --- | --- | --- | --- | --- | --- | --- | --- | --- | --- | --- | --- |
| Val | Glu | Glu | Thr | Gln | Ile | Lys | Glu | Arg | Lys | Cys | Leu | Leu | Lys | Ile |     |
|     | 610 |     |     |     |     | 615 |     |     |     |     | 620 |     |     |     |     |
| Arg | Gly | Gly | Lys | Gln | Phe | Ile | Leu | Gln | Cys | Asp | Ser | Asp | Pro | Glu | Leu |
| 625 |     |     |     |     | 630 |     |     |     |     | 635 |     |     |     |     | 640 |
| Val | Gln | Trp | Lys | Lys | Glu | Leu | Arg | Asp | Ala | Tyr | Arg | Glu | Ala | Gln | Gln |
|     |     |     |     | 645 |     |     |     |     | 650 |     |     |     |     | 655 |     |
| Leu | Val | Gln | Arg | Val | Pro | Lys | Met | Lys | Asn | Lys | Pro | Arg | Ser | Pro | Val |
|     |     |     | 660 |     |     |     |     | 665 |     |     |     |     | 670 |     |     |
| Val | Glu | Leu | Ser | Lys | Val | Pro | Leu | Val | Gln | Arg | Gly | Ser | Ala | Asn | Gly |
|     |     |     | 675 |     |     |     | 680 |     |     |     |     | 685 |     |     |     |
| Leu |     |     |     |     |     |     |     |     |     |     |     |     |     |     |     |

( 2 ) INFORMATION FOR SEQ ID NO:19:

( i ) SEQUENCE CHARACTERISTICS:
        ( A ) LENGTH: 688 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Asp | Leu | Glu | Ala | Val | Leu | Ala | Asp | Val | Ser | Tyr | Leu | Met | Ala |
| 1   |     |     |     | 5   |     |     |     |     | 10  |     |     |     |     | 15  |     |
| Met | Glu | Lys | Ser | Lys | Ala | Thr | Pro | Ala | Ala | Arg | Ala | Ser | Lys | Lys | Val |
|     |     |     | 20  |     |     |     |     | 25  |     |     |     |     | 30  |     |     |
| Val | Leu | Pro | Glu | Pro | Ser | Ile | Arg | Ser | Val | Met | Gln | Arg | Tyr | Leu | Ala |
|     |     |     | 35  |     |     |     | 40  |     |     |     |     | 45  |     |     |     |
| Glu | Arg | Asn | Glu | Ile | Thr | Phe | Asp | Lys | Ile | Phe | Asn | Gln | Lys | Ile | Gly |
|     | 50  |     |     |     |     | 55  |     |     |     |     | 60  |     |     |     |     |
| Phe | Leu | Leu | Phe | Lys | Asp | Phe | Cys | Leu | Asn | Glu | Ile | Gly | Glu | Ala | Val |
| 65  |     |     |     |     | 70  |     |     |     |     | 75  |     |     |     |     | 80  |
| Pro | Gln | Val | Lys | Phe | Tyr | Glu | Glu | Ile | Lys | Glu | Tyr | Glu | Lys | Leu | Asp |
|     |     |     |     | 85  |     |     |     |     | 90  |     |     |     |     | 95  |     |
| Asn | Glu | Glu | Asp | Arg | Leu | His | Arg | Ser | Arg | Gln | Met | Tyr | Asp | Ala | Tyr |
|     |     |     | 100 |     |     |     |     | 105 |     |     |     |     | 110 |     |     |
| Ile | Met | Arg | Glu | Leu | Leu | Ser | Ser | Thr | His | Gln | Phe | Ser | Lys | Gln | Ala |
|     |     | 115 |     |     |     |     | 120 |     |     |     |     | 125 |     |     |     |
| Val | Glu | His | Val | Gln | Ser | His | Leu | Ser | Lys | Lys | Gln | Val | Thr | Pro | Thr |
|     | 130 |     |     |     |     | 135 |     |     |     |     | 140 |     |     |     |     |
| Leu | Phe | Gln | Pro | Tyr | Ile | Glu | Glu | Ile | Cys | Glu | Ser | Leu | Arg | Gly | Asp |
| 145 |     |     |     |     | 150 |     |     |     |     | 155 |     |     |     |     | 160 |
| Ile | Phe | Gln | Lys | Phe | Met | Glu | Ser | Glu | Lys | Phe | Thr | Arg | Phe | Cys | Gln |
|     |     |     |     | 165 |     |     |     |     | 170 |     |     |     |     | 175 |     |
| Trp | Lys | Asn | Val | Glu | Leu | Asn | Ile | His | Leu | Ser | Met | Asn | Asp | Phe | Ser |
|     |     |     | 180 |     |     |     |     | 185 |     |     |     |     | 190 |     |     |
| Val | His | Arg | Ile | Ile | Gly | Arg | Gly | Gly | Phe | Gly | Glu | Val | Tyr | Gly | Cys |
|     |     | 195 |     |     |     |     | 200 |     |     |     |     | 205 |     |     |     |
| Arg | Lys | Ala | Asp | Thr | Gly | Lys | Met | Tyr | Ala | Met | Lys | Cys | Leu | Asp | Lys |
|     | 210 |     |     |     |     | 215 |     |     |     |     | 220 |     |     |     |     |
| Lys | Arg | Val | Lys | Met | Lys | Gln | Gly | Glu | Thr | Leu | Ala | Leu | Asn | Glu | Arg |
| 225 |     |     |     |     | 230 |     |     |     |     | 235 |     |     |     |     | 240 |
| Ile | Met | Leu | Ser | Leu | Val | Ser | Thr | Gly | Asp | Cys | Pro | Phe | Ile | Val | Cys |
|     |     |     |     | 245 |     |     |     |     | 250 |     |     |     |     | 255 |     |
| Met | Thr | Tyr | Ala | Phe | His | Thr | Pro | Asp | Lys | Leu | Cys | Phe | Ile | Leu | Asp |

|     |     |     |     |     | 260 |     |     |     |     | 265 |     |     |     |     | 270 |     |     |
| --- | --- | --- | --- | --- | --- | --- | --- | --- | --- | --- | --- | --- | --- | --- | --- | --- | --- |
| Leu | Met | Asn | Gly | Gly | Asp | Met | His | Tyr | His | Leu | Ser | Gln | His | Gly | Val |
|     |     |     | 275 |     |     |     | 280 |     |     |     |     | 285 |     |     |     |
| Phe | Ser | Glu | Lys | Glu | Met | Arg | Phe | Tyr | Ala | Ser | Glu | Ile | Ile | Leu | Gly |
|     |     | 290 |     |     |     | 295 |     |     |     | 300 |     |     |     |     |     |
| Leu | Glu | His | Met | His | Thr | Cys | Phe | Val | Val | Tyr | Arg | Asp | Leu | Lys | Pro |
| 305 |     |     |     |     | 310 |     |     |     | 315 |     |     |     |     |     | 320 |
| Ala | Asn | Ile | Leu | Leu | Asp | Glu | Tyr | Gly | His | Val | Arg | Ile | Ser | Asp | Leu |
|     |     |     |     | 325 |     |     |     |     | 330 |     |     |     |     | 335 |     |
| Gly | Leu | Ala | Cys | Asp | Phe | Ser | Lys | Lys | Pro | His | Ala | Ser | Val | Gly |
|     |     |     | 340 |     |     |     |     | 345 |     |     |     | 350 |     |     |
| Thr | His | Gly | Tyr | Met | Ala | Pro | Glu | Val | Leu | Gln | Lys | Gly | Thr | Cys | Tyr |
|     |     | 355 |     |     |     | 360 |     |     |     |     | 365 |     |     |     |     |
| Asp | Ser | Ser | Ala | Asp | Trp | Phe | Ser | Leu | Gly | Cys | Met | Leu | Phe | Lys | Leu |
|     | 370 |     |     |     |     | 375 |     |     |     |     | 380 |     |     |     |     |
| Leu | Arg | Gly | His | Ser | Pro | Phe | Arg | Gln | His | Lys | Thr | Lys | Asp | Lys | His |
| 385 |     |     |     |     | 390 |     |     |     |     | 395 |     |     |     |     | 400 |
| Glu | Ile | Asp | Arg | Met | Thr | Leu | Thr | Val | Asn | Val | Gln | Leu | Pro | Asp | Ala |
|     |     |     |     | 405 |     |     |     |     | 410 |     |     |     | 415 |     |     |
| Phe | Ser | Pro | Glu | Leu | Arg | Ser | Leu | Leu | Glu | Gly | Leu | Leu | Gln | Arg | Asp |
|     |     |     | 420 |     |     |     |     | 425 |     |     |     |     | 430 |     |     |
| Val | Ser | Gln | Arg | Leu | Gly | Cys | Tyr | Gly | Gly | Gly | Ala | Arg | Glu | Leu | Lys |
|     |     |     | 435 |     |     |     | 440 |     |     |     |     | 445 |     |     |     |
| Glu | His | Ile | Phe | Phe | Lys | Gly | Ile | Asp | Trp | Gln | Tyr | Val | Tyr | Leu | Arg |
|     | 450 |     |     |     |     | 455 |     |     |     |     | 460 |     |     |     |     |
| Lys | Tyr | Pro | Pro | Pro | Leu | Ile | Pro | Pro | Arg | Gly | Glu | Val | Asn | Ala | Ala |
| 465 |     |     |     |     | 470 |     |     |     |     | 475 |     |     |     |     | 480 |
| Asp | Ala | Phe | Asp | Ile | Gly | Ser | Phe | Asp | Glu | Glu | Asp | Thr | Lys | Gly | Ile |
|     |     |     |     | 485 |     |     |     |     | 490 |     |     |     |     | 495 |     |
| Lys | Leu | Leu | Asp | Cys | Asp | Gln | Asp | Leu | Tyr | Lys | Asn | Phe | Pro | Leu | Met |
|     |     |     |     | 500 |     |     |     |     | 505 |     |     |     | 510 |     |     |
| Ile | Ser | Glu | Arg | Trp | Gln | Gln | Glu | Val | Val | Glu | Thr | Ile | Tyr | Asp | Ala |
|     |     |     | 515 |     |     |     |     | 520 |     |     |     | 525 |     |     |     |
| Val | Asn | Ala | Glu | Thr | Asp | Lys | Ile | Glu | Ala | Arg | Lys | Lys | Ala | Lys | Asn |
|     | 530 |     |     |     |     | 535 |     |     |     |     | 540 |     |     |     |     |
| Lys | Gln | Leu | Cys | Gln | Glu | Glu | Asp | Tyr | Ala | Met | Gly | Lys | Asp | Cys | Ile |
| 545 |     |     |     |     | 550 |     |     |     |     | 555 |     |     |     |     | 560 |
| Met | His | Gly | Tyr | Met | Leu | Lys | Leu | Gly | Asn | Pro | Phe | Leu | Thr | Gln | Trp |
|     |     |     |     | 565 |     |     |     |     | 570 |     |     |     | 575 |     |     |
| Gln | Arg | Arg | Tyr | Phe | Tyr | Leu | Phe | Pro | Asn | Arg | Leu | Glu | Trp | Arg | Gly |
|     |     |     |     | 580 |     |     |     |     | 585 |     |     |     | 590 |     |     |
| Glu | Gly | Glu | Ser | Arg | Gln | Asn | Leu | Leu | Thr | Met | Glu | Gln | Ile | Met | Ser |
|     |     |     | 595 |     |     |     |     | 600 |     |     |     | 605 |     |     |     |
| Val | Glu | Glu | Thr | Gln | Ile | Lys | Asp | Arg | Lys | Cys | Ile | Leu | Leu | Arg | Val |
|     | 610 |     |     |     |     | 615 |     |     |     |     | 620 |     |     |     |     |
| Lys | Gly | Gly | Lys | Gln | Phe | Val | Leu | Gln | Cys | Glu | Ser | Asp | Pro | Glu | Phe |
| 625 |     |     |     |     | 630 |     |     |     |     | 635 |     |     |     |     | 640 |
| Ala | Gln | Trp | Leu | Lys | Glu | Leu | Thr | Cys | Thr | Phe | Asn | Glu | Ala | Gln | Arg |
|     |     |     |     | 645 |     |     |     |     | 650 |     |     |     | 655 |     |     |
| Leu | Leu | Arg | Arg | Ala | Pro | Lys | Phe | Leu | Asn | Lys | Pro | Arg | Ala | Ala | Ile |
|     |     |     | 660 |     |     |     |     | 665 |     |     |     | 670 |     |     |     |
| Leu | Glu | Phe | Ser | Lys | Pro | Pro | Leu | Cys | His | Arg | Asn | Ser | Ser | Gly | Leu |
|     |     | 675 |     |     |     |     | 680 |     |     |     |     | 685 |     |     |     |

( 2 ) INFORMATION FOR SEQ ID NO:20:

( i ) SEQUENCE CHARACTERISTICS:
        ( A ) LENGTH: 699 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Ala Asp Leu Glu Ala Val Leu Ala Asp Val Ser Tyr Leu Met Ala
 1               5                  10                  15

Met Glu Lys Ser Lys Cys Thr Pro Ala Arg Ala Ser Lys Lys Leu
                20                  25                  30

Asn Leu Pro Asp Pro Ser Val Arg Ser Val Met Tyr Lys Tyr Leu Glu
             35                  40                  45

Lys Glu Gly Glu Leu Asn Phe His Lys Asn Phe Asn Glu Val Leu Gly
         50                  55                  60

Tyr Leu Leu Phe Lys Asp Phe Cys Glu Asn Asp Ser Glu Glu Pro Ile
 65                  70                  75                  80

Gln Gln Leu Lys Phe Phe Glu Gln Ile Lys Leu Phe Glu Lys Thr Glu
                 85                  90                  95

Cys Tyr Asp Glu Arg Lys Lys Met Ala Arg Asp Ile Tyr Asp Asn Phe
                100                 105                 110

Ile Met Glu Glu Met Leu Ser His Thr Tyr Glu Tyr Ser Lys His Ala
            115                 120                 125

Val Ala Ser Val Gln Lys Tyr Leu Leu Lys Asn Glu Val Pro Val Asp
130                 135                 140

Leu Phe Glu Pro Tyr Leu Glu Glu Ile Phe Thr Gln Leu Lys Gly Lys
145                 150                 155                 160

Pro Phe Lys Lys Phe Leu Glu Ser Asp Lys Phe Thr Arg Phe Cys Gln
                165                 170                 175

Trp Lys Asn Leu Glu Leu Asn Ile Gln Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
210                 215                 220

Lys Arg Ile Lys Met Lys Gln Gly Glu Met Leu Ala Leu Asn Glu Arg
225                 230                 235                 240

Asn Met Leu Gln Ala Val Ser Thr Gly Ile Asp Cys Pro Phe Ile Val
                245                 250                 255

Cys Met Thr Tyr Ala Phe His Thr Pro Asp Lys Leu Cys Phe Ile Leu
            260                 265                 270

Asp Leu Met Asn Gly Gly Asp Leu His Tyr His Leu Ser Gln His Gly
        275                 280                 285

Ile Phe Ser Glu Asp Glu Met Lys Phe Tyr Ala Ala Glu Val Ile Leu
    290                 295                 300

Gly Leu Glu His Met His Lys Arg Cys Ile Val Tyr Arg Asp Leu Lys
305                 310                 315                 320

Pro Ala Asn Ile Leu Leu Asp Glu Asn Gly His Ile Arg Ile Ser Asp
                325                 330                 335

Leu Gly Leu Ala Cys Asp Phe Ser Lys Lys Lys Pro His Ala Ser Val
            340                 345                 350

Gly Thr His Gly Tyr Met Ala Pro Glu Val Leu Ser Lys Gly Thr Ser
        355                 360                 365
```

```
Tyr Asp Ser Cys Ala Asp Trp Phe Ser Phe Gly Cys Met Leu Tyr Lys
    370             375             380
Leu Leu Lys Gly His Ser Pro Phe Arg Gln His Lys Thr Lys Asp Lys
385             390             395                         400
Leu Glu Ile Asp Lys Met Thr Leu Thr Met Asn Val Glu Leu Pro Glu
                405             410                 415
Ser Phe Ser Leu Glu Leu Lys Asn Leu Leu Glu Met Leu Leu Gln Arg
            420             425             430
Asp Val Ser Lys Arg Leu Gly Cys Met Gly Asn Gly Ala Asp Glu Val
        435             440             445
Lys Met His Asn Phe Phe Cys Gly Ile Asp Trp His Gln Val Tyr Ile
    450             455             460
Gln Lys Tyr Thr Pro Pro Leu Val Pro Pro Arg Gly Glu Val Asn Ala
465             470             475                         480
Ala Asp Ala Phe Asp Ile Gly Ser Phe Asp Glu Asp Thr Lys Gly
                485             490             495
Ile Lys Leu Asn Asp Ala Asp Gln Asp Leu Tyr Lys Met Phe Ser Leu
            500             505             510
Thr Ile Ser Glu Arg Trp Gln Gln Glu Val Ser Glu Thr Val Phe Asp
        515             520             525
Thr Val Asn Thr Glu Thr Asp Lys Leu Glu Gln Lys Arg Lys Leu Lys
530                 535             540
Gln Lys Gln His Phe Asp Ala Asp Glu Lys Glu Ser Asp Cys Ile Leu
545             550             555             560
His Gly Tyr Ile Lys Lys Leu Gly Gly Ser Phe Ala Ser Leu Trp Gln
            565             570             575
Thr Lys Tyr Ala Lys Leu Tyr Pro Asn Arg Leu Glu Leu His Ser Glu
        580             585             590
Ser Gly Asn Asn Lys Pro Glu Leu Ile Phe Met Asp Gln Val Glu Asp
    595             600             605
Ile Ser Ser Asp Phe Ile Leu His Lys Asn Glu Asn Cys Ile Gln Ile
    610             615             620
Arg Ile Asn Asp Gly Thr Arg Asp Gly Arg Ile Ile Leu Thr Asn Ser
625             630             635                         640
Asp Glu Ile Gly Leu Lys Glu Trp Ser Ser Ser Leu Arg Ser Ala His
                645             650             655
Lys Ile Ser Gln Asp Leu Leu Gly Ser Met Ala Lys Lys Ala Gly Lys
            660             665             670
Ile Tyr Gly Ser Glu Arg Asp Val Asn Lys Ser Met Ile Phe Gly Gly
        675             680             685
Asn Cys Ser Thr Lys Thr Ser Asn Gly Ser Asn
690             695
```

( 2 ) INFORMATION FOR SEQ ID NO:21:

( i ) SEQUENCE CHARACTERISTICS:
        ( A ) LENGTH: 1983 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 13..1740

( x i ) SEQUENCE DESCRIPTION: SEQ ID NO:21:

```
GCCGTGCAGC CC ATG GAG CTC GAG AAC ATC GTA GCG AAC ACG GGG CTA                48
              Met Glu Leu Glu Asn Ile Val Ala Asn Thr Gly Leu
                1               5                  10

CTC AAG GCC CGG GAA GGT GGT GGC GGG AAT CGT AAA GGC AAG AGC AAG              96
Leu Lys Ala Arg Glu Gly Gly Gly Gly Asn Arg Lys Gly Lys Ser Lys
             15                  20                  25

AAA TGG CGC CAG ATG CTG CAG TTC CCC CAC ATC AGC CAG TGT GAA GAG             144
Lys Trp Arg Gln Met Leu Gln Phe Pro His Ile Ser Gln Cys Glu Glu
         30                  35                  40

CTC CGG CTC ACC TTG GAA CGT GAC TAC CAC AGC CTG TGT GAG CGT CAG             192
Leu Arg Leu Thr Leu Glu Arg Asp Tyr His Ser Leu Cys Glu Arg Gln
 45                  50                  55                  60

TCC ATT GGG CGC CTG TTA TTA TGT GAG TTC TGC GCT ACG AGG CCT GAG             240
Ser Ile Gly Arg Leu Leu Leu Cys Glu Phe Cys Ala Thr Arg Pro Glu
                 65                  70                  75

CTG ACC CGC TGT ACT GCC TTC CTG GAT GGG GTG GCT GAG TAT GAG GTG             288
Leu Thr Arg Cys Thr Ala Phe Leu Asp Gly Val Ala Glu Tyr Glu Val
             80                  85                  90

ACC CCT GAT GAG AAA CGG AAG GCA TGT GGG CGT CGG CTA ATG CAG AAT             336
Thr Pro Asp Glu Lys Arg Lys Ala Cys Gly Arg Arg Leu Met Gln Asn
         95                 100                 105

TTT CTG AGC CAC ACG GGT CCT GAC CTC ATC CCT GAA GTT CCC CGG CAG             384
Phe Leu Ser His Thr Gly Pro Asp Leu Ile Pro Glu Val Pro Arg Gln
110                 115                 120

CTG GTG AGT AAC TGT GCC CAG CGG CTA GAG CAG GGA CCC TGC AAA GAC             432
Leu Val Ser Asn Cys Ala Gln Arg Leu Glu Gln Gly Pro Cys Lys Asp
125                 130                 135                 140

CTC TTC CAG GAG CTG ACC CGG CTG ACC CAT GAG TAC CTA AGC ATG GGC             480
Leu Phe Gln Glu Leu Thr Arg Leu Thr His Glu Tyr Leu Ser Met Gly
                145                 150                 155

CCT TTT GGC GAC TAC CTC GAC AGC ATC TAC TTC AAC CGT TTC CTG CAG             528
Pro Phe Gly Asp Tyr Leu Asp Ser Ile Tyr Phe Asn Arg Phe Leu Gln
            160                 165                 170

TGG AAG TGG CTG GAA AGG CAG CCA GTG ACC AAA AAC ACC TTT AGG CAG             576
Trp Lys Trp Leu Glu Arg Gln Pro Val Thr Lys Asn Thr Phe Arg Gln
        175                 180                 185

TAC CGA GTC CTG GGC AAA GGT GGC TTT GGG GAG GTG TGT GCC TGC CAG             624
Tyr Arg Val Leu Gly Lys Gly Gly Phe Gly Glu Val Cys Ala Cys Gln
    190                 195                 200

GTG CGG ACA ACA GGC AAG ATG TAT GCG TAC AAA AAC TGG AAA AAG AAA             672
Val Arg Thr Thr Gly Lys Met Tyr Ala Tyr Lys Asn Trp Lys Lys Lys
205                 210                 215                 220

CGA ATA AAG AAG CGG AAG GGG GAG GCC ATG TCT CTC AAC GAG AAG CAG             720
Arg Ile Lys Lys Arg Lys Gly Glu Ala Met Ser Leu Asn Glu Lys Gln
                225                 230                 235

ATC CTG GAG AAA GTG AAC AGT AGG TTT GTA GTG ATC TTA GCC TAC GCA             768
Ile Leu Glu Lys Val Asn Ser Arg Phe Val Val Ile Leu Ala Tyr Ala
            240                 245                 250

TAT GAG ACC AAG GAT GCA CTG TGC CTG GTG CTG ACA TTG ATG AAT GGA             816
Tyr Glu Thr Lys Asp Ala Leu Cys Leu Val Leu Thr Leu Met Asn Gly
        255                 260                 265

GGC GAC CTC AAG TTC CAC ATC TAC CAC ATG GGC CAG GCT GGC TTT CCC             864
Gly Asp Leu Lys Phe His Ile Tyr His Met Gly Gln Ala Gly Phe Pro
    270                 275                 280

GAA GCA CGT GCT GTG TTC TAT GCT GCC GAG ATC TGC TGT GGT CTG GAG             912
Glu Ala Arg Ala Val Phe Tyr Ala Ala Glu Ile Cys Cys Gly Leu Glu
285                 290                 295                 300

GAC TTA CAC CGG GAA CGC ATC GTG TAC AGG GAC CTA AAG CCA GAG AAT             960
Asp Leu His Arg Glu Arg Ile Val Tyr Arg Asp Leu Lys Pro Glu Asn
                305                 310                 315
```

| | | | | | | | | | | | | | | | |
|---|---|---|---|---|---|---|---|---|---|---|---|---|---|---|---|
| ATC | CTT | CTG | GAT | GAC | CAT | GGC | CAC | ATT | CGA | ATC | TCC | GAC | CTG | GGC | CTG | 1008 |
| Ile | Leu | Leu | Asp | Asp | His | Gly | His | Ile | Arg | Ile | Ser | Asp | Leu | Gly | Leu | |
| | | | 320 | | | | | 325 | | | | | 330 | | | |
| GCT | GTG | CAT | GTT | CCT | GAG | GGC | CAG | ACC | ATC | AAA | GGC | CGT | GTG | GGC | ACT | 1056 |
| Ala | Val | His | Val | Pro | Glu | Gly | Gln | Thr | Ile | Lys | Gly | Arg | Val | Gly | Thr | |
| | | 335 | | | | | 340 | | | | | 345 | | | | |
| GTG | GGC | TAC | ATG | GCT | CCA | GAG | GTG | GTG | AAG | AAT | GAG | CGC | TAC | ACA | TTC | 1104 |
| Val | Gly | Tyr | Met | Ala | Pro | Glu | Val | Val | Lys | Asn | Glu | Arg | Tyr | Thr | Phe | |
| | 350 | | | | | 355 | | | | | 360 | | | | | |
| AGT | CCT | GAC | TGG | TGG | GCG | CTA | GGC | TGC | CTC | CTG | TAC | GAG | ATG | ATT | GCG | 1152 |
| Ser | Pro | Asp | Trp | Trp | Ala | Leu | Gly | Cys | Leu | Leu | Tyr | Glu | Met | Ile | Ala | |
| 365 | | | | | 370 | | | | | 375 | | | | | 380 | |
| GGA | CAG | TCG | CCC | TTC | CAG | CAG | AGG | AAG | AAG | AAG | ATC | AAG | CGG | GAG | GAG | 1200 |
| Gly | Gln | Ser | Pro | Phe | Gln | Gln | Arg | Lys | Lys | Lys | Ile | Lys | Arg | Glu | Glu | |
| | | | | 385 | | | | | 390 | | | | | 395 | | |
| GTG | GAG | CGG | CTG | GTC | AAG | GAG | GTG | GCT | GAG | GAG | TAC | ACC | GAC | CGC | TTC | 1248 |
| Val | Glu | Arg | Leu | Val | Lys | Glu | Val | Ala | Glu | Glu | Tyr | Thr | Asp | Arg | Phe | |
| | | | 400 | | | | | 405 | | | | | 410 | | | |
| TCC | CCA | CAG | GCA | CGC | TCA | CTC | TGT | TCT | CAG | CTT | CTC | AAC | AAG | GAC | CCT | 1296 |
| Ser | Pro | Gln | Ala | Arg | Ser | Leu | Cys | Ser | Gln | Leu | Leu | Asn | Lys | Asp | Pro | |
| | | 415 | | | | | 420 | | | | | 425 | | | | |
| GCT | GAG | CGC | CTG | GGG | TGT | CGT | GGA | GGT | GGT | GCC | CGT | GAG | GTA | AAG | GAG | 1344 |
| Ala | Glu | Arg | Leu | Gly | Cys | Arg | Gly | Gly | Gly | Ala | Arg | Glu | Val | Lys | Glu | |
| | 430 | | | | | 435 | | | | | 440 | | | | | |
| CAC | CCC | CTT | TTC | AAG | AAA | CTG | AAT | TTC | AAG | CGG | CTG | GGA | GCT | GGA | ATG | 1392 |
| His | Pro | Leu | Phe | Lys | Lys | Leu | Asn | Phe | Lys | Arg | Leu | Gly | Ala | Gly | Met | |
| 445 | | | | | 450 | | | | | 455 | | | | | 460 | |
| CTA | GAA | CCA | CCT | TTT | AAA | CCT | GAC | CCC | CAG | GCC | ATT | TAC | TGC | AAG | GAC | 1440 |
| Leu | Glu | Pro | Pro | Phe | Lys | Pro | Asp | Pro | Gln | Ala | Ile | Tyr | Cys | Lys | Asp | |
| | | | | 465 | | | | | 470 | | | | | 475 | | |
| GTG | CTG | GAC | ATT | GAA | CAG | TTC | TCC | ACA | GTT | AAA | GGT | GTG | GAT | CTG | GAG | 1488 |
| Val | Leu | Asp | Ile | Glu | Gln | Phe | Ser | Thr | Val | Lys | Gly | Val | Asp | Leu | Glu | |
| | | | 480 | | | | | 485 | | | | | 490 | | | |
| CCC | ACA | GAC | CAA | GAC | TTC | TAC | CAG | AAG | TTT | GCC | ACG | GGT | AGT | GTG | TCC | 1536 |
| Pro | Thr | Asp | Gln | Asp | Phe | Tyr | Gln | Lys | Phe | Ala | Thr | Gly | Ser | Val | Ser | |
| | | 495 | | | | | 500 | | | | | 505 | | | | |
| ATC | CCC | TGG | CAG | AAC | GAG | ATG | GTG | GAG | ACT | GAG | TGC | TTC | CAG | GAA | CTA | 1584 |
| Ile | Pro | Trp | Gln | Asn | Glu | Met | Val | Glu | Thr | Glu | Cys | Phe | Gln | Glu | Leu | |
| | 510 | | | | | 515 | | | | | 520 | | | | | |
| AAT | GTC | TTT | GGG | CTG | GAT | GGG | TCT | GTT | CCC | CCA | GAC | CTG | GAC | TGG | AAG | 1632 |
| Asn | Val | Phe | Gly | Leu | Asp | Gly | Ser | Val | Pro | Pro | Asp | Leu | Asp | Trp | Lys | |
| 525 | | | | | 530 | | | | | 535 | | | | | 540 | |
| GGC | CAG | CCC | ACT | GCA | CCC | CCC | AAG | AAG | GGA | TTG | CTA | CAG | AGA | CTC | TTC | 1680 |
| Gly | Gln | Pro | Thr | Ala | Pro | Pro | Lys | Lys | Gly | Leu | Leu | Gln | Arg | Leu | Phe | |
| | | | | 545 | | | | | 550 | | | | | 555 | | |
| AGT | AGA | CAA | GAT | TGC | TGT | GGG | AAC | TGC | AGC | GAC | AGT | GAA | GAA | GAG | CTC | 1728 |
| Ser | Arg | Gln | Asp | Cys | Cys | Gly | Asn | Cys | Ser | Asp | Ser | Glu | Glu | Glu | Leu | |
| | | | 560 | | | | | 565 | | | | | 570 | | | |
| CCC | ACC | CGC | CTC | TAGCCCCCAG | GCCGAGGCCC | CCACCGGCGG | CTGGCGGTAG | | | | | | | | | 1780 |
| Pro | Thr | Arg | Leu | | | | | | | | | | | | | |
| | | | 575 | | | | | | | | | | | | | |

| | | | | |
|---|---|---|---|---|
| CAGCTACTCA | GTGACTGACG | TTGACAGTTT | TGCACAGTGC | TGTTTCCAGT | TGTCCACGCC | 1840 |
| AGTCGTGGTC | TGTGGAACAC | AGCCGGAACT | GTCCCCAGTG | TCCTCCGTTC | CTCAGCCACT | 1900 |
| GGCCCAGCTT | GAGTATGACG | AGGCCTGGGC | CATCTTGGGA | CAAAGGTGCG | TCCCTTCAGC | 1960 |
| TCTTCTCTGT | GGAGCTCGGG | GCG | | | | 1983 |

( 2 ) INFORMATION FOR SEQ ID NO:22:

( i ) SEQUENCE CHARACTERISTICS:
  ( A ) LENGTH: 576 amino acids
  ( B ) TYPE: amino acid
  ( D ) TOPOLOGY: linear ( i i ) MOLECULE TYPE: protein ( x i ) SEQUENCE DESCRIPTION: SEQ ID NO:22:

```
Met Glu Leu Glu Asn Ile Val Ala Asn Thr Gly Leu Leu Lys Ala Arg
 1               5                  10                  15

Glu Gly Gly Gly Gly Asn Arg Lys Gly Lys Ser Lys Lys Trp Arg Gln
            20                  25                  30

Met Leu Gln Phe Pro His Ile Ser Gln Cys Glu Glu Leu Arg Leu Thr
        35                  40                  45

Leu Glu Arg Asp Tyr His Ser Leu Cys Glu Arg Gln Ser Ile Gly Arg
 50                  55                  60

Leu Leu Leu Cys Glu Phe Cys Ala Thr Arg Pro Glu Leu Thr Arg Cys
 65                  70                  75                  80

Thr Ala Phe Leu Asp Gly Val Ala Glu Tyr Glu Val Thr Pro Asp Glu
                 85                  90                  95

Lys Arg Lys Ala Cys Gly Arg Arg Leu Met Gln Asn Phe Leu Ser His
            100                 105                 110

Thr Gly Pro Asp Leu Ile Pro Glu Val Pro Arg Gln Leu Val Ser Asn
        115                 120                 125

Cys Ala Gln Arg Leu Glu Gln Gly Pro Cys Lys Asp Leu Phe Gln Glu
130                 135                 140

Leu Thr Arg Leu Thr His Glu Tyr Leu Ser Met Gly Pro Phe Gly Asp
145                 150                 155                 160

Tyr Leu Asp Ser Ile Tyr Phe Asn Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Thr Thr
        195                 200                 205

Gly Lys Met Tyr Ala Tyr Lys Asn Trp Lys Lys Lys Arg Ile Lys Lys
210                 215                 220

Arg Lys Gly Glu Ala Met Ser Leu Asn Glu Lys Gln Ile Leu Glu Lys
225                 230                 235                 240

Val Asn Ser Arg Phe Val Val Ile Leu Ala Tyr Ala Tyr Glu Thr Lys
                245                 250                 255

Asp Ala Leu Cys Leu Val Leu Thr Leu Met Asn Gly Gly Asp Leu Lys
            260                 265                 270

Phe His Ile Tyr His Met Gly Gln Ala Gly Phe Pro Glu Ala Arg Ala
        275                 280                 285

Val Phe Tyr Ala Ala Glu Ile Cys Cys Gly Leu Glu Asp Leu His Arg
290                 295                 300

Glu Arg Ile Val Tyr Arg Asp Leu Lys Pro Glu Asn Ile Leu Leu Asp
305                 310                 315                 320

Asp His Gly His Ile Arg Ile Ser Asp Leu Gly Leu Ala Val His Val
                325                 330                 335

Pro Glu Gly Gln Thr Ile Lys Gly Arg Val Gly Thr Val Gly Tyr Met
            340                 345                 350

Ala Pro Glu Val Val Lys Asn Glu Arg Tyr Thr Phe Ser Pro Asp Trp
        355                 360                 365

Trp Ala Leu Gly Cys Leu Leu Tyr Glu Met Ile Ala Gly Gln Ser Pro
370                 375                 380
```

| | | | | | | | | | | | | | | | |
|---|---|---|---|---|---|---|---|---|---|---|---|---|---|---|---|
| Phe | Gln | Gln | Arg | Lys | Lys | Lys | Ile | Lys | Arg | Glu | Glu | Val | Glu | Arg | Leu |
| 385 | | | | | 390 | | | | | 395 | | | | | 400 |
| Val | Lys | Glu | Val | Ala | Glu | Glu | Tyr | Thr | Asp | Arg | Phe | Ser | Pro | Gln | Ala |
| | | | | 405 | | | | | 410 | | | | | 415 | |
| Arg | Ser | Leu | Cys | Ser | Gln | Leu | Leu | Asn | Lys | Asp | Pro | Ala | Glu | Arg | Leu |
| | | | 420 | | | | | 425 | | | | | 430 | | |
| Gly | Cys | Arg | Gly | Gly | Gly | Ala | Arg | Glu | Val | Lys | Glu | His | Pro | Leu | Phe |
| | | 435 | | | | | 440 | | | | | 445 | | | |
| Lys | Lys | Leu | Asn | Phe | Lys | Arg | Leu | Gly | Ala | Gly | Met | Leu | Glu | Pro | Pro |
| | 450 | | | | | 455 | | | | | 460 | | | | |
| Phe | Lys | Pro | Asp | Pro | Gln | Ala | Ile | Tyr | Cys | Lys | Asp | Val | Leu | Asp | Ile |
| 465 | | | | | 470 | | | | | 475 | | | | | 480 |
| Glu | Gln | Phe | Ser | Thr | Val | Lys | Gly | Val | Asp | Leu | Glu | Pro | Thr | Asp | Gln |
| | | | | 485 | | | | | 490 | | | | | 495 | |
| Asp | Phe | Tyr | Gln | Lys | Phe | Ala | Thr | Gly | Ser | Val | Ser | Ile | Pro | Trp | Gln |
| | | | 500 | | | | | 505 | | | | | 510 | | |
| Asn | Glu | Met | Val | Glu | Thr | Glu | Cys | Phe | Gln | Glu | Leu | Asn | Val | Phe | Gly |
| | | 515 | | | | | 520 | | | | | 525 | | | |
| Leu | Asp | Gly | Ser | Val | Pro | Pro | Asp | Leu | Asp | Trp | Lys | Gly | Gln | Pro | Thr |
| | 530 | | | | | 535 | | | | | 540 | | | | |
| Ala | Pro | Pro | Lys | Lys | Gly | Leu | Leu | Gln | Arg | Leu | Phe | Ser | Arg | Gln | Asp |
| 545 | | | | | 550 | | | | | 555 | | | | | 560 |
| Cys | Cys | Gly | Asn | Cys | Ser | Asp | Ser | Glu | Glu | Glu | Leu | Pro | Thr | Arg | Leu |
| | | | | 565 | | | | | 570 | | | | | 575 | |

( 2 ) INFORMATION FOR SEQ ID NO:23:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

```
ATTTCTAGAA  TTCGTTTCCT  GCAGTGGAAG  TGG                          33
```

( 2 ) INFORMATION FOR SEQ ID NO:24:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

```
ATTAAGCTTT  TAGTGATGGT  GATGGTGATG  CGGCTCCAGC  ATGCCAGC         48
```